(12) United States Patent
McDowell et al.

(10) Patent No.: US 8,383,791 B1
(45) Date of Patent: Feb. 26, 2013

(54) OLIGONUCLEOTIDES

(75) Inventors: David Gordon McDowell, Middlesex (GB); David John French, Middlesex (GB)

(73) Assignee: LGC Limited, Tedding, Middlesex (GB)

( * ) Notice: Subject to any disclaimer, the term of this patent is extended or adjusted under 35 U.S.C. 154(b) by 266 days.

(21) Appl. No.: 11/988,946

(22) PCT Filed: Jul. 20, 2006

(86) PCT No.: PCT/GB2006/002719
§ 371 (c)(1),
(2), (4) Date: Aug. 27, 2008

(87) PCT Pub. No.: WO2007/010268
PCT Pub. Date: Jan. 25, 2007

(30) Foreign Application Priority Data

Jul. 20, 2005 (GB) .................................. 0514889.5

(51) Int. Cl.
C07H 21/04 (2006.01)
(52) U.S. Cl. ...................................... 536/23.1; 536/24.3
(58) Field of Classification Search ........................ None
See application file for complete search history.

(56) References Cited

U.S. PATENT DOCUMENTS

| | | | |
|---|---|---|---|
| 5,691,146 A | 11/1997 | Mayrand et al. | |
| 6,174,670 B1 | 1/2001 | Wittwer et al. | |
| 6,635,427 B2 | 10/2003 | Wittwer et al. | |
| 2004/0091864 A1* | 5/2004 | French et al. | 435/6 |
| 2006/0172317 A1* | 8/2006 | Wang | 435/6 |
| 2006/0188902 A1* | 8/2006 | Narayanan et al. | 435/6 |

FOREIGN PATENT DOCUMENTS

| | | |
|---|---|---|
| WO | WO 94/02640 | 2/1994 |
| WO | WO 01/36668 A1 | 5/2001 |
| WO | WO 01/73118 A2 | 10/2001 |
| WO | WO 2007/010268 A3 | 5/2007 |

OTHER PUBLICATIONS

Bertrand et al. Nucleolar localization of early tRNA processing. Genes & Development (1998) vol. 12, pp. 2463-2468.*
Brown et al. (2001) Synthesis of a modified thymidine monomer for site-specific incorporation of reporter groups into oligonucleotides. Tetrahedron Lett. 42, 2587-2591.
Crockett & Wittwer (2001) Fluorescein-Labeled Oligonucleotides for Real-Time PCR: Using the Inherent Quenching of Deoxyguanosine Nucleotides. Anal. Biochem., 290, 89-97.
Dobson et al (2003) Synthesis of HyBeacons and dual-labelled probes containing 2'-fluorescent groups for use in genetic analysis. Chem. Comm. 11, 1234-1235.
Elnifro et al. (2000) PCR and restriction endonuclease analysis for rapid identification of Human Adenovirus subgenera. J. Clin. Microbiol. 38, 2055-2061.
French et al. (2001) HyBeacon probes: a new tool for DNA sequence detection and allele discrimination. Molecular and Cellular Probes. 15, 363-74.
French et al. (2002) Ultra-rapid DNA analysis using HyBeacon probes and direct PCR amplification direct from saliva. Molecular and Cellular Probes. 16, 319-26.
Hawkins et al. (1997) Fluorescence properties of pteridine nucleoside analogs as monomers and incorporated into oligonucleotides. Anal. Biochem. 244, 86-95.
Heinlein et al. (2003) Photoinduced electron transfer between fluorescent dyes and guanosine residues DNA-hairpins. J. Phys. Chem. 107, 7957-7964.
Knemeyer et al. (2000). Probes for detection of specific DNA sequences at the single-molecule level. Anal. Chem. 72, 3717-24.
Lee et al. (1994) A fluorogenic assay for DNA cleavage reactions characterized with BamHI restriction endonucleoase. Anal. Biochem. 220, 377-83.
Lee et al. (2002) ResonSense: simple linear fluorescent probes for quantitative homogeneous rapid polymerase chain reaction. Analytica Chimica Acta 457, 61-70.
Marks et al. (2005) Molecular basis of action of HyBeacon fluorogenic probes: A spectroscopic and molecular dynamics study. Journal of Biomolecular Structure & Dynamics 23, 49-62.
McKeen et al. (2003) Synthesis of fluorophore and quencher monomers for use in Scorpion primers and nucleic acid structure probes. Organic and Biomolecular Chem. 1, 2267-2275.
Nazerenko et al. (2002) Multiplex quantitative PCR using self-quenched primers labeled with a single fluorophore. Nucleic Acids Res. 30, e37.
Nazerenko et al. (2002b) Effect of primary and secondary structure of oligodeoxyribonucleotides on the fluorescent properties of conjugated dyes. Nucleic Acids Res. 30, 2089-2195.
Norland et al. (1989) Structure and dynamics of a fluorescent DNA oligomer containing the EcoRI recognition sequence: fluorescence, molecular dynamics and NMR studies. Biochemistry 28, 9095-9103.
Radtkey et al. (2000) Rapid, high fidelity analysis of simple sequence repeats on an electronically active DNA microchip. Nucleic Acids Res. 28(7), e19(i) (vi).
Seidel et al. (1996) Nucleobase-specific quenching of fluorescent dyes. 1. Nucleobase one-electron redox potentials and their correlation with static and dynamic quenching efficiencies. J. Phys. Chem., 100, 5541-5553.
Solinas et al. (2001) Duplex Scorpion primers in SNP assays and FRET applications. Nucleic Acids Res. 29, e96.
Svanik et al. (2000) Detection of PCR products in real time using light-up probes. Analytical Biochemistry 287, 179-182.

(Continued)

Primary Examiner — Kenneth R. Horlick
Assistant Examiner — David Thomas
(74) Attorney, Agent, or Firm — Geoffrey M. Karny

(57) ABSTRACT

A single stranded oligonucleotide having substantially no secondary structure and formed of nucleotide residues wherein two or more internal nucleotide residues are labelled with a fluorophore without an associated quencher. Typically at least two of the nucleotide residues labelled with a fluorophore are separated by at least two unlabelled nucleotide residues. The oligonucleotides are useful in the investigation of target polynucleotide sequences.

48 Claims, 20 Drawing Sheets

OTHER PUBLICATIONS

Thelwell et al. (2000) Mode of action and application of Scorpion Primers to mutation detection. Nucleic Acids Res. 28, 3752-3761.
Tyagi & Kramer (1996) Molecular Beacons: probes that fluoresce upon hybridisation. Nature Biotechnology 14, 303-308.
Whitcombe et al. (1999) Detection of PCR products using self-probing amplicons and fluorescence. Nature Biotechnology 17, 804-807.
Xu et al. (1994) Melting and premelting transitions of an oligomer measured by DNA base fluorescence and absorption. Biochemistry 33, 9592-9599.
Zucker (2003) Mfold web server for nucleic acid folding and hybridisation prediction. Nucleic Acids Res. 31, 3406-3415.
Genbank Accession No. X14672, 2005.
Genbank Accession No. AY376850, 2003.
Genbank Accession No. AY364535, 2003.
Genbank Accession No. AY356351, 2005.
Genbank Accession No. X07547, 1999.
Genbank Accession No. M10316, 1996.
Genbank Accession No. AJ293905, 2005.
Genbank Accession No. AY130766, 2002.
Genbank Accession No. X52474, 2005.
Genbank Accession No. AF493953, 2002.
Genbank Accession No. NM_005957, 2008.
Written Opinion of the International Searching Authority of WIPO on International App. No. PCT/GB/2006/002719 (WO 07/010268) of LGC Limited for Oligonucleotides, Feb. 8, 2007.
International Preliminary Report on Patentability of the International Bureau of WIPO on International App. No. PCT/GB/2006/002719 (WO 07/010268) of LGC Limited for Oligonucleotides, Jan. 22, 2008.
Long et al., Spatial consequences of defective processing of specific yeast mRNAs revealed by fluorescent in situ hybridization, RNA 1: 1071-1078 (1995).
Zhang et al., Localization of pre-mRNA splicing in mammalian nuclei, Nature 372: 809-812 (1994).

* cited by examiner

A

B

A

B

A

B

SEQUENCE LISTING

```
<160> NUMBER OF SEQ ID NOS: 147

<210> SEQ ID NO 1
<211> LENGTH: 23
<212> TYPE: DNA
<213> ORGANISM: Homo sapiens
<220> FEATURE:
<221> NAME/KEY: misc_feature
<222> LOCATION: (11) ... (11)
<223> OTHER INFORMATION: Fluorescent-labelled nucleotide C6 FAM dU
```

-continued

```
<400> SEQUENCE: 1
gagaggaatc nggtacctgg acc                                          23

<210> SEQ ID NO 2
<211> LENGTH: 21
<212> TYPE: DNA
<213> ORGANISM: Homo sapiens

<400> SEQUENCE: 2
cctctagaat taatttctgg g                                            21

<210> SEQ ID NO 3
<211> LENGTH: 22
<212> TYPE: DNA
<213> ORGANISM: Homo sapiens

<400> SEQUENCE: 3
ctgctctctc ctgatttggt cc                                           22

<210> SEQ ID NO 4
<211> LENGTH: 23
<212> TYPE: DNA
<213> ORGANISM: Homo sapiens

<400> SEQUENCE: 4
ggtccaggta ccagattcct ctc                                          23

<210> SEQ ID NO 5
<211> LENGTH: 23
<212> TYPE: DNA
<213> ORGANISM: Homo sapiens

<400> SEQUENCE: 5
ggtccaagta ccagattcct ctc                                          23

<210> SEQ ID NO 6
<211> LENGTH: 24
<212> TYPE: DNA
<213> ORGANISM: Homo sapiens
<220> FEATURE:
<221> NAME/KEY: misc_feature
<222> LOCATION: (8)...(8)
<223> OTHER INFORMATION: Fluorescent-labelled C6 FAM dU

<400> SEQUENCE: 6
gaagtgcnga aaatatatt taag                                          24

<210> SEQ ID NO 7
<211> LENGTH: 24
<212> TYPE: DNA
<213> ORGANISM: Homo sapiens

<400> SEQUENCE: 7
cctatagaaa attcaattat aaag                                         24

<210> SEQ ID NO 8
<211> LENGTH: 20
<212> TYPE: DNA
<213> ORGANISM: Homo sapiens

<400> SEQUENCE: 8
cacgagattt ctccccaagg                                              20

<210> SEQ ID NO 9
```

```
<211> LENGTH: 24
<212> TYPE: DNA
<213> ORGANISM: Homo sapiens

<400> SEQUENCE: 9
cttaaatata tttttcagca cttc                                              24

<210> SEQ ID NO 10
<211> LENGTH: 24
<212> TYPE: DNA
<213> ORGANISM: Homo sapiens

<400> SEQUENCE: 10
cttaaatata tttctcagca cttc                                              24

<210> SEQ ID NO 11
<211> LENGTH: 20
<212> TYPE: DNA
<213> ORGANISM: Homo sapiens
<220> FEATURE:
<221> NAME/KEY: misc_feature
<222> LOCATION: (9)...(9)
<223> OTHER INFORMATION: Fluorescent-labelled nucleotide C6 FAM dU

<400> SEQUENCE: 11
cctggtgang aatcccttac                                                   20

<210> SEQ ID NO 12
<211> LENGTH: 24
<212> TYPE: DNA
<213> ORGANISM: Homo sapiens

<400> SEQUENCE: 12
cctatagaaa attcaattat aaag                                              24

<210> SEQ ID NO 13
<211> LENGTH: 20
<212> TYPE: DNA
<213> ORGANISM: Homo sapiens

<400> SEQUENCE: 13
cacgagattt ctccccaagg                                                   20

<210> SEQ ID NO 14
<211> LENGTH: 20
<212> TYPE: DNA
<213> ORGANISM: Homo sapiens

<400> SEQUENCE: 14
gtaagggatt catcaccagg                                                   20

<210> SEQ ID NO 15
<211> LENGTH: 20
<212> TYPE: DNA
<213> ORGANISM: Homo sapiens

<400> SEQUENCE: 15
gtaagggatc catcaccagg                                                   20

<210> SEQ ID NO 16
<211> LENGTH: 25
<212> TYPE: DNA
<213> ORGANISM: Homo sapiens
<220> FEATURE:
<221> NAME/KEY: misc_feature
<222> LOCATION: (13)...(13)
```

```
<223> OTHER INFORMATION: Fluorescent-labelled nucleotide Glen
      Fluorescein dT

<400> SEQUENCE: 16
ctttaaaata canttttat tatta                                          25

<210> SEQ ID NO 17
<211> LENGTH: 30
<212> TYPE: DNA
<213> ORGANISM: Homo sapiens

<400> SEQUENCE: 17
taataataaa aaatgtattt taaagatggc                                    30

<210> SEQ ID NO 18
<211> LENGTH: 30
<212> TYPE: DNA
<213> ORGANISM: Homo sapiens

<400> SEQUENCE: 18
taataataat aaatgtattt taaagatggc                                    30

<210> SEQ ID NO 19
<211> LENGTH: 30
<212> TYPE: DNA
<213> ORGANISM: Homo sapiens

<400> SEQUENCE: 19
taataataat aaatgtcttt taaagatggc                                    30

<210> SEQ ID NO 20
<211> LENGTH: 30
<212> TYPE: DNA
<213> ORGANISM: Homo sapiens

<400> SEQUENCE: 20
taataataaa aaatgtcttt taaagatggc                                    30

<210> SEQ ID NO 21
<211> LENGTH: 19
<212> TYPE: DNA
<213> ORGANISM: Homo sapiens
<220> FEATURE:
<221> NAME/KEY: misc_feature
<222> LOCATION: (6) ... (6)
<223> OTHER INFORMATION: Fluorescent-labelled nucleotide C6 FAM dU

<400> SEQUENCE: 21
ctgtantcct cgcctgtcc                                                19

<210> SEQ ID NO 22
<211> LENGTH: 29
<212> TYPE: DNA
<213> ORGANISM: Homo sapiens

<400> SEQUENCE: 22
ggactacttc taatctgtaa gagcagatc                                     29

<210> SEQ ID NO 23
<211> LENGTH: 31
<212> TYPE: DNA
<213> ORGANISM: Homo sapiens

<400> SEQUENCE: 23
gccccattat ttagccagga gacctaacat g                                  31
```

<210> SEQ ID NO 24
<211> LENGTH: 19
<212> TYPE: DNA
<213> ORGANISM: Homo sapiens

<400> SEQUENCE: 24
ggacaggcga ggaatacag                                                19

<210> SEQ ID NO 25
<211> LENGTH: 19
<212> TYPE: DNA
<213> ORGANISM: Homo sapiens

<400> SEQUENCE: 25
ggacaggcaa ggaatacag                                                19

<210> SEQ ID NO 26
<211> LENGTH: 19
<212> TYPE: DNA
<213> ORGANISM: Homo sapiens
<220> FEATURE:
<221> NAME/KEY: misc_feature
<222> LOCATION: (12)...(12)
<223> OTHER INFORMATION: Fluorescent-labelled nucleotide C6 FAM dU

<400> SEQUENCE: 26
gtgcacctga cncctgtgg                                                19

<210> SEQ ID NO 27
<211> LENGTH: 21
<212> TYPE: DNA
<213> ORGANISM: Homo sapiens

<400> SEQUENCE: 27
agggcagagc catctattgc t                                             21

<210> SEQ ID NO 28
<211> LENGTH: 19
<212> TYPE: DNA
<213> ORGANISM: Homo sapiens

<400> SEQUENCE: 28
catccacgtt caccttgcc                                                19

<210> SEQ ID NO 29
<211> LENGTH: 19
<212> TYPE: DNA
<213> ORGANISM: Homo sapiens

<400> SEQUENCE: 29
ccacaggagt caggtgcac                                                19

<210> SEQ ID NO 30
<211> LENGTH: 19
<212> TYPE: DNA
<213> ORGANISM: Homo sapiens

<400> SEQUENCE: 30
cctcaggagt caggtgcac                                                19

<210> SEQ ID NO 31
<211> LENGTH: 19
<212> TYPE: DNA
<213> ORGANISM: Homo sapiens

```
<400> SEQUENCE: 31
ccttaggagt caggtgcac                                                19

<210> SEQ ID NO 32
<211> LENGTH: 23
<212> TYPE: DNA
<213> ORGANISM: Chlamydia trachomatis
<220> FEATURE:
<221> NAME/KEY: misc_feature
<222> LOCATION: (13) ... (13)
<223> OTHER INFORMATION: Fluorescent-labelled nucleotide C6 FAM dU

<400> SEQUENCE: 32
caagcctgca aangtatacc aag                                           23

<210> SEQ ID NO 33
<211> LENGTH: 30
<212> TYPE: DNA
<213> ORGANISM: Chlamydia trachomatis

<400> SEQUENCE: 33
gggttcgttg tagagccatg tcctatcttg                                    30

<210> SEQ ID NO 34
<211> LENGTH: 30
<212> TYPE: DNA
<213> ORGANISM: Chlamydia trachomatis

<400> SEQUENCE: 34
cgcagctgct gtaatcaccc agtcgataaa                                    30

<210> SEQ ID NO 35
<211> LENGTH: 23
<212> TYPE: DNA
<213> ORGANISM: Chlamydia trachomatis

<400> SEQUENCE: 35
cttggtatac atttgcaggc ttg                                           23

<210> SEQ ID NO 36
<211> LENGTH: 23
<212> TYPE: DNA
<213> ORGANISM: Chlamydia trachomatis

<400> SEQUENCE: 36
cttggtatac atttacaggc ttg                                           23

<210> SEQ ID NO 37
<211> LENGTH: 23
<212> TYPE: DNA
<213> ORGANISM: Artificial Sequence
<220> FEATURE:
<223> OTHER INFORMATION: Artificially constructed PolyT probe
<220> FEATURE:
<221> NAME/KEY: misc_feature
<222> LOCATION: (12) ... (12)
<223> OTHER INFORMATION: Fluorescent-labelled nucleotide C6 FAM dU

<400> SEQUENCE: 37
tttttttttt tnttttttttt ttt                                          23

<210> SEQ ID NO 38
<211> LENGTH: 23
<212> TYPE: DNA
<213> ORGANISM: Artificial Sequence
```

```
<220> FEATURE:
<223> OTHER INFORMATION: Artificially constructed PolyA probe

<400> SEQUENCE: 38
aaaaaaaaaa aaaaaaaaaa aaa                                              23

<210> SEQ ID NO 39
<211> LENGTH: 19
<212> TYPE: DNA
<213> ORGANISM: Homo sapiens
<220> FEATURE:
<221> NAME/KEY: misc_feature
<222> LOCATION: (8)...(8)
<223> OTHER INFORMATION: Fluorescent-labelled nucleotide C6 FAM dU

<400> SEQUENCE: 39
gattattncc caggaaccc                                                   19

<210> SEQ ID NO 40
<211> LENGTH: 19
<212> TYPE: DNA
<213> ORGANISM: Homo sapiens

<400> SEQUENCE: 40
gggttcctgg gaaataatc                                                   19

<210> SEQ ID NO 41
<211> LENGTH: 19
<212> TYPE: DNA
<213> ORGANISM: Homo sapiens

<400> SEQUENCE: 41
gggttcccgg gaaataatc                                                   19

<210> SEQ ID NO 42
<211> LENGTH: 19
<212> TYPE: DNA
<213> ORGANISM: Homo sapiens
<220> FEATURE:
<221> NAME/KEY: misc_feature
<222> LOCATION: (5)...(5)
<223> OTHER INFORMATION: Fluorescent-labelled nucleotide C6 FAM dU

<400> SEQUENCE: 42
taccnggatc caggggtg                                                    19

<210> SEQ ID NO 43
<211> LENGTH: 19
<212> TYPE: DNA
<213> ORGANISM: Homo sapiens

<400> SEQUENCE: 43
caccccctgg atccaggta                                                   19

<210> SEQ ID NO 44
<211> LENGTH: 19
<212> TYPE: DNA
<213> ORGANISM: Homo sapiens

<400> SEQUENCE: 44
caccccctga atccaggta                                                   19

<210> SEQ ID NO 45
<211> LENGTH: 20
<212> TYPE: DNA
<213> ORGANISM: Hepatitis B virus
```

```
<220> FEATURE:
<221> NAME/KEY: misc_feature
<222> LOCATION: (11) ... (11)
<223> OTHER INFORMATION: Fluorescent-labelled nucleotide C6 FAM dU

<400> SEQUENCE: 45
aagaactccc ncgcctcgca                                              20

<210> SEQ ID NO 46
<211> LENGTH: 20
<212> TYPE: DNA
<213> ORGANISM: Hepatitis B virus

<400> SEQUENCE: 46
tgcgaggcga gggagttctt                                              20

<210> SEQ ID NO 47
<211> LENGTH: 21
<212> TYPE: DNA
<213> ORGANISM: Plasmodium junxanucleare
<220> FEATURE:
<221> NAME/KEY: misc_feature
<222> LOCATION: (13) ... (13)
<223> OTHER INFORMATION: Fluorescent-labelled nucleotide C6 FAM dU

<400> SEQUENCE: 47
gagacgaaca acngcgaaag c                                            21

<210> SEQ ID NO 48
<211> LENGTH: 21
<212> TYPE: DNA
<213> ORGANISM: Plasmodium junxanucleare

<400> SEQUENCE: 48
gctttcgcag ttgttcgtct c                                            21

<210> SEQ ID NO 49
<211> LENGTH: 22
<212> TYPE: DNA
<213> ORGANISM: Human herpes virus type 1 (HSV-1)
<220> FEATURE:
<221> NAME/KEY: misc_feature
<222> LOCATION: (13) ... (13)
<223> OTHER INFORMATION: Fluorescent-labelled nucleotide C6 FAM dU

<400> SEQUENCE: 49
ggacaccggc gcnacttcac ct                                           22

<210> SEQ ID NO 50
<211> LENGTH: 22
<212> TYPE: DNA
<213> ORGANISM: Human herpes virus type 1 (HSV-1)

<400> SEQUENCE: 50
aggtgaagta gcgccggtgt cc                                           22

<210> SEQ ID NO 51
<211> LENGTH: 16
<212> TYPE: DNA
<213> ORGANISM: Homo sapiens
<220> FEATURE:
<221> NAME/KEY: misc_feature
<222> LOCATION: (6) ... (6)
<223> OTHER INFORMATION: Fluorescent-labelled nucleotide C6 FAM dU

<400> SEQUENCE: 51
gggcgncctg ggggag                                                  16
```

-continued

```
<210> SEQ ID NO 52
<211> LENGTH: 16
<212> TYPE: DNA
<213> ORGANISM: Homo sapiens

<400> SEQUENCE: 52
ctcccccagg acgccc                                                         16

<210> SEQ ID NO 53
<211> LENGTH: 16
<212> TYPE: DNA
<213> ORGANISM: Homo sapiens

<400> SEQUENCE: 53
ctcccccaag acgccc                                                         16

<210> SEQ ID NO 54
<211> LENGTH: 20
<212> TYPE: DNA
<213> ORGANISM: Homo sapiens
<220> FEATURE:
<221> NAME/KEY: misc_feature
<222> LOCATION: (13)...(13)
<223> OTHER INFORMATION: Fluorescent-labelled nucleotide C6 FAM dU

<400> SEQUENCE: 54
cattgaggac tgngttcaag                                                     20

<210> SEQ ID NO 55
<211> LENGTH: 20
<212> TYPE: DNA
<213> ORGANISM: Homo sapiens

<400> SEQUENCE: 55
cttgaacaca gtcctcaatg                                                     20

<210> SEQ ID NO 56
<211> LENGTH: 20
<212> TYPE: DNA
<213> ORGANISM: Homo sapiens

<400> SEQUENCE: 56
cttgaacacg gtcctcaatg                                                     20

<210> SEQ ID NO 57
<211> LENGTH: 20
<212> TYPE: DNA
<213> ORGANISM: Homo sapiens
<220> FEATURE:
<221> NAME/KEY: misc_feature
<222> LOCATION: (13)...(13)
<223> OTHER INFORMATION: Fluorescent-labelled nucleotide C6 FAM dU

<400> SEQUENCE: 57
cattgaggac cgngttcaag                                                     20

<210> SEQ ID NO 58
<211> LENGTH: 20
<212> TYPE: DNA
<213> ORGANISM: Neisseria gonorrhoeae
<220> FEATURE:
<221> NAME/KEY: misc_feature
<222> LOCATION: (6)...(6)
<223> OTHER INFORMATION: Fluorescent-labelled nucleotide C6 FAM dU
<220> FEATURE:
<221> NAME/KEY: misc_feature
```

<222> LOCATION: (12) ... (12)
<223> OTHER INFORMATION: Fluorescent-labelled nucleotide C6 FAM dU

<400> SEQUENCE: 58
tctgcntccg cnacggcttc                                                 20

<210> SEQ ID NO 59
<211> LENGTH: 20
<212> TYPE: DNA
<213> ORGANISM: Neisseria gonorrhoeae

<400> SEQUENCE: 59
gaagccgtag cggaagcaga                                                 20

<210> SEQ ID NO 60
<211> LENGTH: 19
<212> TYPE: DNA
<213> ORGANISM: Homo sapiens
<220> FEATURE:
<221> NAME/KEY: misc_feature
<222> LOCATION: (6) ... (6)
<223> OTHER INFORMATION: Fluorescent-labelled nucleotide C6 FAM dU
<220> FEATURE:
<221> NAME/KEY: misc_feature
<222> LOCATION: (15) ... (15)
<223> OTHER INFORMATION: Fluorescent-labelled nucleotide C6 FAM dU

<400> SEQUENCE: 60
ctgtantcct cgccngtcc                                                  19

<210> SEQ ID NO 61
<211> LENGTH: 23
<212> TYPE: DNA
<213> ORGANISM: Chlamydia trachomatis
<220> FEATURE:
<221> NAME/KEY: misc_feature
<222> LOCATION: (7) ... (7)
<223> OTHER INFORMATION: Fluorescent-labelled nucleotide C6 FAM dU
<220> FEATURE:
<221> NAME/KEY: misc_feature
<222> LOCATION: (13) ... (13)
<223> OTHER INFORMATION: Fluorescent-labelled nucleotide C6 FAM dU

<400> SEQUENCE: 61
caagccngca aangtatacc aag                                             23

<210> SEQ ID NO 62
<211> LENGTH: 22
<212> TYPE: DNA
<213> ORGANISM: Influenza A virus
<220> FEATURE:
<221> NAME/KEY: misc_feature
<222> LOCATION: (8) ...(8)
<223> OTHER INFORMATION: Fluorescent-labelled nucleotide C6 FAM dU
<220> FEATURE:
<221> NAME/KEY: misc_feature
<222> LOCATION: (14) ... (14)
<223> OTHER INFORMATION: Fluorescent-labelled nucleotide C6 FAM dU

<400> SEQUENCE: 62
atgggaangg gganccaaat aa                                              22

<210> SEQ ID NO 63
<211> LENGTH: 22
<212> TYPE: DNA
<213> ORGANISM: Influenza A virus

<400> SEQUENCE: 63
ttatttggat ccccattccc at                                              22

<210> SEQ ID NO 64
<211> LENGTH: 27
<212> TYPE: DNA
<213> ORGANISM: Streptococcus pneumoniae
<220> FEATURE:
<221> NAME/KEY: misc_feature
<222> LOCATION: (8)...(8)
<223> OTHER INFORMATION: Fluorescent-labelled nucleotide C6 FAM dU
<220> FEATURE:
<221> NAME/KEY: misc_feature
<222> LOCATION: (14)...(14)
<223> OTHER INFORMATION: Fluorescent-labelled nucleotide C6 FAM dU

<400> SEQUENCE: 64
ggggtctncc actnggagaa agctatc                                        27

<210> SEQ ID NO 65
<211> LENGTH: 27
<212> TYPE: DNA
<213> ORGANISM: Streptococcus pneumoniae

<400> SEQUENCE: 65
gatagctttc tccaagtgga agacccc                                        27

<210> SEQ ID NO 66
<211> LENGTH: 26
<212> TYPE: DNA
<213> ORGANISM: Influenza A virus
<220> FEATURE:
<221> NAME/KEY: misc_feature
<222> LOCATION: (5)...(5)
<223> OTHER INFORMATION: Fluorescent-labelled nucleotide C6 FAM dU
<220> FEATURE:
<221> NAME/KEY: misc_feature
<222> LOCATION: (11)...(11)
<223> OTHER INFORMATION: Fluorescent-labelled nucleotide C6 FAM dU

<400> SEQUENCE: 66
ggganccaaa naacatggac agagct                                         26

<210> SEQ ID NO 67
<211> LENGTH: 26
<212> TYPE: DNA
<213> ORGANISM: Influenza A virus

<400> SEQUENCE: 67
agctctgtcc atgttatttg gatccc                                         26

<210> SEQ ID NO 68
<211> LENGTH: 24
<212> TYPE: DNA
<213> ORGANISM: Human Adenovirus C
<220> FEATURE:
<221> NAME/KEY: misc_feature
<222> LOCATION: (8)...(8)
<223> OTHER INFORMATION: Fluorescent-labelled nucleotide C6 FAM dU
<220> FEATURE:
<221> NAME/KEY: misc_feature
<222> LOCATION: (14)...(14)
<223> OTHER INFORMATION: Fluorescent-labelled nucleotide C6 FAM dU

<400> SEQUENCE: 68
gacgtggncc gtgngcacca gcct                                           24

<210> SEQ ID NO 69
<211> LENGTH: 24
<212> TYPE: DNA
<213> ORGANISM: Human Adenovirus C

<400> SEQUENCE: 69
aggctggtgc acacggacca cgtc                                        24

<210> SEQ ID NO 70
<211> LENGTH: 24
<212> TYPE: DNA
<213> ORGANISM: Human Adenovirus D

<400> SEQUENCE: 70
aggctggtgc actctgacca cgtc                                        24

<210> SEQ ID NO 71
<211> LENGTH: 24
<212> TYPE: DNA
<213> ORGANISM: Human Adenovirus D
<220> FEATURE:
<221> NAME/KEY: misc_feature
<222> LOCATION: (8)...(8)
<223> OTHER INFORMATION: Fluorescent-labelled nucleotide C6 FAM dU
<220> FEATURE:
<221> NAME/KEY: misc_feature
<222> LOCATION: (14)...(14)
<223> OTHER INFORMATION: Fluorescent-labelled nucleotide C6 FAM dU

<400> SEQUENCE: 71
gacgtggnca gagngcacca gcct                                        24

<210> SEQ ID NO 72
<211> LENGTH: 19
<212> TYPE: DNA
<213> ORGANISM: Homo sapiens
<220> FEATURE:
<221> NAME/KEY: misc_feature
<222> LOCATION: (8)...(8)
<223> OTHER INFORMATION: Glen amino-dC labelled with FAM post-synthesis
<220> FEATURE:
<221> NAME/KEY: misc_feature
<222> LOCATION: (14)...(14)
<223> OTHER INFORMATION: Glen amino-dC labelled with FAM post-synthesis

<400> SEQUENCE: 72
ctgtattnct cgcntgtcc                                              19

<210> SEQ ID NO 73
<211> LENGTH: 19
<212> TYPE: DNA
<213> ORGANISM: Homo sapiens
<220> FEATURE:
<221> NAME/KEY: misc_feature
<222> LOCATION: (13)...(13)
<223> OTHER INFORMATION: Glen amino-dA labelled with FAM post-synthesis

<400> SEQUENCE: 73
ggacaggcaa ggnatacag                                              19

<210> SEQ ID NO 74
<211> LENGTH: 20
<212> TYPE: DNA
<213> ORGANISM: Neisseria gonorrhoeae

<400> SEQUENCE: 74
actttggcga tattgctcgg                                             20

<210> SEQ ID NO 75
<211> LENGTH: 20
<212> TYPE: DNA
<213> ORGANISM: Neisseria gonorrhoeae

```
<400> SEQUENCE: 75
taccgagaac gaacgcgaca                                                    20

<210> SEQ ID NO 76
<211> LENGTH: 29
<212> TYPE: DNA
<213> ORGANISM: Human adenovirus C

<400> SEQUENCE: 76
gacatgactt tcgaggtcga tcccatgga                                          29

<210> SEQ ID NO 77
<211> LENGTH: 23
<212> TYPE: DNA
<213> ORGANISM: Human adenovirus C

<400> SEQUENCE: 77
gccgagaagg gcgtgcgcag gta                                                23

<210> SEQ ID NO 78
<211> LENGTH: 20
<212> TYPE: DNA
<213> ORGANISM: Influenza A virus

<400> SEQUENCE: 78
ggactgcagc gtagacgctt                                                    20

<210> SEQ ID NO 79
<211> LENGTH: 23
<212> TYPE: DNA
<213> ORGANISM: Influenza A virus

<400> SEQUENCE: 79
atttctttgg ccccatggaa tgt                                                23

<210> SEQ ID NO 80
<211> LENGTH: 22
<212> TYPE: DNA
<213> ORGANISM: Streptococcus pneumoniae
<220> FEATURE:
<221> NAME/KEY: misc_feature
<222> LOCATION: (8)...(8)
<223> OTHER INFORMATION: Fluorescent-labelled nucleotide C6 FAM dU

<400> SEQUENCE: 80
ggggtctncc acttggagaa ag                                                 22

<210> SEQ ID NO 81
<211> LENGTH: 26
<212> TYPE: DNA
<213> ORGANISM: Streptococcus pneumoniae

<400> SEQUENCE: 81
cttgcggttg atcgtgctcc gatgac                                             26

<210> SEQ ID NO 82
<211> LENGTH: 30
<212> TYPE: DNA
<213> ORGANISM: Streptococcus pneumoniae

<400> SEQUENCE: 82
cattattgac ctgaccataa tcttgatgcc                                         30
```

```
<210> SEQ ID NO 83
<211> LENGTH: 18
<212> TYPE: DNA
<213> ORGANISM: Ovis aries
<220> FEATURE:
<221> NAME/KEY: misc_feature
<222> LOCATION: (7) ... (7)
<223> OTHER INFORMATION: Fluorescent-labelled nucleotide C6 FAM dU

<400> SEQUENCE: 83
gggaagngcc atgagcag                                            18

<210> SEQ ID NO 84
<211> LENGTH: 18
<212> TYPE: DNA
<213> ORGANISM: Ovis Aries

<400> SEQUENCE: 84
ctgctcatgg cacttccc                                            18

<210> SEQ ID NO 85
<211> LENGTH: 20
<212> TYPE: DNA
<213> ORGANISM: Ovis aries
<220> FEATURE:
<221> NAME/KEY: misc_feature
<222> LOCATION: (8) ... (8)
<223> OTHER INFORMATION: Fluorescent-labelled nucleotide C6 FAM dU

<400> SEQUENCE: 85
cagtggancg gtatagtaac                                          20

<210> SEQ ID NO 86
<211> LENGTH: 20
<212> TYPE: DNA
<213> ORGANISM: Ovis aries

<400> SEQUENCE: 86
gttactatac cgatccactg                                          20

<210> SEQ ID NO 87
<211> LENGTH: 19
<212> TYPE: DNA
<213> ORGANISM: Homo sapiens
<220> FEATURE:
<221> NAME/KEY: misc_feature
<222> LOCATION: (5) ... (5)
<223> OTHER INFORMATION: Fluorescent-labelled nucleotide C6 FAM dU

<400> SEQUENCE: 87
gtatncctcg cctgtccag                                           19

<210> SEQ ID NO 88
<211> LENGTH: 22
<212> TYPE: DNA
<213> ORGANISM: Homo sapiens
<220> FEATURE:
<221> NAME/KEY: misc_feature
<222> LOCATION: (7) ... (7)
<223> OTHER INFORMATION: Fluorescent-labelled nucleotide C6 FAM dU

<400> SEQUENCE: 88
cttcaantgt ttgaggttca ag                                       22

<210> SEQ ID NO 89
<211> LENGTH: 22
<212> TYPE: DNA
<213> ORGANISM: Homo sapiens
```

```
<400> SEQUENCE: 89
cttgaacctc aaacaattga ag                                             22

<210> SEQ ID NO 90
<211> LENGTH: 19
<212> TYPE: DNA
<213> ORGANISM: Homo sapiens
<220> FEATURE:
<221> NAME/KEY: misc_feature
<222> LOCATION: (5)...(5)
<223> OTHER INFORMATION: Glen amino-dA labelled with FAM post-synthesis
<220> FEATURE:
<221> NAME/KEY: misc_feature
<222> LOCATION: (13)...(13)
<223> OTHER INFORMATION: Glen amino-dA labelled with FAM post-synthesis

<400> SEQUENCE: 90
ggacnggcaa ggnatacag                                                 19

<210> SEQ ID NO 91
<211> LENGTH: 19
<212> TYPE: DNA
<213> ORGANISM: Homo sapiens

<400> SEQUENCE: 91
ctgtatacct tgcctgtcc                                                 19

<210> SEQ ID NO 92
<211> LENGTH: 25
<212> TYPE: DNA
<213> ORGANISM: Homo sapiens

<400> SEQUENCE: 92
gactacttct aatctgtaag agcag                                          25

<210> SEQ ID NO 93
<211> LENGTH: 20
<212> TYPE: DNA
<213> ORGANISM: Homo sapiens

<400> SEQUENCE: 93
ccattattta gccaggagac                                                20

<210> SEQ ID NO 94
<211> LENGTH: 19
<212> TYPE: DNA
<213> ORGANISM: Homo sapiens
<220> FEATURE:
<221> NAME/KEY: misc_feature
<222> LOCATION: (19)...(19)
<223> OTHER INFORMATION: cytosine is labelled with FAM dye

<400> SEQUENCE: 94
ctgtattcct cgcctgtcc                                                 19

<210> SEQ ID NO 95
<211> LENGTH: 19
<212> TYPE: DNA
<213> ORGANISM: Homo sapiens
<220> FEATURE:
<221> NAME/KEY: misc_feature
<222> LOCATION: (1)...(1)
<223> OTHER INFORMATION: cytosine is labelled with FAM dye

<400> SEQUENCE: 95 ctgtattcc tcgcctgtcc                                                 19
```

```
<210> SEQ ID NO 96
<211> LENGTH: 23
<212> TYPE: DNA
<213> ORGANISM: Chlamydia trachomatis
<220> FEATURE:
<221> NAME/KEY: misc_feature
<222> LOCATION: (7) ... (7)
<223> OTHER INFORMATION: Fluorescent-labelled nucleotide Glen
      Fluorescein dT
<220> FEATURE:
<221> NAME/KEY: misc_feature
<222> LOCATION: (13) ... (13)
<223> OTHER INFORMATION: Fluorescent-labelled nucleotide Glen
      Fluorescein dT
<220> FEATURE:
<221> NAME/KEY: misc_feature
<222> LOCATION: (15) ... (15)
<223> OTHER INFORMATION: Fluorescent-labelled nucleotide Glen
      Fluorescein dT

<400> SEQUENCE: 96
caagccngca aangnatacc aag                                              23

<210> SEQ ID NO 97
<211> LENGTH: 23
<212> TYPE: DNA
<213> ORGANISM: Homo sapiens
<220> FEATURE:
<221> NAME/KEY: misc_feature
<222> LOCATION: (7) ... (7)
<223> OTHER INFORMATION: Fluorescent-labelled nucleotide Glen
      Fluorescein dT
<220> FEATURE:
<221> NAME/KEY: misc_feature
<222> LOCATION: (13) ... (13)
<223> OTHER INFORMATION: Fluorescent-labelled nucleotide Glen
      Fluorescein dT
<220> FEATURE:
<221> NAME/KEY: misc_feature
<222> LOCATION: (15) ... (15)
<223> OTHER INFORMATION: Fluorescent-labelled nucleotide Glen
      Fluorescein dT
<220> FEATURE:
<221> NAME/KEY: misc_feature
<222> LOCATION: (17) ... (17)
<223> OTHER INFORMATION: Fluorescent-labelled nucleotide Glen
      Fluorescein dT

<400> SEQUENCE: 97
caagccngca aangnanacc aag                                              23

<210> SEQ ID NO 98
<211> LENGTH: 142
<212> TYPE: DNA
<213> ORGANISM: Artificial Sequence
<220> FEATURE:
<223> OTHER INFORMATION: PCR template for Chlamydia mimic

<400> SEQUENCE: 98
aattccgcag ctgctgtaat cacccagtcg ataaatgtgt aagcatactt tgatgcattt      60
ggtttatttc ttggtataca tttacaggct tgattattct atttgatcta ccaagatagg     120
acatggctct acaacgaacc cg                                              142

<210> SEQ ID NO 99
<211> LENGTH: 25
<212> TYPE: DNA
<213> ORGANISM: Staphylococcus aureus (MRSA)
<220> FEATURE:
<221> NAME/KEY: misc_feature
<222> LOCATION: (6) ... (6)
```

```
<223> OTHER INFORMATION: Fluorescent-labelled nucleotide Glen
      Fluorescein dT
<220> FEATURE:
<221> NAME/KEY: misc_feature
<222> LOCATION: (15) ... (15)
<223> OTHER INFORMATION: Fluorescent-labelled nucleotide Glen
      Fluorescein dT

<400> SEQUENCE: 99
cgtagntact gcgtngtaag acgtc                                          25

<210> SEQ ID NO 100
<211> LENGTH: 25
<212> TYPE: DNA
<213> ORGANISM: Staphylococcus aureus (MRSA)

<400> SEQUENCE: 100
gacgtcttac aacgcagtaa ctacg                                          25

<210> SEQ ID NO 101
<211> LENGTH: 19
<212> TYPE: DNA
<213> ORGANISM: Homo sapiens
<220> FEATURE:
<221> NAME/KEY: misc_feature
<222> LOCATION: (15) ... (15)
<223> OTHER INFORMATION: Fluorescent-labelled nucleotide Glen
      Fluorescein dT

<400> SEQUENCE: 101
ctgtattcct cgccngtcc                                                 19

<210> SEQ ID NO 102
<211> LENGTH: 23
<212> TYPE: DNA
<213> ORGANISM: Chlamydia trachomatis
<220> FEATURE:
<221> NAME/KEY: misc_feature
<222> LOCATION: (7) ... (7)
<223> OTHER INFORMATION: Fluorescent-labelled nucleotide Glen
      Fluorescein dT
<220> FEATURE:
<221> NAME/KEY: misc_feature
<222> LOCATION: (13) ... (13)
<223> OTHER INFORMATION: Fluorescent-labelled nucleotide Glen
      Fluorescein dT
<220> FEATURE:
<221> NAME/KEY: misc_feature
<222> LOCATION: (17) ... (17)
<223> OTHER INFORMATION: Fluorescent-labelled nucleotide Glen
      Fluorescein dT

<400> SEQUENCE: 102
caagccngca aangtanacc aag                                            23

<210> SEQ ID NO 103
<211> LENGTH: 28
<212> TYPE: DNA
<213> ORGANISM: Chlamydia trachomatis

<400> SEQUENCE: 103
cttggtatac atttgcaggc ttgattac                                       28

<210> SEQ ID NO 104
<211> LENGTH: 28
<212> TYPE: DNA
<213> ORGANISM: Chlamydia trachomatis
<220> FEATURE:
<221> NAME/KEY: misc_feature
<222> LOCATION: (5) ... (5)
```

```
<223> OTHER INFORMATION: Fluorescent-labelled nucleotide Glen
      Fluorescein dT
<220> FEATURE:
<221> NAME/KEY: misc_feature
<222> LOCATION: (12) ... (12)
<223> OTHER INFORMATION: Fluorescent-labelled nucleotide Glen
      Fluorescein dT
<220> FEATURE:
<221> NAME/KEY: misc_feature
<222> LOCATION: (18) ... (18)
<223> OTHER INFORMATION: Fluorescent-labelled nucleotide Glen
      Fluorescein dT

<400> SEQUENCE: 104
gtaancaagc cngcaaangt ataccaag                                         28

<210> SEQ ID NO 105
<211> LENGTH: 23
<212> TYPE: DNA
<213> ORGANISM: Chlamydia trachomatis
<220> FEATURE:
<221> NAME/KEY: misc_feature
<222> LOCATION: (7) ... (7)
<223> OTHER INFORMATION: Fluorescent-labelled nucleotide Glen
      Fluorescein dT

<400> SEQUENCE: 105
caagccngca aatgtatacc aag                                              23

<210> SEQ ID NO 106
<211> LENGTH: 23
<212> TYPE: DNA
<213> ORGANISM: Chlamydia trachomatis
<220> FEATURE:
<221> NAME/KEY: misc_feature
<222> LOCATION: (17) ... (17)
<223> OTHER INFORMATION: Fluorescent-labelled nucleotide Glen
      Fluorescein dT

<400> SEQUENCE: 106
caagcctgca aatgtanacc aag                                              23

<210> SEQ ID NO 107
<211> LENGTH: 23
<212> TYPE: DNA
<213> ORGANISM: Chlamydia trachomatis
<220> FEATURE:
<221> NAME/KEY: misc_feature
<222> LOCATION: (13) ... (13)
<223> OTHER INFORMATION: Fluorescent-labelled nucleotide Glen
      Fluorescein dT
<220> FEATURE:
<221> NAME/KEY: misc_feature
<222> LOCATION: (17) ... (17)
<223> OTHER INFORMATION: Fluorescent-labelled nucleotide Glen
      Fluorescein dT

<400> SEQUENCE: 107
caagcctgca aangtanacc aag                                              23

<210> SEQ ID NO 108
<211> LENGTH: 23
<212> TYPE: DNA
<213> ORGANISM: Chlamydia trachomatis
<220> FEATURE:
<221> NAME/KEY: misc_feature
<222> LOCATION: (7) ... (7)
<223> OTHER INFORMATION: Fluorescent-labelled nucleotide Glen
      Fluorescein dT
<220> FEATURE:
<221> NAME/KEY: misc_feature
<222> LOCATION: (17) ... (17)
```

```
<223> OTHER INFORMATION: Fluorescent-labelled nucleotide Glen
      Fluorescein dT

<400> SEQUENCE: 108
caagccngca aatgtanacc aag                                            23

<210> SEQ ID NO 109
<211> LENGTH: 22
<212> TYPE: DNA
<213> ORGANISM: Homo sapiens
<220> FEATURE:
<221> NAME/KEY: misc_feature
<222> LOCATION: (4) ... (4)
<223> OTHER INFORMATION: Fluorescent-labelled nucleotide Glen
      Fluorescein dT
<220> FEATURE:
<221> NAME/KEY: misc_feature
<222> LOCATION: (16) ... (16)
<223> OTHER INFORMATION: Fluorescent-labelled nucleotide Glen
      Fluorescein dT

<400> SEQUENCE: 109
gtcngcggga gccganttca tc                                             22

<210> SEQ ID NO 110
<211> LENGTH: 22
<212> TYPE: DNA
<213> ORGANISM: Homo sapiens

<400> SEQUENCE: 110
gatgaaatcg gctcccgcag ac                                             22

<210> SEQ ID NO 111
<211> LENGTH: 22
<212> TYPE: DNA
<213> ORGANISM: Homo sapiens

<400> SEQUENCE: 111
gatgaaatcg actcccgcag ac                                             22

<210> SEQ ID NO 112
<211> LENGTH: 23
<212> TYPE: DNA
<213> ORGANISM: Homo sapiens
<220> FEATURE:
<221> NAME/KEY: misc_feature
<222> LOCATION: (7) ... (7)
<223> OTHER INFORMATION: Fluorescent-labelled nucleotide Glen
      Fluorescein dT
<220> FEATURE:
<221> NAME/KEY: misc_feature
<222> LOCATION: (16) ... (16)
<223> OTHER INFORMATION: Fluorescent-labelled nucleotide Glen
      Fluorescein dT

<400> SEQUENCE: 112
gaccagngaa gcaagngtct ttg                                            23

<210> SEQ ID NO 113
<211> LENGTH: 23
<212> TYPE: DNA
<213> ORGANISM: Homo sapiens

<400> SEQUENCE: 113
caaagacact tgcttcactg gtc                                            23

<210> SEQ ID NO 114
<211> LENGTH: 23
```

```
<212> TYPE: DNA
<213> ORGANISM: Homo sapiens

<400> SEQUENCE: 114
caaagacact ttcttcactg gtc                                         23

<210> SEQ ID NO 115
<211> LENGTH: 22
<212> TYPE: DNA
<213> ORGANISM: Homo sapiens
<220> FEATURE:
<221> NAME/KEY: misc_feature
<222> LOCATION: (5)...(5)
<223> OTHER INFORMATION: Fluorescent-labelled nucleotide Glen
      Fluorescein dT
<220> FEATURE:
<221> NAME/KEY: misc_feature
<222> LOCATION: (15)...(15)
<223> OTHER INFORMATION: Fluorescent-labelled nucleotide Glen
      Fluorescein dT

<400> SEQUENCE: 115
gcatngaggc tcgcngagag tc                                          22

<210> SEQ ID NO 116
<211> LENGTH: 22
<212> TYPE: DNA
<213> ORGANISM: Homo sapiens

<400> SEQUENCE: 116
gactctcagc gagcctcaat gc                                          22

<210> SEQ ID NO 117
<211> LENGTH: 22
<212> TYPE: DNA
<213> ORGANISM: Homo sapiens

<400> SEQUENCE: 117
gactctcagc aagcctcaat gc                                          22

<210> SEQ ID NO 118
<211> LENGTH: 20
<212> TYPE: DNA
<213> ORGANISM: Homo sapiens

<400> SEQUENCE: 118
ctgggctcct ggaaccaatc                                             20

<210> SEQ ID NO 119
<211> LENGTH: 21
<212> TYPE: DNA
<213> ORGANISM: Homo sapiens

<400> SEQUENCE: 119
gctgcccatg aatagcactg g                                           21

<210> SEQ ID NO 120
<211> LENGTH: 20
<212> TYPE: DNA
<213> ORGANISM: Homo sapiens

<400> SEQUENCE: 120
cccaaggagg agctgctgaa                                             20

<210> SEQ ID NO 121
<211> LENGTH: 20
```

```
<212> TYPE: DNA
<213> ORGANISM: Homo sapiens

<400> SEQUENCE: 121
ccattccggt ttggttctcc                                               20

<210> SEQ ID NO 122
<211> LENGTH: 23
<212> TYPE: DNA
<213> ORGANISM: Homo sapiens

<400> SEQUENCE: 122
ctgacctgaa gcacttgaag gag                                           23

<210> SEQ ID NO 123
<211> LENGTH: 25
<212> TYPE: DNA
<213> ORGANISM: Homo sapiens

<400> SEQUENCE: 123
gcggaagaat gtgtcagcct caaag                                         25

<210> SEQ ID NO 124
<211> LENGTH: 23
<212> TYPE: DNA
<213> ORGANISM: Homo sapiens
<220> FEATURE:
<221> NAME/KEY: misc_feature
<222> LOCATION: (11)...(11)
<223> OTHER INFORMATION: Fluorescent-labelled nucleotide C6 FAM dU

<400> SEQUENCE: 124
gagaggaatc nggtacttgg acc                                           23

<210> SEQ ID NO 125
<211> LENGTH: 19
<212> TYPE: DNA
<213> ORGANISM: Homo sapiens
<220> FEATURE:
<221> NAME/KEY: misc_feature
<222> LOCATION: (8)...(8)
<223> OTHER INFORMATION: Glen amino-dC labelled with FAM post-synthesis

<400> SEQUENCE: 125
ctgtattnct cgcctgtcc                                                19

<210> SEQ ID NO 126
<211> LENGTH: 28
<212> TYPE: DNA
<213> ORGANISM: Chlamydia trachomatis
<220> FEATURE:
<221> NAME/KEY: misc_feature
<222> LOCATION: (5)...(5)
<223> OTHER INFORMATION: Fluorescent-labelled nucleotide Glen
      Fluorescein dT
<220> FEATURE:
<221> NAME/KEY: misc_feature
<222> LOCATION: (12)...(12)
<223> OTHER INFORMATION: Fluorescent-labelled nucleotide Glen
      Fluorescein dT
<220> FEATURE:
<221> NAME/KEY: misc_feature
<222> LOCATION: (18)...(18)
<223> OTHER INFORMATION: Fluorescent-labelled nucleotide Glen
      Fluorescein dT
<220> FEATURE:
<221> NAME/KEY: misc_feature
<222> LOCATION: (22)...(22)
<223> OTHER INFORMATION: Fluorescent-labelled nucleotide Glen
      Fluorescein dT
```

<400> SEQUENCE: 126
gtaancaagc cngcaaangt anaccaag                                              28

<210> SEQ ID NO 127
<211> LENGTH: 19
<212> TYPE: DNA
<213> ORGANISM: Homo sapiens
<220> FEATURE:
<221> NAME/KEY: misc_feature
<222> LOCATION: (6)...(6)
<223> OTHER INFORMATION: Fluorescent-labelled nucleotide Glen
      Fluorescein dT
<220> FEATURE:
<221> NAME/KEY: misc_feature
<222> LOCATION: (10)...(10)
<223> OTHER INFORMATION: Fluorescent-labelled nucleotide Glen
      Fluorescein dT
<220> FEATURE:
<221> NAME/KEY: misc_feature
<222> LOCATION: (15)...(15)
<223> OTHER INFORMATION: Fluorescent-labelled nucleotide Glen
      Fluorescein dT

<400> SEQUENCE: 127
ctgtantccn cgccngtcc                                                        19

<210> SEQ ID NO 128
<211> LENGTH: 19
<212> TYPE: DNA
<213> ORGANISM: Homo sapiens
<220> FEATURE:
<221> NAME/KEY: misc_feature
<222> LOCATION: (10)...(10)
<223> OTHER INFORMATION: Fluorescent-labelled nucleotide Glen
      Fluorescein dT

<400> SEQUENCE: 128
ctgtattccn cgcctgtcc                                                        19

<210> SEQ ID NO 129
<211> LENGTH: 25
<212> TYPE: DNA
<213> ORGANISM: Artificial Sequence
<220> FEATURE:
<223> OTHER INFORMATION: MOD0 fluorophore-labelled oligonucleotide probe
<220> FEATURE:
<221> NAME/KEY: misc_feature
<222> LOCATION: (12)...(12)
<223> OTHER INFORMATION: Fluorescent-labelled nucleotide
      Glen Fluorescein dT
<220> FEATURE:
<221> NAME/KEY: misc_feature
<222> LOCATION: (13)...(13)
<223> OTHER INFORMATION: Fluorescent-labelled nucleotide Glen
      Fluorescein dT

<400> SEQUENCE: 129 gggggtttt tnntttttg ggggg                                                   25

<210> SEQ ID NO 130
<211> LENGTH: 25
<212> TYPE: DNA
<213> ORGANISM: Artificial Sequence
<220> FEATURE:
<223> OTHER INFORMATION: MOD1 fluorophore-labelled oligonucleotide probe
<220> FEATURE:
<221> NAME/KEY: misc_feature
<222> LOCATION: (12)...(12)
<223> OTHER INFORMATION: Fluorescent-labelled nucleotide Glen
      Fluorescein dT
<220> FEATURE:

```
<221> NAME/KEY: misc_feature
<222> LOCATION: (14)...(14)
<223> OTHER INFORMATION: Fluorescent-labelled nucleotide Glen
      Fluorescein dT

<400> SEQUENCE: 130 gggggtttt tntnttttg ggggg                                         25

<210> SEQ ID NO 131
<211> LENGTH: 25
<212> TYPE: DNA
<213> ORGANISM: Artificial Sequence
<220> FEATURE:
<223> OTHER INFORMATION: MOD2 fluorophore-labelled oligonucleotide probe
<220> FEATURE:
<221> NAME/KEY: misc_feature
<222> LOCATION: (11)...(11)
<223> OTHER INFORMATION: Fluorescent-labelled nucleotide Glen
      Fluorescein dT
<220> FEATURE:
<221> NAME/KEY: misc_feature
<222> LOCATION: (14)...(14)
<223> OTHER INFORMATION: Fluorescent-labelled nucleotide Glen
      Fluorescein dT

<400> SEQUENCE: 131 gggggtttt nttnttttg ggggg                                         25

<210> SEQ ID NO 132
<211> LENGTH: 25
<212> TYPE: DNA
<213> ORGANISM: Artificial Sequence
<220> FEATURE:
<223> OTHER INFORMATION: MOD3 fluorophore-labelled oligonucleotide probe
<220> FEATURE:
<221> NAME/KEY: misc_feature
<222> LOCATION: (11)...(11)
<223> OTHER INFORMATION: Fluorescent-labelled nucleotide Glen
      Fluorescein dT
<220> FEATURE:
<221> NAME/KEY: misc_feature
<222> LOCATION: (15)...(15)
<223> OTHER INFORMATION: Fluorescent-labelled nucleotide Glen
      Fluorescein dT

<400> SEQUENCE: 132 gggggtttt ntttntttg ggggg                                         25

<210> SEQ ID NO 133
<211> LENGTH: 25
<212> TYPE: DNA
<213> ORGANISM: Artificial Sequence
<220> FEATURE:
<223> OTHER INFORMATION: MOD4 fluorophore-labelled oligonucleotide probe
<220> FEATURE:
<221> NAME/KEY: misc_feature
<222> LOCATION: (10)...(10)
<223> OTHER INFORMATION: Fluorescent-labelled nucleotide Glen
      Fluorescein dT
<220> FEATURE:
<221> NAME/KEY: misc_feature
<222> LOCATION: (15)...(15)
<223> OTHER INFORMATION: Fluorescent-labelled nucleotide Glen
      Fluorescein dT

<400> SEQUENCE: 133 gggggttn ttttntttg ggggg                                          25

<210> SEQ ID NO 134
<211> LENGTH: 25
<212> TYPE: DNA
<213> ORGANISM: Artificial Sequence
```

```
<220> FEATURE:
<223> OTHER INFORMATION: MOD5 fluorophore-labelled oligonucleotide probe
<220> FEATURE:
<221> NAME/KEY: misc_feature
<222> LOCATION: (10) ... (10)
<223> OTHER INFORMATION: Fluorescent-labelled nucleotide Glen
      Fluorescein dT
<220> FEATURE:
<221> NAME/KEY: misc_feature
<222> LOCATION: (16) ... (16)
<223> OTHER INFORMATION: Fluorescent-labelled nucleotide Glen
      Fluorescein dT

<400> SEQUENCE: 134 gggggtttn tttttnttg ggggg                                            25

<210> SEQ ID NO 135
<211> LENGTH: 25
<212> TYPE: DNA
<213> ORGANISM: Artificial Sequence
<220> FEATURE:
<223> OTHER INFORMATION: MOD6 fluorophore-labelled oligonucleotide probe
<220> FEATURE:
<221> NAME/KEY: misc_feature
<222> LOCATION: (9) ... (9)
<223> OTHER INFORMATION: Fluorescent-labelled nucleotide Glen
      Fluorescein dT
<220> FEATURE:
<221> NAME/KEY: misc_feature
<222> LOCATION: (16) ... (16)
<223> OTHER INFORMATION: Fluorescent-labelled nucleotide Glen
      Fluorescein dT

<400> SEQUENCE: 135 gggggttnt tttttnttg ggggg                                            25

<210> SEQ ID NO 136
<211> LENGTH: 25
<212> TYPE: DNA
<213> ORGANISM: Artificial Sequence
<220> FEATURE:
<223> OTHER INFORMATION: MOD7 fluorophore-labelled oligonucleotide probe
<220> FEATURE:
<221> NAME/KEY: misc_feature
<222> LOCATION: (9) ... (9)
<223> OTHER INFORMATION: Fluorescent-labelled nucleotide Glen
      Fluorescein dT
<220> FEATURE:
<221> NAME/KEY: misc_feature
<222> LOCATION: (17) ... (17)
<223> OTHER INFORMATION: Fluorescent-labelled nucleotide Glen
      Fluorescein dT

<400> SEQUENCE: 136 gggggttnt tttttnttg ggggg                                            25

<210> SEQ ID NO 137
<211> LENGTH: 25
<212> TYPE: DNA
<213> ORGANISM: Artificial Sequence
<220> FEATURE:
<223> OTHER INFORMATION: MOD8 fluorophore-labelled oligonucleotide probe
<220> FEATURE:
<221> NAME/KEY: misc_feature
<222> LOCATION: (8) ... (8)
<223> OTHER INFORMATION: Fluorescent-labelled nucleotide Glen
      Fluorescein dT
<220> FEATURE:
<221> NAME/KEY: misc_feature
<222> LOCATION: (17) ... (17)
<223> OTHER INFORMATION: Fluorescent-labelled nucleotide Glen
      Fluorescein dT

<400> SEQUENCE: 137
```

```
gggggggtntt tttttttnttg ggggg                                      25
```

<210> SEQ ID NO 138
<211> LENGTH: 25
<212> TYPE: DNA
<213> ORGANISM: Artificial Sequence
<220> FEATURE:
<223> OTHER INFORMATION: MOD9 fluorophore-labelled oligonucleotide probe
<220> FEATURE:
<221> NAME/KEY: misc_feature
<222> LOCATION: (8)...(8)
<223> OTHER INFORMATION: Fluorescent-labelled nucleotide Glen
      Fluorescein dT
<220> FEATURE:
<221> NAME/KEY: misc_feature
<222> LOCATION: (18)...(18)
<223> OTHER INFORMATION: Fluorescent-labelled nucleotide Glen
      Fluorescein dT

<400> SEQUENCE: 138

```
ggggggtntt tttttttntg ggggg                                        25
```

<210> SEQ ID NO 139
<211> LENGTH: 25
<212> TYPE: DNA
<213> ORGANISM: Artificial Sequence
<220> FEATURE:
<223> OTHER INFORMATION: MODRC reverse homologue oligonucleotide

<400> SEQUENCE: 139

```
cccccctttt tttttttttc ccccc                                        25
```

<210> SEQ ID NO 140
<211> LENGTH: 19
<212> TYPE: DNA
<213> ORGANISM: Artificial Sequence
<220> FEATURE:
<223> OTHER INFORMATION: Factor V oligonucleotide probe

<400> SEQUENCE: 140

```
ctgtattcct cgcctgtcc                                               19
```

<210> SEQ ID NO 141
<211> LENGTH: 25
<212> TYPE: DNA
<213> ORGANISM: Artificial Sequence
<220> FEATURE:
<223> OTHER INFORMATION: Factor V target sequence

<400> SEQUENCE: 141

```
cctggacagg cgaggaatac aggta                                        25
```

<210> SEQ ID NO 142
<211> LENGTH: 19
<212> TYPE: DNA
<213> ORGANISM: Artificial Sequence
<220> FEATURE:
<223> OTHER INFORMATION: ATD0638 fluorophore-labelled oligonucleotide
      probe
<220> FEATURE:
<221> NAME/KEY: misc_feature
<222> LOCATION: (6)...(6)
<223> OTHER INFORMATION: FAM dG

<400> SEQUENCE: 142

```
ggacangcaa ggtatacag                                               19
```

<210> SEQ ID NO 143

```
<211> LENGTH: 19
<212> TYPE: DNA
<213> ORGANISM: Artificial Sequence
<220> FEATURE:
<223> OTHER INFORMATION: ATD0639 fluorophore-labelled oligonucleotide
      probe
<220> FEATURE:
<221> NAME/KEY: misc_feature
<222> LOCATION: (6) ... (6)
<223> OTHER INFORMATION: FAM dG
<220> FEATURE:
<221> NAME/KEY: misc_feature
<222> LOCATION: (12) ... (12)
<223> OTHER INFORMATION: FAM dG

<400> SEQUENCE: 143
ggacangcaa gntatacag                                                  19

<210> SEQ ID NO 144
<211> LENGTH: 19
<212> TYPE: DNA
<213> ORGANISM: Homo sapiens
<220> FEATURE:
<221> NAME/KEY: misc_feature
<222> LOCATION: (6) ... (6)
<223> OTHER INFORMATION: Fluorophore-lablelled nucleotide MeNPOCOH dT +
      TAMRA
<220> FEATURE:
<221> NAME/KEY: misc_feature
<222> LOCATION: (15) ... (15)
<223> OTHER INFORMATION: Fluorophore-lablelled nucleotide MeNPOCOH dT +
      TAMRA

<400> SEQUENCE: 144
ctgtantcct cgccngtcc                                                  19

<210> SEQ ID NO 145
<211> LENGTH: 19
<212> TYPE: DNA
<213> ORGANISM: Homo sapiens
<220> FEATURE:
<221> NAME/KEY: misc_feature
<222> LOCATION: (6) ... (6)
<223> OTHER INFORMATION: Fluorophore-lablelled nucleotide MeNPOCOH dT +
      ROX
<220> FEATURE:
<221> NAME/KEY: misc_feature
<222> LOCATION: (15) ... (15)
<223> OTHER INFORMATION: Fluorophore-lablelled nucleotide MeNPOCOH dT +
      ROX

<400> SEQUENCE: 145
ctgtantcct cgccngtcc                                                  19

<210> SEQ ID NO 146
<211> LENGTH: 19
<212> TYPE: DNA
<213> ORGANISM: Homo sapiens
<220> FEATURE:
<221> NAME/KEY: misc_feature
<222> LOCATION: (6) ... (6)
<223> OTHER INFORMATION: Fluorophore-lablelled nucleotide MeNPOCOH dT +
      Cy5
<220> FEATURE:
<221> NAME/KEY: misc_feature
<222> LOCATION: (15) ... (15)
<223> OTHER INFORMATION: Fluorophore-lablelled nucleotide MeNPOCOH dT +
      Cy5

<400> SEQUENCE: 146
ctgtantcct cgccngtcc                                                  19
```

```
<210> SEQ ID NO 147
<211> LENGTH: 19
<212> TYPE: DNA
<213> ORGANISM: Homo sapiens
<220> FEATURE:
<221> NAME/KEY: misc_feature
<222> LOCATION: (6) ... (6)
<223> OTHER INFORMATION: Fluorescein dT
<220> FEATURE:
<221> NAME/KEY: misc_feature
<222> LOCATION: (15) ... (15)
<223> OTHER INFORMATION: MeNPOCOH dT + Cy5

<400> SEQUENCE: 147
ctgtantcct cgccngtcc                                                     19
```

OLIGONUCLEOTIDES

The present application is a U.S. national phase application of International Application No. PCT/GB2006/002719 filed Jul. 20, 2006 and claims priority to United Kingdom Patent Application No. 0514889.5 filed Jul. 20, 2005. The contents of both applications are expressly incorporated herein by reference in their entireties.

The present invention relates to oligonucleotides, in particular to fluorescently labelled oligonucleotides for use as hybridisation probes.

A multitude of technologies for detecting specific DNA sequences and scoring known single nucleotide polymorphisms are known. Several of these detection methods utilise hybridisation of fluorescent probes and rely on the transfer of energy between donor and acceptor moieties.

Homogenous Polymerase Chain Reaction (PCR) is a method that couples amplification and detection processes. The benefits of homogeneous PCR over traditional methods, such as target amplification followed by gel electrophoresis, are a reduction in test duration, hands-on-time and the potential for cross-contamination. Fluorescent probes are employed with real-time PCR instruments, such as the LightCycler (Roche), ABI PRISM 7700 & 7900 (Applied Biosystems), Smartcycler (Cepheid), Rotogene (Corbett Research), MX4000 (Stratagene), SynChron (Biogene) and iCycler (BioRad), to detect and identify amplified products during (real-time) or post (end-point) amplification. Examples of probe based technologies include, molecular beacons (Tyagi et al, 1996), the 5'-exonuclease assay (U.S. Pat. No. 5,691,146), hybridisation probes (U.S. Pat. No. 6,174,670), Scorpion primers (Whitcombe et al, 1999), and ResonSense (Lee et al, 2002). Fluorescent probes are typically in a quenched or unexcited state until hybridisation to a target sequence results in dequenching, such as by conformational changes or probe degradation, or excitation as a result of probe interactions. These probe systems rely on the transfer of energy between donor (e.g. fluorophore) and acceptor (e.g. quencher or secondary fluorophore) moieties. The energy absorbed by a fluorophore may be transferred to a quencher or an acceptor fluorophore and released as heat or emitted as light of a different wavelength. Quenching of fluorescent signal may occur by Fluorescence Resonance Energy Transfer (FRET) or non-FRET mechanisms. FRET quenching requires a spectral overlap between the donor and acceptor, where the efficiency of quenching is related to the distance between the two moieties. Non-FRET quenching occurs through short-range 'contacts' between fluorophore and quencher, requiring no spectral overlap between moieties.

The 5'-exonuclease (TaqMan™) assay uses FRET quenching to detect the PCR amplified target DNA. TaqMan probes are oligonucleotides that contain fluorophore and quencher moieties preferably located on 5' and 3' termini. Very little fluorescence is emitted from intact probe due to efficient intra-molecular quenching. However, during PCR amplification, the probe specifically hybridises to its target sequence and the 5'-3'-exonuclease activity of Taq polymerase cleaves the probe between fluorophore and quencher moieties. Enzymatic cleavage of TaqMan Probes spatially separates fluorophore and quencher components, causing significant increases in fluorescence emission correlated with target amplification. Careful design of TaqMan Probes allows discrimination of polymorphic targets, where only perfectly matched probes are degraded to generate increases in fluorescence signal. Since TaqMan Probes are digested during real-time PCR amplification, probes are not available for post-amplification sequence analysis.

Eclipse Probes are short linear oligonucleotides that have a minor groove binder (MGB) and a quencher moiety at the 5' end and a fluorophore attached to the 3' end. It is thought that the MGB prevents the exonuclease activity of Taq from cleaving the probe. Random coiling of the probe brings the fluorophore and quencher components into close proximity causing fluorescence quenching. Hybridisation to target sequences causes the probe to straighten out such that fluorophore and quencher moieties become spatially separated.

Molecular Beacons are single-stranded oligonucleotide probes that are non-fluorescent in isolation, but become fluorescent upon hybridisation to target sequences. Non-hybridised Molecular Beacons form stem-loop structures, possessing a fluorophore covalently linked to one end of the molecule and a quencher linked to the other, such that the hairpin of the beacon places the fluorophore moiety in close proximity with the quencher. When Molecular Beacons hybridise to target sequences, fluorophore and quencher moieties become spatially separated, such that the fluorophore is no longer quenched and the Molecular Beacon fluoresces. Molecular Beacons may be employed in real-time and end-point assays for sequence detection and SNP discrimination. The secondary structure of the Molecular Beacon conveys high specificity to the probe, allowing the identification of targets that differ by a single nucleotide. However, the Molecular Beacon's intra-molecular interaction potentially produces a source of competition for inter-molecular target hybridisation and, because the Molecular Beacon is an internal probe, it must compete with the amplicon's opposite strand for binding to the target sequence. The combination of both forms of competition may reduce Molecular Beacon hybridisation efficiency to some target molecules.

Scorpions are PCR primers with a stem-loop tail containing a fluorophore and a quencher (Whitcombe et al, 1999). The stem-loop structure brings fluorophore and quencher components into close proximity. The loop component of the Scorpion contains the probing sequence and target detection occurs by a highly efficient intra-molecular mechanism. During PCR, Scorpions are extended to form products that include the probe target sequence. The tail of the Scorpion folds over and enables hybridisation of probe and target sequences. Hybridisation of the probing sequence to the amplified target is thermodynamically favoured over the stem-loop structure and careful probe design enables discrimination of targets differing by as little as a single nucleotide. Probe hybridisation causes the stem-loop structure to dissociate such that fluorophore and quencher components become spatially separated and large increases in fluorescence emission are generated. The stem-loop tail is separated from the PCR primer sequence by a PCR stopper (e.g. BEG) that prevents the DNA polymerase from copying the stem-loop sequence of the Scorpion. Duplex Scorpions (Solinas et al, 2001) utilise two labelled oligonucleotides, one comprising the primer, fluorophore and probing sequence, and the other containing the quencher moiety. Again, extension of the duplex Scorpion enables the probing sequence to fold over and hybridise to the amplified target, thereby dissociating fluorophore and quencher oligonucleotides and increasing the amount of fluorescent signal emitted.

Hybridisation Probes are oligonucleotides that are singly labelled with fluorophore moieties. Two such oligonucleotides are required for each Hybridisation Probe assay, one labelled with a donor fluorophore and the other with an acceptor fluorophore. Fluorescein is commonly employed as the donor and Cy5, LC-RED 640 and LC-RED 705 are commonly used as acceptors. Excitation of the donor fluorophore produces an emission spectrum that overlaps with the absorption spectrum of the acceptor fluorophore. Hybridisation Probe pairs are designed to recognise adjacent nucleotide sequences within target molecules. In isolation, the acceptor oligonucleotide is not excited and does not generate a fluorescent signal. However, during hybridisation to polynucleotide target sequences, the donor and acceptor probes are brought into close proximity, allowing fluorescence resonance energy transfer from the donor to the acceptor. Fluorescent signal from the acceptor fluorophore is only emitted when both probes are hybridised to the target molecule. When incorporated into PCR reactions, fluorescence from the acceptor probe is monitored once per cycle of amplification, to facilitate real-time measurement of product accumulation, where the amount of fluorescence emitted by the acceptor is proportional to the quantity of target synthesised. Careful design of probes and assay conditions permits discrimination of closely related targets by real-time PCR. Furthermore, pairs of Hybridisation Probes may be employed to discriminate alleles by melt peak analysis and Tm determination. Homozygous samples may be identified by the generation of specific peaks during melting curve analysis and heterozygous samples may be identified by the presence of two peaks within a single melting trace.

ResonSense Probes are single-labelled oligonucleotides that bind to target sequences between the positions of primer pairs. ResonSense Probes do not yield detectable signal in isolation or the absence of target sequence. Instead, DNA intercalaters, such as SYBR Gold, are included to excite the ResonSense Probes. The DNA intercalater binds to duplex DNA and, when excited by the real-time instrument, transfers the energy to the fluorophore of the ResonSense Probe (Lee et al, 2002).

The above probe technologies utilise FRET and quencher labels to detect and discriminate polynucleotide sequences. However, the alternative Light-up Probe (Svanvik et al, 2000) system does not require quencher labels or FRET transfer between donor and acceptor moieties to detect and discriminate DNA sequences. These Light-up Probes comprise a sequence recognising oligonucleotide, composed of peptide nucleic acid (PNA), and a single fluorescent reporter group, where the reporter is typically a derivative of the asymmetric cyanine dye thiazole orange and carries a positive charge. The fluorescent dye component of Light-up Probes is attached to the terminus of the oligonucleotide molecule. When single-stranded, probes emit significantly lower levels of fluorescence than when hybridised to complementary nucleic acid sequences. In single-stranded probes, fluorophores are free and excited energy may be released in the form of movement or heat, such that probes do not fluoresce significantly. Upon hybridisation, the positively charged fluorophore inserts between the bases of DNA and becomes 'locked' into position as a result of the charge interaction, such that excited energy may only be released as light. By measuring the quantity of fluorescence emission, Light-up Probes may be employed to detect nucleic acid sequences and differentiate between targets differing by a single position.

Several other probe technologies have also been described that do not require the attachment of quencher moieties to enable target detection and identification. The emission of many fluorophores has been reported to change through their interaction with nucleobases (Siedel et al, 1996, Knemeyer et al, 2000, Lee et al, 1994, Crockett & Wittwer 2001, Nazerenko et al, 2002). Interaction of fluorophores with DNA has also been reported to affect the wavelength of fluorescence emission. The greatest effect on fluorescence has been attributed to guanine, which is an efficient electron donor. Quenching is thought to arise from electron transfer of the guanine nucleobase to the fluorescent dye. The degree of quenching is reported to depend on the proximity of fluorophores to guanines in probe and target strands (Xu et al, 1994, Hawkins et al, 1997, Norlund et al, 1989). The magnitude and direction of emission change in fluorescent labelled probes is reported to be dependent upon the location of guanine residues in probe and target sequences. LUX Primers (Invitrogen) employ hairpin structures to quench fluorophores attached close to the 3' end of the hairpin (Nazerenko et al, 2002). The hairpin structure of the LUX Primers frequently brings fluorophore moieties into close proximity with a region of G's, thereby quenching fluorescence. When the primer becomes incorporated into double-stranded PCR product, the hairpin structure dissociates causing the fluorophore to become dequenched. The presence of guanine residues in proximity to the label is reported to affect the functionality of LUX Primers. LUX Primers yield fluorescent signal when incorporated into any double-stranded molecule and will, therefore, detect non-specific amplification products and primer-dimers.

GenePin Probes (Atto-tec GmbH) or Smart Probes (Knemeyer et al, 2000, Heinlein et al, 2003)) are stem-loop structures similar to Molecular Beacons. The loop is the probing component and the stem is employed to quench fluorescence in the single-stranded state (WO 01/36668). The fluorophore of GenePin Probes is attached to the poly(C) component of the stem and fluorescence is quenched efficiently by the complementary poly(G) stem component. Upon target hybridisation, the poly(C) and poly(G) components become separated, the affect of guanine quenching is removed and the level of fluorescence emission increases.

Simple Probes are single-labelled oligonucleotides that exhibit changes in fluorescence emission upon target hybridisation (U.S. Pat. No. 6,635,427). Fluorophores are typically terminally attached, where 5' labelled probes also preferably include a 3' phosphate. The magnitude and direction of fluorescence change in Simple Probes is dependent upon the probe DNA sequence flanking the position of fluorophore attachment and the target DNA sequence that the fluorophore interacts with upon hybridisation. Fluorescence quenching of Simple Probes has been reported upon hybridisation when fluorophores are brought into proximity with deoxyguanosine nucleotides in the target strand (Crockett & Wittwer 2001). In contrast fluorescence enhancement has been reported when terminal fluorophores, attached to or near G residues, are hybridised to complementary target sequences (U.S. Pat. No. 6,635,427). In a specific example, where the fluorophore replaced an internal base ("virtual nucleotide"), the fluorescence of a Simple Probe has been demonstrated to be both enhanced and quenched upon target hybridisation, when the fluorophore was brought into opposition with A and G nucleotides respectively in polymorphic target alleles. Heterozygous samples did not exhibit a significant increase or decrease in fluorescence upon probe/target hybridisation.

Hybridisation beacons (also called HyBeacons®) are internally labelled oligonucleotides that emit greater amounts of fluorescence when hybridised to target sequences than when in the single-stranded state (WO 01/73118). HyBeacons do not require a quencher moiety for fluorescence signal generation, and do not rely on probe secondary structures, enzymatic cleavage or FRET to another fluorophore. In the absence of a quencher label, the reported quenching properties of DNA are responsible for the alteration in fluorescence emission upon hybridisation. Unlike the other single-labelled probe technologies described above, the direction of fluorescence change is not affected by the nucleotide sequence of probe and target strands.

The listing or discussion of a prior-published document in this specification should not necessarily be taken as an acknowledgement that the document is part of the state of the art or is common general knowledge.

The inventors have now found that, surprisingly, oligonucleotides with multiple internal fluorophores, preferably at defined spacings from each other, give unexpectedly large fluorescent signals on binding a target polynucleotide sequence when compared to otherwise equivalent single-labelled versions.

A first aspect of the invention provides a single stranded oligonucleotide having substantially no secondary structure and formed of nucleotide residues wherein two or more internal nucleotide residues are labelled with a fluorophore without an associated quencher.

As is discussed in detail below, the oligonucleotides of the invention are particularly useful as hybridization probes.

The oligonucleotides of the invention, like the HyBeacons® described in WO 01/73118, do not rely on oligonucleotide secondary structures, enzyme action or quencher moieties attached to oligonucleotide in order to be effective as readily detectable hybridisation probes. Interaction between these oligonucleotides and their target sequences (as discussed below) generate significant alterations in fluorescence emission that enable reliable target detection. Variations in probe stability enable discrimination of targets differing by as little as a single nucleotide through the measurement of duplex melting temperature as discussed in more detail below.

Contrary to the sequence dependent data presented in U.S. Pat. No. 6,635,427, which suggests that fluorophores attached to oligonucleotides would be expected to be quenched upon probe/target hybridisation due to fluorophores being flanked by C residues and target strands having an abundance of G residues in the region of the fluorophore, the oligonucleotides of the invention exhibit enhanced levels of fluorescence when hybridised to full complementary and (partially) mismatched (ie partially complementary) target sequences, irrespective of the probe and target sequences.

Data demonstrates that the fluorophores of the oligonucleotides of the invention interact with the single-stranded oligonucleotide itself, but not with duplex DNA in the hybrid formed upon hybridisation. Therefore, while the sequence of the probe may affect the magnitude of fluorescence change, probes do not become quenched upon hybridisation. Even when fluorophore-labelled bases of the oligonucleotides of the invention are brought into proximity with a G rich target region upon hybridisation, dequenching and positive melt peaks (−dF/dT yields positive value) are observed as demonstrated herein, particularly with oligonucleotide probes where the directly fluorophore labelled nucleotide residues are separated by two or more unlabelled nucleotide residues. The sequence independence of the oligonucleotides of the invention is in contrast to that reported by Nazerenko et al, (2002b), where internal fluorescein dT emission was enhanced or quenched upon hybridisation dependent upon the location of the fluorophore within the probe and the proximity of guanines to the fluorophore. It was reported that at least one guanine base was required within four nucleotides of the label to enable fluorescence enhancement upon hybridisation.

As with the HyBeacons® of WO 01/73118, the multiple-labelled oligonucleotides of the invention described herein yield increased levels of fluorescence enhancement irrespective of probe and target sequences and do not require guanines at defined locations to facilitate fluorescence enhancement upon target hybridisation. Although not being bound by theory, it is believed that the fluorophores attached to the oligonucleotides of the invention interact with probe (oligonucleotide) DNA when single-stranded (for example, by being buried in a single-stranded hydrophobic pocket) thereby causing fluorescence quenching (eg by a base stack causing collisional quenching). However, it is believed that fluorophores do not interact with duplex DNA when probes are hybridised to a target, such that the fluorophores attached to the oligonucleotides of the invention project into solution and exhibit elevated levels of emission, where such increases are independent of the target sequence. Molecular and computational modelling described in Marks et al (2005), incorporated herein by reference, is relevant to this point.

By "single stranded oligonucleotide having substantially no secondary structure" we include the meaning that the oligonucleotide does not have a sequence whereby there are substantial parts which are the inverse complement of each other which allow for intramolecular base pairing. By "substantial parts" we mean four or more consecutive nucleotide residues. In particular, unlike prior art oligonucleotide probes such as Molecular Beacons, Scorpions, LUX and Smart probes which are designed to contain substantial regions of inverse complementarity, the probes of the invention are typically designed to avoid such inverse complementarity. The oligonucleotide probes of the invention only employ the inverse complement of the target and do not include additional sequences to generate secondary structure.

Potential secondary structure of an oligonucleotide may be predicted using nucleic acid folding software such as Mfold (Zucker (2003)). The stability of secondary structure is frequently represented by its free energy ($\Delta G$) ie the energy required to break the secondary structure, where large negative $\Delta G$ values indicate stable structures. The probes of the invention typically possess positive or small negative $\Delta G$ values, preferably less negative than −2 kcal/mol and more preferably less negative than −1 kcal/mol. Probe technologies that rely on secondary structure, such as Scorpions, typically exhibit much greater negative $\Delta G$ values. The Scorpion probes described by Thelwell et al (2000) possess $\Delta G$ values ranging from −7.7 kcal/mol to −12.2 kcal/mol.

Secondary structure arises when one region of an oligonucleotide hybridises with another e.g. forming a loop (as in conventional Molecular Beacons) which decreases the efficiency of the oligonucleotide hybridising with its target. In the oligonucleotides of the invention there is substantially no tendency for one region of the oligonucleotide to hybridise with another, and this can be assessed, for example, using the Mfold software mentioned above.

Fluorescent groups (fluorophores) are attached to internal bases in the oligonucleotide of the invention, as opposed to 5' or 3' termini, and are believed to be quenched to a greater extent when single-stranded than when in the duplex (ie upon hybridisation to the target), as the DNA bases are proposed to be able to stack on the fluorophore when they are not forming base pairs. In the single-stranded state, the fluorophore may be sandwiched between two DNA bases forming a stable hydrophobic structure. This structure will open up upon duplex formation as the nucleotides participate in base pairing.

With terminal labels, base stacking may still only occur on one side of the fluorophore on hybridisation. When the oligonucleotides of the invention hybridise, the fluorophore will not be positioned between DNA bases, but is able to extend unhindered from the base. Terminal labelled probes such as Simple Probes will become quenched upon duplex formation if the fluorophore is in closer proximity to more guanines in the duplex than in the single-stranded state. However, if terminal labels are attached to the probe in a region of high guanine abundance, fluorescence will be enhanced upon duplex formation (U.S. Pat. No. 6,635,427). This sequence dependence of fluorescence quenching and enhancement, according to the location and abundance of guanines in the probe and target strand, is not observed in the oligonucleotides of the invention.

All DNA bases are able to quench fluorescence to some extent, where G has the greatest such ability. For the avoidance of doubt, the term "associated quencher" does not include DNA bases which form part of the oligonucleotide. Fluorophores on the oligonucleotides of the invention will interact with the bases of single-stranded probes such that fluorescence is quenched. Since fluorophores are expected to project into solution upon target hybridisation and not interact with duplex DNA, the sequence of the target may not affect the direction of fluorescence change, i.e. guanines in the target may not quench fluorescence upon hybridisation. Therefore, the oligonucleotides of the invention exhibit increased levels of fluorescence when hybridised to target sequences. Gs may modulate fluorescence strength but all dequench significantly on hybridisation. Fluorescence from the internally attached fluorophores of the oligonucleotides of the invention is always enhanced upon duplex formation irrespective of the location and abundance of guanines in the probe and target strand.

The dual and multiple-labelled oligonucleotides of the invention emit significantly greater amounts of fluorescence when hybridised to complementary nucleic acid sequences compared with the single-stranded (non-hybridised) conformation despite the absence of a quencher component although simple spacing constraints as disclosed herein are typically followed in order to avoid adverse interactions leading to reduced peak heights or negative peaks as shown in FIG. 11.

The signal-to-noise ratio is the ratio of the signal intensity of a double-stranded hybrid comprising an oligonucleotide of the invention to the signal intensity of the single-stranded probe and is preferably as large as possible, e.g. 2 or more. Signal-to-noise ratios in the oligonucleotides of the invention are significant and usefully greater than 1 despite the absence of associated quencher moieties. It is believed that fluorophore moieties emit significantly more fluorescent signal when probes are hybridised to target molecules than when in the single-stranded state due to some form of interaction with DNA sequences. The dual or multiple-labelled oligonucleotide probes of the invention possess ratios that are greater than expected from single-labelled oligonucleotides of identical sequence.

Fluorescence enhancement occurs upon target hybridisation when fluorophore-labelled residues are placed in all sequence environments. Placing fluorophore-labelled residues adjacent to G's may result in the highest levels of fluorescence enhancement in the duplex state. However, fluorescence enhancement upon target hybridisation will also occur when fluorophore-labelled residues are located within regions of high C abundance. In one embodiment of this invention, the residues in the target strand are not responsible for either quenching or enhancing probe fluorescence upon hybridisation. The nature of the interaction of the fluorophore with the oligonucleotide differs between free and hybridised oligonucleotide so that the oligonucleotides of the invention exhibit higher levels of fluorescence emission when in duplexes than when single-stranded demonstrating that there are no apparent sequence constraints for functionality, although the sequence can affect the magnitude of fluorescence enhancement.

Typically, the oligonucleotide has 2 or 3 or 4 or 5 or 6 or 7 or 8 or 9 or 10 internal residues labelled with a fluorophore. The number may depend on the length of the oligonucleotide. Typically up to about one-third of the internal residues are labelled with a fluorophore, but it may be fewer.

The length of the oligonucleotide of the invention is preferably such that it is suitable for hybridising with a complementary polynucleotide target, to provide a stable hybrid whose melting temperature depends on the exact sequence of the target. Oligonucleotides containing less than 15 nucleotide residues in many cases do not form sufficiently stable hybrids, particularly where the two hybridising sequences are not fully complementary, although they can be used in some circumstances. Oligonucleotides, which are longer than about 30 nucleotide residues may form hybrids whose melting temperature is relatively insensitive to the possible presence of a single nucleotide mismatch, although they can be used in some circumstances.

Typically, the oligonucleotide is from 10 to 50 nucleotide residues in length, preferably from 15 to 30 nucleotide residues in length. Thus, typically, the oligonucleotide is from 10 or 11 or 12 or 13 or 14 or 15 nucleotide residues in length up to (and including) 25 or 26 or 27 or 28 or 29 or 30. Thus, the invention includes oligonucleotides within any of the size ranges mentioned.

An oligonucleotide within the size range from 15 to 30 nucleotides may have up to around 10 of its internal nucleotide residues labelled with a fluorophore, but conveniently an oligonucleotide in this size range has 2 or 3 or 4 or 5 of its internal residues labelled with a fluorophore.

It is preferred if at least two (or the two as the case may be) of the nucleotide residues labelled with a fluorophore are separated by at least two unlabelled nucleotide residues. Typically, there are 2 or 3 or 4 or 5 or 6 unlabelled nucleotide residues that separate the labelled nucleotide residues. It is particularly preferred if two unlabelled residues separate the labelled residues. It is also particularly preferred if all of the labelled nucleotide residues are separated by at least two unlabelled nucleotide residues. Preferably, the fluorophores are spaced such that direct 'contact' quenching between the fluorophores is avoided. Contact quenching arises from physical contact of fluorophores and is typically avoided by physical separation (ie at least 2 nucleotide residues between fluorophore-labelled bases).

Nucleotide residues are usually derived from the naturally occurring nucleosides A, C, G, T and U. However, nucleotide analogues may be used at one or more locations of the oligonucleotide of the invention, such nucleotide analogues being modified e.g. in the base portion and/or the sugar portion and/or the phosphate link. Base modifications, such as propynyl dU (dT-analogue) and 2-amino dA (dA analogue), generally alter the hybridisation properties and may make the use of oligonucleotides having less than 15 nucleotide residues attractive. In the case of propynyl dU-containing oligonucleotides, they be around 10 residues in length depending on the melting temperature with the target sequence required.

Alternatively, oligonucleotides composed of or comprising peptide nucleic acid (PNA), locked nucleic acid (LNA), 2'-O-methyl RNA, phosphoramidite DNA, phosphorothioate DNA, methyl phosphonate DNA or phosphotriester DNA may be employed to form chemically or enzymatically more stable interactions with target sequences.

It is preferred if the same fluorophore is used throughout the oligonucleotide of the invention. Any fluorophore that can be attached to a nucleotide residue may be used, provided that it does not prevent the oligonucleotide from hybridising to its target sequence.

Suitable fluorophores include fluorescein-based fluorophores such as FAM (6-Carboxyfluorescein), TET (Tetrachlorofluorescein), HEX (hexachlorofluorescein); rhodamine-based fluorophores such as ROX (6-Carboxy-X-Rhodamine) and TAMRA (6-Carboxytetramethylrhodamine); the Cy family of dyes, especially Cy3 and Cy5, all available from Glen Research, 22825 Davis Drive, Sterling, Va. 20164, USA.

Other fluorescein dyes, for example those with different emission spectra may be used, such as NED and JOE. Other fluorophores may also be used, such as those in the Alexa, Atto, Dyomics, Dyomics Megastokes and Thilyte dye families as detailed in Tables 9 to 15 below.

In a preferred embodiment of the invention, the oligonucleotides are labelled at the 5-position of internal uracil/thymine bases using C6 FAM dU (available from University of Southampton, UK) or Fluorescein dT (available from Glen Research, Sterling, Va.) respectively (in this context, the structure of dT and dU are identical and the terms therefore interchangeable). FMOC-protected phosphoramidites may be incorporated at internal T positions within oligonucleotides and can be used as a point of attachment for a variety of fluorescent dyes, including but not limited to FAM, TET, HEX, ROX, TAMRA, Cy3 and Cy5, all available from Glen Research After oligonucleotide synthesis, the FMOC group may be removed from the 2'-protected uridine and a fluorophore phosphoramidite, such as a suitably protected 6-carboxyfluorescein phosphoramidite, may be coupled to the free 2'-hydroxy group. In yet another embodiment, oligonucleotides may be labelled at internal A, C or G positions, where labelled nucleotides are either incorporated as phosphoramidites during solid phase oligonucleotide synthesis or fluorophores attached post oligonucleotide synthesis using protected phosphoramidites (eg 8-aminoalkyl-dA, 7-aminoalkyl 7-deaza-dA, N(4)-aminoalkyl dC and 5-aminoalkyl-dC).

Although typically the same fluorophore is used throughout the oligonucleotide of the invention, it may be advantageous to use different fluorophores in the same oligonucleotide. For example, as discussed in more detail in the examples, the presence of both ROX and FAM in the same oligonucleotide is advantageous. It is particularly preferred if the oligonucleotide contains two fluorophores, one of which is ROX and the other FAM. The use of two or more different fluorophores in the same oligonucleotide may be particularly advantageous when the oligonucleotide is used in multiplexing.

It is preferred that the fluorophore does not intercalate into double-standard DNA. It is preferred that the fluorophore is not thiazole orange(TO).

Dual-labelled oligonucleotides of the invention may be expected to exhibit fluorescent signals and background noise that are double that observed with single-labelled probes, such that the signal-to-noise ratio is maintained (ie an additive effect would be expected). However, surprisingly, the signal-to-noise ratios of dual-labelled probes are larger than those observed with single-labelled probes of identical sequence. A similar unexpected increase in the signal-to-noise ratio is also observed with other multiple-labelled oligonucleotides of the invention.

Furthermore, as described in more detail in the Examples, dual, triple, quadruple and further multiple-labelled probes have been demonstrated to generate considerably larger melt peaks than would be expected from the cumulative effect of the individual single-labelled probes of identical nucleotide sequence if the effect was simply additive.

Typically, the oligonucleotide of the invention has a sequence complementary to a target polynucleotide sequence. Thus, the oligonucleotide is able to hybridise to the target polynucleotide sequence under appropriate conditions. Thus, unless the context indicates otherwise, by "complementary" we include the meaning that the oligonucleotide is able to hybridise to a target polynucleotide sequence. The oligonucleotide may be fully complementary to the target polynucleotide sequence (ie there is a perfect match in terms of base pairing between the oligonucleotide), or the oligonucleotide may be partially complementary to the target polynucleotide sequence (ie there are one or more mismatches between the oligonucleotide and the target polynucleotide sequence, but the oligonucleotide is still able to hybridise). Typically, when the oligonucleotide is partially complementary with the target polynucleotide, there are fewer than 5 mismatches, preferably 1 or 2 or 3 or 4 mismatches, more preferably one mismatch. Conveniently, the oligonucleotide has at least 70% sequence identity to the complement of its target, more preferably at least 80% or at least 85% or at least 90% or at least 95%. For example, for an oligonucleotide of 20 residues, there may be 6 or 4 or 3 or 2 or 1 mismatch with the target.

Typically, the target polynucleotide sequence is selected from the group consisting of the human genome including any gene therein or allele thereof, the mouse genome including any gene therein or allele thereof, and the genome of any infectious agent including any gene therein or allele thereof. Preferably, the oligonucleotide is one which has a sequence complementary to any one of the following human genes or an allele thereof:

| | |
|---|---|
| N-acetyltransferase 2 | X14672 |
| Factor V Leiden | AY364535 |
| Factor II | AF493953 |
| MTHFR | NM_005957 |
| Sickle cell anaemia | AY356351 |

The sheep PrP gene (NM_001009481) is also a preferred gene for analysis.

Also preferably the oligonucleotide is one which has a sequence complementary to the genome or any gene therein or allele thereof of the following infectious agents:

| | |
|---|---|
| *Chlamydia trachomatis* | X07547 |
| Adenovirus | AJ293905 |
| Influenza A | AY130766 |
| *Streptococcus pneumoniae* | X52474 |
| MRSA | AJ810121 |

As is described further in the Examples, the oligonucleotide may be one which has a sequence complementary to one allele of a gene. For example, it may complementary to a mutant allele of a gene which, in humans, may be associated with a particular genetic disease (eg cystic fibrosis), or it may be complementary to the wild-type allele. It is preferable that the sequence complementary to the nucleotide sequence difference of the given allele compared to another allele of the gene is located towards the middle of the oligonucleotide (eg within the middle half to one-third of nucleotide residues). This allows for a good discrimination in melting temperatures for a given such oligonucleotide (which may hybridise to both alleles but with different Tms).

In a preferred embodiment, the oligonucleotide according to the invention preferably has a sequence fully complementary to one allele of a known polynucleotide target having a known polymorphism, e.g. a point mutation or a single base insertion or deletion (SNP). The site of polymorphism is preferably, though not essentially, located centrally within the oligonucleotide probe. Alternatively, the oligonucleotide may be complementary to a known non-polymorphic polynucleotide sequence and may simply be used to detect that target, e.g. for rapid pathogen detection. Also, the oligonucleotide may be used to study potentially polymorphic targets with unknown and uncharacterised polymorphisms. The possibility is envisaged of mapping the position and/or nature of unknown polymorphisms by differential oligonucleotide hybridisation and differences in melt peak Tm. When the oligonucleotide of the invention is caused to hybridise with a polynucleotide target, all the above features contribute to the formation of a stable hybrid with an optimal melting temperature and a substantial difference in melting temperatures (ΔTM) between strands that are perfectly matched and strands which have a single or multiple positions of mismatch.

As discussed in more detail below, particularly when the oligonucleotide of the invention is used as probe of the production of a target polynucleotide sequence in a nucleic acid amplification reaction, the oligonucleotide is one in which the 3' nucleotide residue does not contain a 3' hydroxyl group. It is preferred that the oligonucleotide is one which is not able to act as a primer for a DNA polymerase, and is not capable of ligation by a DNA ligase. Conveniently, the 3' nucleotide residue is a 3' deoxy residue. Also conveniently, the 3' nucleotide residue may have a 3' phosphate, or other 3' groups which would prevent chain extension.

A further aspect of the invention provides an oligonucleotide of the invention immobilised on a solid support. The solid support may be any suitable solid support. Techniques and linkers for immobilising oligonucleotides using supports in forms that leave them free to hybridise with complementary targets in solution are well described in the literature.

A still further aspect of the invention provides an array of oligonucleotides of the invention. The array may comprise two or more individually addressable sites of oligonucleotide immobilised on a solid support. Typically, the array will contain at least 10, or at least 100, or at least 1000 such sites. Typically, the array comprises oligonucleotides with different sequences, typically each different site is associated with an oligonucleotide with a difference sequence. In a preferred embodiment the array is an array of oligonucleotide probes immobilised at spaced locations using a support, wherein the different oligonucleotide probes are different oligonucleotides according to this invention. Furthermore, the oligonucleotides of the invention may be employed to analyse DNA targets immobilised on or within a support, where distinct targets may be positioned at spaced locations on array type formats.

Methods of immobilising oligonucleotides and making arrays of oligonucleotides are well known in the art:

A yet still further aspect of the invention provides a method of investigating a target polynucleotide sequence in a sample containing polynucleotide sequences, the method comprising contacting the sample with an oligonucleotide of the invention which is able to hybridise to the target polynucleotide sequence, and determining whether hybridisation occurs.

The sample may be any suitable sample, and may be one which is known to contain the target polynucleotide sequence, or it may be one where it is not known that it contains the target polynucleotide sequence, and the purpose of the investigation is to determine whether it does or not.

Since the oligonucleotide is fluorescently labelled, and because there is an increase in fluorescence upon binding of the oligonucleotide to the target, conveniently an increase in fluorescence is used to determine whether hybridisation has occurred between the oligonucleotide and the target polynucleotide sequence.

It will be appreciated that, under given conditions, the oligonucleotide is able to hybridise to its target at certain temperatures. As is discussed in more detail below, it may be desirable to vary the temperature of the hybridisation and detect fluorescence at different temperatures in order to investigate the target polynucleotide sequence. Thus, in a preferred embodiment of the invention the method is performed at a predetermined temperature, or over a range of temperatures, near the melting point (Tm) of the hybrid formed between the target polynucleotide sequence and the said oligonucleotide. Tms are typically determined by melt curve analysis where 50% of the probe is hybridised to target sequence and 50% is dissociated and free in solution.

The oligonucleotide may be fully complementary to the target polynucleotide sequence, and that oligonucleotide will have a characteristic Tm under given-hybridisation conditions. Alternatively, the oligonucleotide may not fully complementary to the target polynucleotide sequence, but nevertheless is able to hybridise to it (it is partially complementary), and that oligonucleotide will have a characteristic (but almost certainly different) Tm.

The method of the invention is particularly suited to the analysis of polymorphisms of a gene and so in one embodiment the target polynucleotide sequence investigated is one or more alleles of a gene. An (or the) oligonucleotide used in the method is conveniently one which is able to hybridise to more than one allele of the gene, and typically has different Tms under given hybridisation condition with respect to the different alleles.

The method may used to detect the presence of the target sequence, for example in a sample in which it is not known whether it is present. The method may also be used to identify the target sequence or it may be used to quantitate the amount of the target polynucleotide sequence in the sample. Typically, the increase in fluorescence upon binding of the oligonucleotide to the target polynucleotide is used for this.

It is particularly convenient if the sample contains polynucleotide sequences produced by amplification since often an initial source of biological material (such as saliva, a mouth scrape, small quantities of dried blood etc) contains only a small amount of nucleic acid that may contain the target polynucleotide.

Suitably, the polynucleotide sequences are produced by any one or more of polymerase chain reaction (PCR, including asymmetric PCR amplification), reverse transcription PCR (RT-PCR), ligase chain reaction (LCR), strand displacement amplification (SDA), transcription mediated amplification (TMA), rolling circle amplification (RCA) or nucleic acid sequence based amplification (NASBA).

In a preferred embodiment, the amplification of the polynucleotide sequences in the sample is performed in the presence of the oligonucleotide which is able to hybridise to the target polynucleotide sequence. In this embodiment, it is particularly preferred if the 3' nucleotide residue of the oligonucleotide does not contain a 3' hydroxyl. It is particularly preferred if the oligonucleotide of the invention present in the reaction is not capable of chain extension by a DNA polymerase and not capable of ligation by DNA ligase. In this embodiment it is also preferred if observation of fluorescence is made during the amplification of the polynucleotide sequences in the sample.

There may be no need to extract nucleic acid from the biological source prior to amplification, since the process of amplification may be capable of such extraction. Thus, for example, the polynucleotide sequences in the sample may be produced by amplification from a biological source such as saliva without prior nucleic acid extraction.

The invention provides a method of investigating a polynucleotide target having a known polymorphism, which method comprises providing an oligonucleotide probe comprising fluorophore-labelled nucleotide residues. The polynucleotide target is incubated with the oligonucleotide probe to faun a hybrid, the oligonucleotide probe exhibiting a higher level of fluorescence when in the form of the hybrid than when in single-stranded form. The level of fluorescence emitted by the oligonucleotide probe is observed at a predetermined temperature, or monitored over a range of temperatures.

Conveniently, if a single oligonucleotide probe is used in an investigation in which the oligonucleotide may hybridise to two different alleles with different Tms, a temperature intermediate to the two Tms may be used, or the assay may be performed over a range of temperatures (ie by melt analysis).

It will be appreciated that the method may include two or more oligonucleotide probes of the invention which hybridise to different target sequences (eg different alleles of the same gene). Conveniently, these may be distinguished by using fluorophores with different fluorescent properties, or the two or more oligonucleotides have different melting characteristics (eg $T_m$s) when hybridised to (or hybridising to) their respective target polynucleotide sequences.

Typically, when a range of temperatures is used, the range encompasses the $T_m$ for the hybrid formed between the oligonucleotide and its polynucleotide target. Conveniently, the temperature range is ±10° C., typically ±5° C. compared to the $T_m$.

Conveniently, if two different oligonucleotide probes are included in an investigation the assay is performed over a range of temperatures (ie by melt analysis).

It is particularly useful to carry out the method of the invention such that an observation of the rate of change of the fluorescent signal with temperature is made.

Typically, the oligonucleotides of the invention are ones which form a hybrid with their target polynucleotide sequence wherein the hybrid has a $T_m$ of from 20° C. to 90° C., preferably from 40° C. to 70° C.

In a situation where an oligonucleotide probe of the invention is used to detect a fully complementary target sequence and a partially complementary target sequence, preferential hybridisation to the fully complementary sequence may occur if the target concentration exceeds the concentration of probe since mismatched sequences are less stable. In extreme cases, preferential hybridisation may detect only the fully complementary form of the target. Increasing the concentration of the probe may, therefore, be employed to encourage hybridisation to mismatched targets and improve the balance of peak heights.

In one embodiment of this aspect of the invention one or more oligonucleotides of the invention are included in PCR assays and emit greater amounts of fluorescence when hybridised to complementary target sequences than when single-stranded. Following amplification, the presence and identity of target sequences is determined by melting curve analysis (French et al, 2001, French et al, 2002). The stability and melting temperature of hybridised probes depends on the degree of homology between probe and target sequence. Increasing the reaction temperature above the Tm of the oligonucleotide of the invention causes probe/target duplexes to dissociate and the amount of fluorescence emission to decrease. Sequences differing by as little as a single nucleotide may be detected and differentiated on the basis of melt peak Tm. Fifty cycles of amplification and melt analysis may be completed in as little as 16 minutes. One advantage of using the oligonucleotides of the invention for homogeneous sequence analysis derives from their ability to reliably identify homozygous and heterozygous samples using a single oligonucleotide probe.

The polynucleotide target may be DNA, RNA or cDNA, and is used in single-stranded form, or a DNA duplex may be probed to form a triplex. In one embodiment, the polynucleotide target has a known polymorphism, preferably a single nucleotide polymorphism (SNP). The target is incubated under hybridising conditions with an oligonucleotide probe of the invention. It is necessary that the hybrid generate a stronger fluorescence signal than the single-stranded oligonucleotide probe. The melting temperature of the hybrid will depend, amongst other things, on whether the polynucleotide target and oligonucleotide probe are fully complementary or whether there is a, single or even a double mismatch arising at or close to the location of the SNP. The method involves observing the level of fluorescence signal, emitted by the oligonucleotide probe, at a predetermined temperature near the melting temperature of the hybrid, or over a range of temperatures. Two alternatives are described, although others are possible:— a) The temperature of a solution containing the hybrid is slowly raised, while continuously observing a fluorescence signal, in order to construct a graph of the negative derivative of fluorescence signal intensity with respect to temperature (−dF/dT) against temperature. The melting temperature (Tm) of the hybrid appears as a peak, and provides information about the sequence of the polynucleotide target. The Tms generated through melting analysis of the oligonucleotide of the invention may be used to distinguish polymorphic targets. Similarly, the analysis may be performed by cooling the solution slowly from high temperature and determining the annealing temperature.

b) A solution of the hybrid is held at a predetermined temperature and the level of fluorescence observed. Generally, the predetermined temperature is chosen to be intermediate between the melting temperature of a perfectly matched hybrid and the melting temperature of a hybrid with one or two mismatches. The level of fluorescence signal observed provides an indication of whether or not the hybrid has dissociated, and so provides information about the sequence of the polynucleotide target. Polymorphic targets may be distinguished in end-point and real-time formats.

Conveniently, the polynucleotide target may be a PCR amplimer, formed by using suitable primers to amplify a desired portion of genomic DNA. It may be convenient to perform the amplification and target investigation in a homogenous mode, e.g. in a single reaction vessel by adding the oligonucleotide probe before, during or after the amplification cycling procedure. It may also be convenient to perform target amplification and sequence investigation directly from samples, such as saliva, without prior extraction of DNA, RNA or cDNA. Preferably the oligonucleotide probe is modified at its 3'-end so as to prevent chain extension during PCR amplification. In another aspect, target amplification may be performed using asymmetric PCR to generate an abundance of the single-stranded target. Preferential probe hybridisation to fully complementary target sequences over mismatched targets may be avoided by increasing probe concentration. Target amplification for assays using the oligonucleotide of the invention may also be performed using alternate techniques such as ligation chain reaction (LCR)

rolling circle amplification (RCA), strand displacement amplification (SDA), transcription mediated amplification (TMA) and nucleic acid sequence based amplification (NASBA). Typically, probe concentrations higher than 150 nM are used in asymmetric assays.

It may be convenient to provide two or more of the oligonucleotides of the invention, one fully complementary to each allele of the SNP under investigation. Where each oligonucleotide of the invention carries a different fluorophore, it may be convenient to mix the probes in solution for analysis of homozygous and heterozygous targets. In the same way, a mixture of oligonucleotides of the invention complementary to the various alleles of several different SNPs may be used together in solution for multiplex analysis, provided that each is labelled with a spectrally distinct fluorophore. Such multiplex analysis may also be performed using a single type of reporter dye (fluorophore), employing two or more oligonucleotides of the invention that exhibit different matched and mismatched Tms, such that multiple targets and alleles may be detected and identified simultaneously on the basis of melting temperature.

The method of the invention may be carried out wherein the oligonucleotide which is able to hybridise to the target polynucleotide sequence, the sample which may contain the polynucleotide target sequence or both are immobilised on or within a support.

The target polynucleotide sequence is preferably selected from the group consisting of the human genome including any gene therein or allele thereof, the mouse genome or any gene therein or allele thereof, and the genome of any infectious agent including any gene therein or allele thereof. Preferred target sequences are as described above.

A further aspect of the invention provides a process for making an oligonucleotide of the invention, the process comprising selecting a target polynucleotide sequence and synthesising an oligonucleotide which has a sequence complementary to the target polynucleotide and which has the properties as set out in the first aspect of the invention. Typically, the oligonucleotide is one which is able to hybridise to the target sequence. The oligonucleotide may be one which is fully complementary to the target sequence or it may be one which is mismatched as described above.

Preferably, the target polynucleotide sequence is selected from the group consisting of the human genome including any gene therein or allele thereof, the mouse genome including any gene therein or allele thereof, and the genome of any infectious agent including any gene therein or allele thereof as descried in more detail above.

The oligonucleotides of the invention produced by this method may be placed on an array, thus the invention also includes a process of producing an array of oligonucleotides by placing two or more oligonucleotides of the invention on a solid support. Typically, the sites where the oligonucleotides have been placed (attached) are uniformly distributed on the support.

All documents herein referred to are expressly incorporated herein by reference in their entireties.

The invention will now be described in more detail by reference to the following non-limiting Examples and Figures.

FIG. 1 shows the chemical structures of the C6 FAM dU and Glen Fluorescein dT labels employed in the oligonucleotides of the invention.

FIG. 2 shows that a single-labelled oligonucleotide (HYBA1928C) was employed to directly analyse saliva samples with respect to the 5,10-methylenetetrafolate reductase (MTHFR) A1928C polymorphism. The negative derivative of fluorescence with respect to temperature (−dF/dT on y-axis) was plotted against sample temperature (x-axis) to generate melt peaks. The oligonucleotide yields melt peaks with Tms of approximately 51.5° C. and 61° C. in the presence of A and C alleles respectively. Heterozygous samples generate both 51.5° C. and 61° C. melt-peaks.

FIG. 3 shows melt peaks derived from single-labelled (FVG1) and dual-labelled (FVG11) factor V oligonucleotides. The additional fluorophore causes melt peak height to increase by 4-5 fold and reduces the probe Tm by approximately 5° C.

FIG. 4. A) HYBCH2 probe melt peaks obtained with purified DNA from *Chlamydia trachomatis* (LGV-II, strain 434, ATCC VR-920B, Advanced Biotechnologies, Maryland, U.S.) and processed clinical swab samples. A single melt peak, with a Tm of approximately 60° C., is generated in the presence of *Chlamydia* target DNA. B) Real-time PCR and melt peak data obtained with the HYBCH6 *Chlamydia* probe. The triple-labelled *Chlamydia* probe yields melt peaks that are approximately 6 times the magnitude of the single-labelled HYBCH2 oligonucleotide.

FIG. 5 shows HYBNG (a dual-labelled oligonucleotide of the invention) melt peaks obtained with purified *Neisseria gonorrhoeae* DNA. A single melt peak is generated with a Tm of approximately 59° C.

FIG. 6. A) Melt peaks obtained from a series of purified human genomic DNAs, using the dual-labelled FVG11 probe to type samples with respect to the factor V Leiden polymorphism. Homozygous wild-type samples generate a single melt peak with a Tm of approximately 55° C. Heterozygous samples simultaneously yield matched and mismatched melt peaks possessing Tms of approximately 55° C. and 45° C. respectively. Homozygous 'mutant' samples would yield only the 45° C. melt peaks. Negative control reactions generate neither melt peak. B) The LightCycler software may be employed to type samples with respect to the Factor V polymorphism based on the number and Tm of melt peaks.

FIG. 7 shows a method to calculate probe signal-to-noise ratio. Fluorescence readings are measured at Tm plus and minus 10° C. for dissociated and hybridised probe states respectively. The signal-to-noise ratio may be calculated as the hybridised signal divided by the dissociated signal.

FIG. 8. A) The dual-labelled FVG11 probe exhibits approximately twice the amount of background fluorescence (above 70° C.) compared with the single-labelled FVG1 probe. However, B) the dual-labelled factor V probe yields melt peaks that are approximately 5-6 times the size of the peaks generated with the single-labelled probe. This shows that the signal-to-noise ratio is ~3 times better with FVG11 compared to FVG1 compared to the expected result which is that twice the fluorophore would produce twice the background and twice the signal, therefore an unchanged signal-to-noise ratio. The FVG1 and FVG11 probes exhibit 33% and 82% increases in fluorescence upon hybridisation, respectively.

FIG. 9 shows a comparison of single (FVG1) and dual-labelled (FVG11) factor V probes using purified genomic samples. Melt peaks were analysed using 10° C. to average smoothing of data and the polynomial with background correction LightCycler function. Negative control reactions (NC) do not produce melt peaks with either FVG1 or FVG11 probes. 1 ng/µl of homozygous 'wild-type' DNA yields single melt peaks with Tms of approximately 59° C. and 54.6° C. for single and dual-labelled probes respectively. Heterozygous (HET) genomic samples yield both matched and mismatched melt peaks. The heights of dual-labelled melt peaks are approximately 3-4 times greater than those generated with the single-labelled probe.

FIG. 10 shows a comparison of 3', 5' and internally labelled probes of identical sequence. The 5'-labelled probe exhibited fluorescence quenching upon target hybridisation and generated inverted peaks in −dF/dT traces. The 3'-labelled probe displayed neither fluorescence enhancement nor quenching upon hybridisation. The internally labelled oligonucleotide displayed fluorescence enhancement upon target hybridisation and positive melt peaks in −dF/dT traces. Both the single and dual-labelled probes are independent of the target sequence and always exhibit enhanced levels of fluorescence when hybridised.

FIG. 11. A) Comparison of HYBCH (1), HYBCH2 (2), HYBCH3 (3) and HYBCH4 (4) *Chlamydia* probes. The probes labelled with 3 and 4 FAM dyes emit considerably lower levels of fluorescence compared with the single and dual-labelled probes due to the close proximity of the labels. The triple-labelled probe (3) exhibits increased levels of emission upon duplex dissociation. B) Melt peaks derived from the four *Chlamydia* probes. The triple-labelled probe yields small inverted melt peaks at a Tm higher than the dual-labelled variant. The probe labelled with 4 FAM dyes yields a small positive melt peak with a Tm approximately equal to that generated with the dual-labelled probe. C) Comparison of dual-labelled HYBCH (1), single-labelled HYBCH2 (2), and triple-labelled HYBCH5 (5) and HYBCH6 (6) oligonucleotides.

Figure 14:
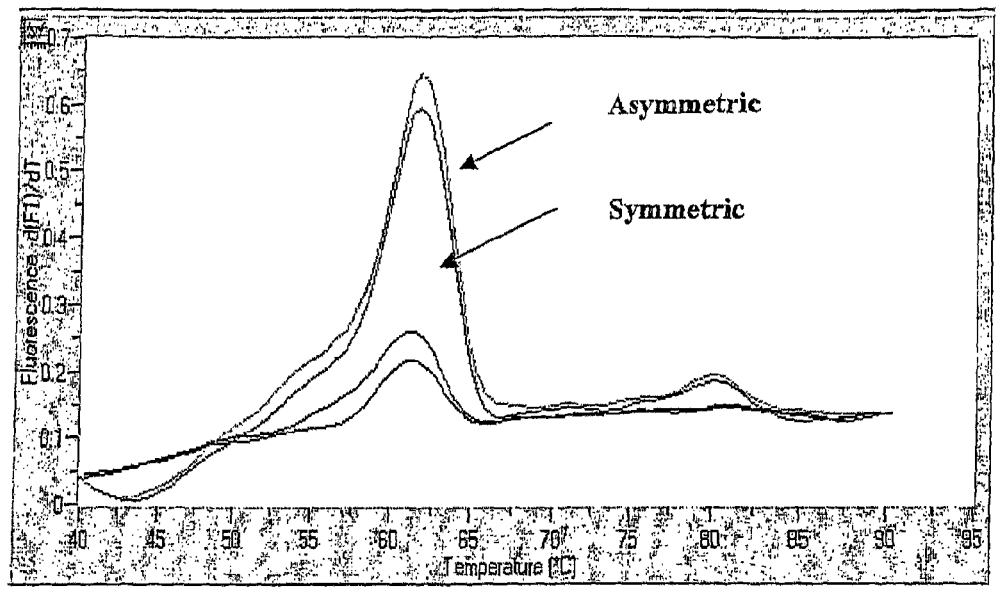
Figure 14:
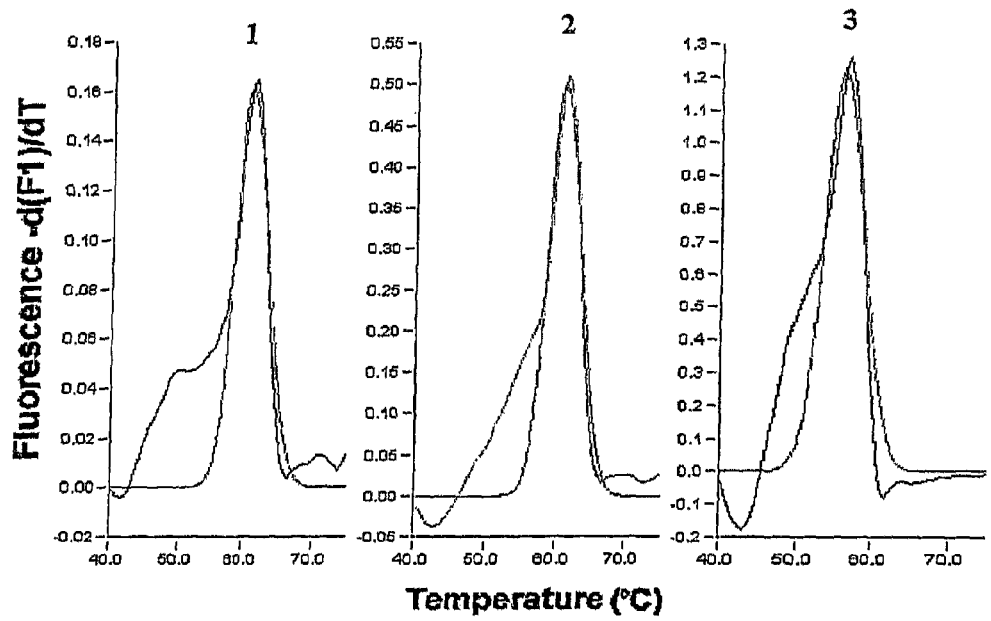

FIG. 14. A) Comparison of symmetric and asymmetric PCR protocols for the detection of *Chlamydia trachomatis* using the HYBCH2 probe. B) Comparison of symmetric PCR and single-labelled probe (1) with asymmetric amplification and single-labelled probe (2) and asymmetric PCR with the dual-labelled probe variant (3). The height of *Chlamydia* melt peaks is enhanced by more than 7-fold using asymmetric PCR and the dual-labelled HYBCH probe.

Figure 15:
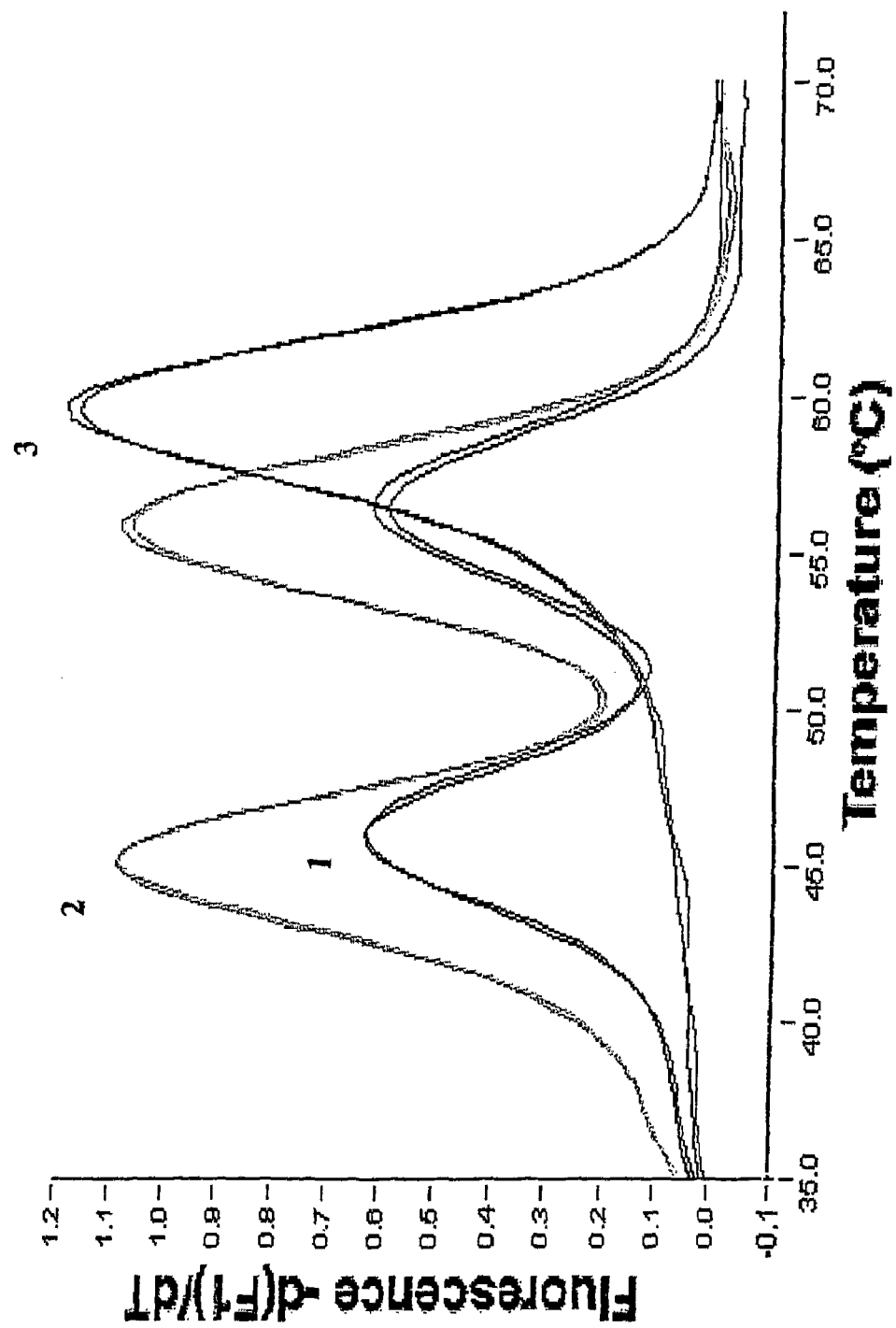

FIG. 15. 150 nM of FVG11 was hybridised to 75 nM of FVG and 75 nM of FVA oligonucleotide targets (1). 300 nM of the probe was hybridised to 150 nM of FVG and 150 nM of FVA (2). 150 nM of probe was also hybridised to 500 nM of FVG and 500 nM of FVA. At high target concentration, preferential hybridisation of the probe to the fully complementary target sequence completely prevents detection of the mismatched target variant (3).

Figure 16:
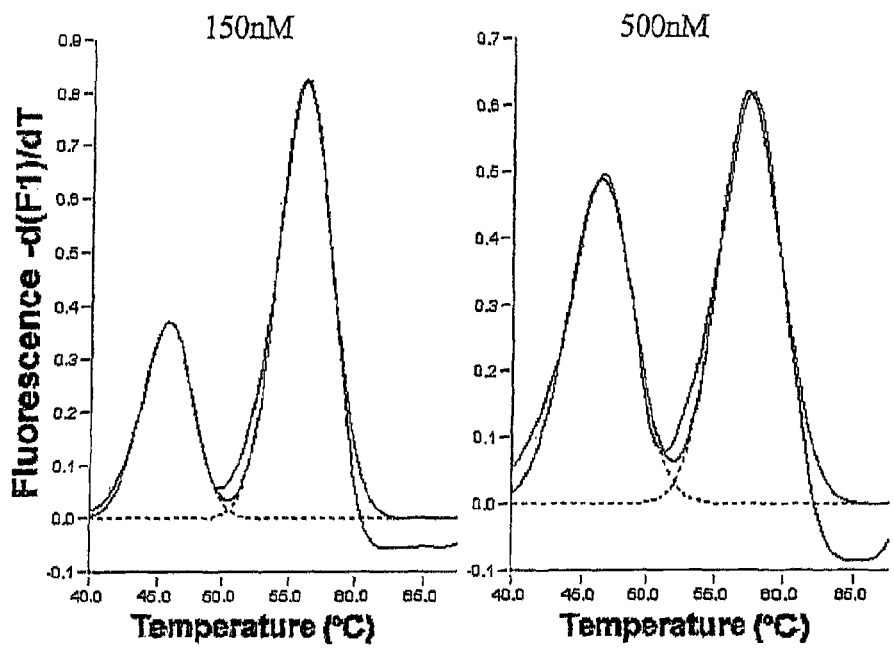
Figure 16:
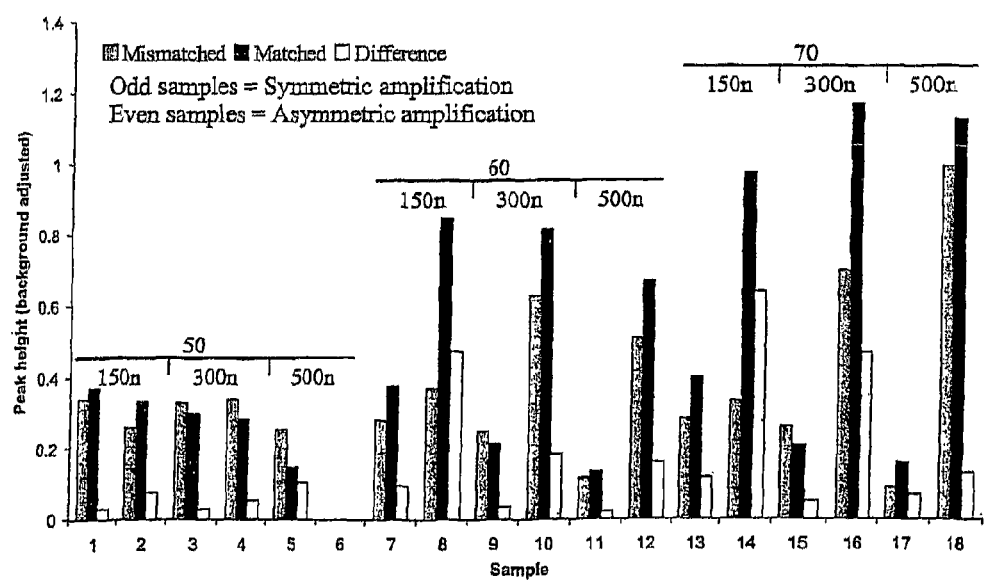

FIG. 16. A) Following 60 cycles of asymmetric target amplification, the heights of matched and mismatched factor V melt peaks are unbalanced when 150 nM of FVG11 probe is employed. Increasing probe concentration to 500 nM improves the balance of melt peak heights. B) The heights of FVG11 melt peaks were measured after 50, 60 and 70 cycles of symmetric and asymmetric target amplification using 150 nM, 300 nM and 500 nM of the FVG11 probe.

Figure 17:
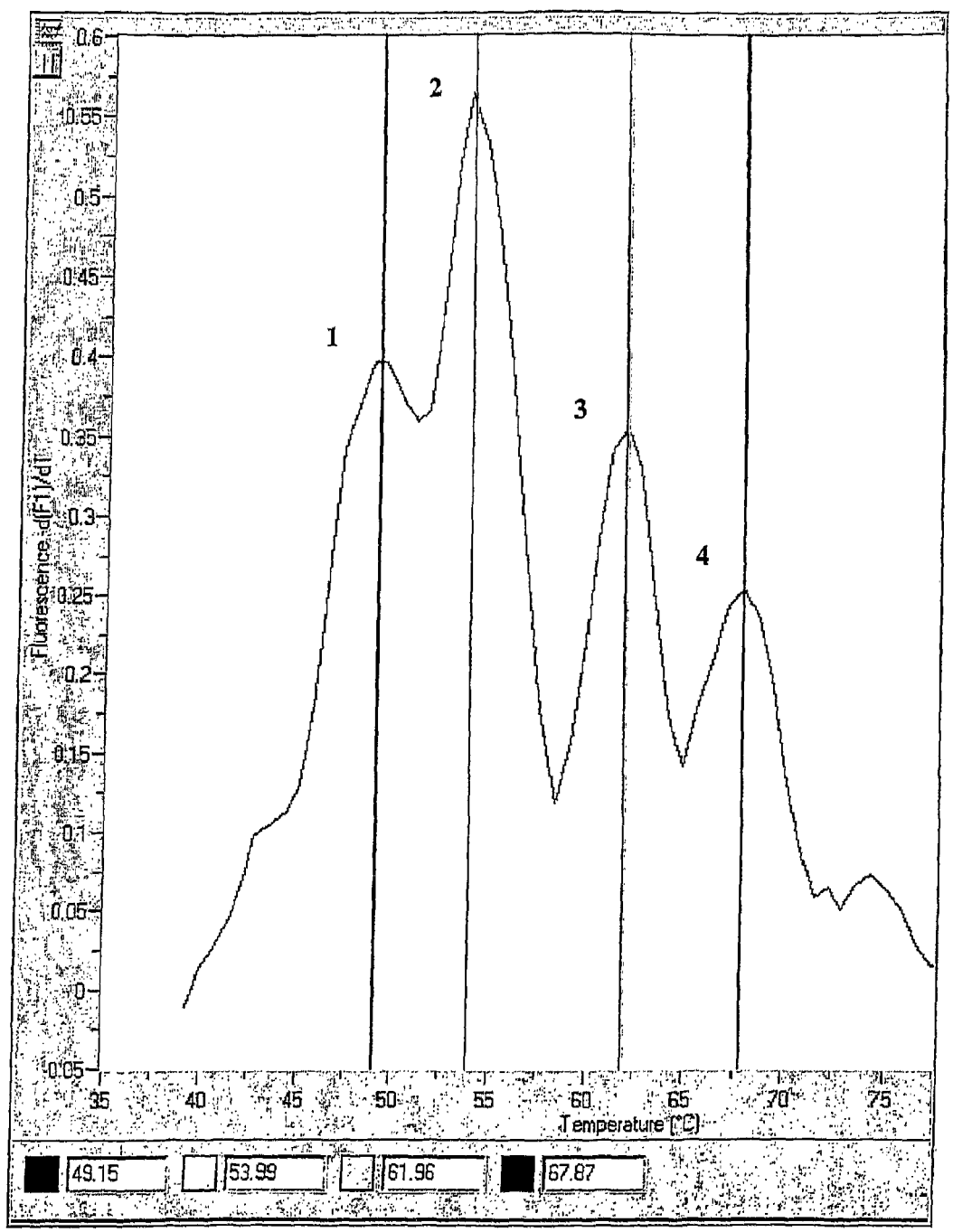

FIG. 17 shows multiplex detection of target sequences using PolyT (1), HYBINF (2), HYBCH2 (3) and HyBAdC (4) oligonucleotide probes. Multiplex detection was on the basis of melt peak Tm and employed FAM on all probes.

Figure 18:
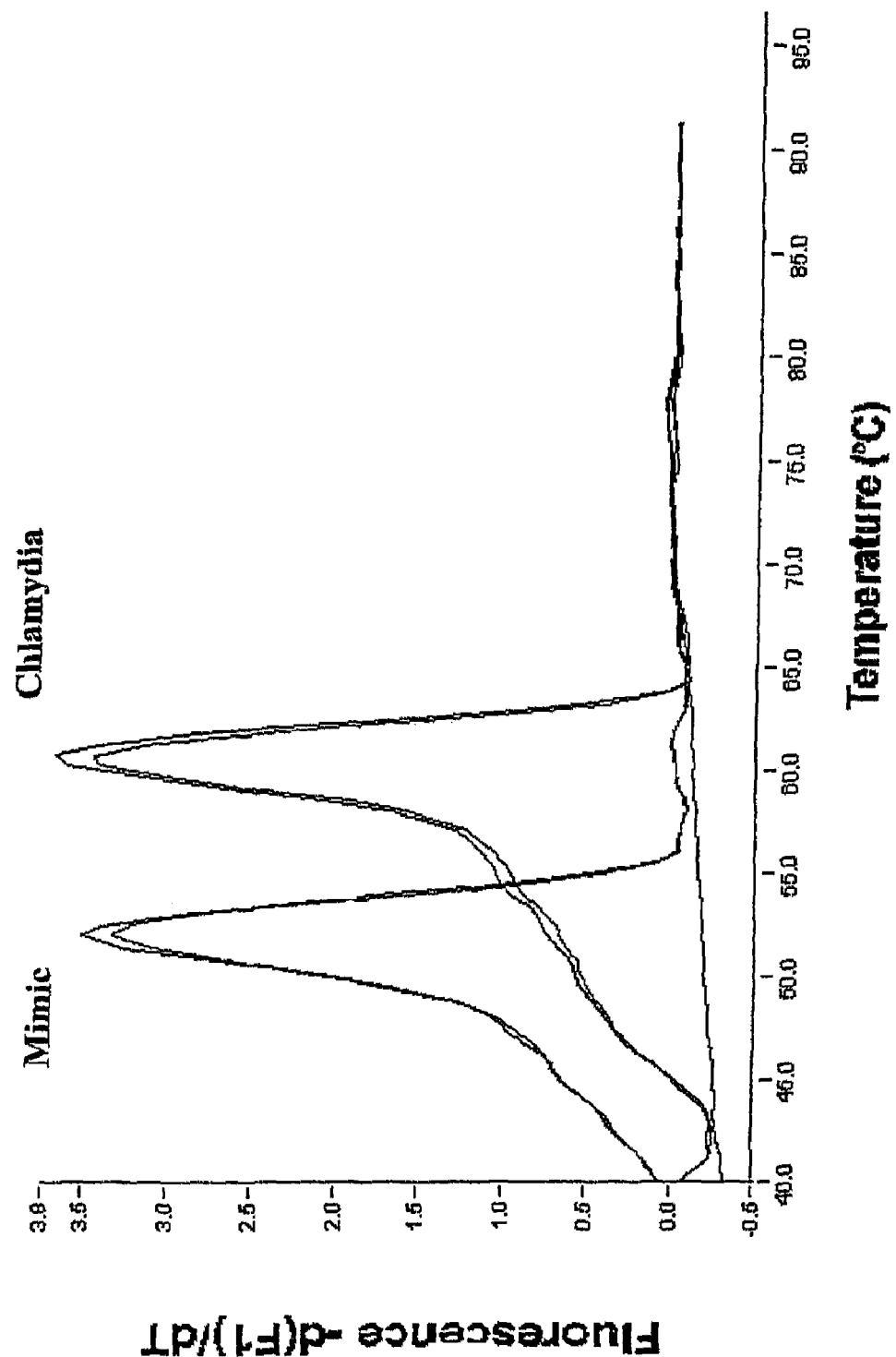

FIG. 18 shows melt peaks obtained with the triple-labelled HYBCH6 probe detecting matched and mismatched target sequences amplified from purified *Chlamydia* DNA and mimic plasmid respectively. The probe displays Tms of approximately 60.3° C. and 51.8° C. with Chlamydial DNA and mimic targets respectively. No peaks are generated in the absence of target.

Figure 19:
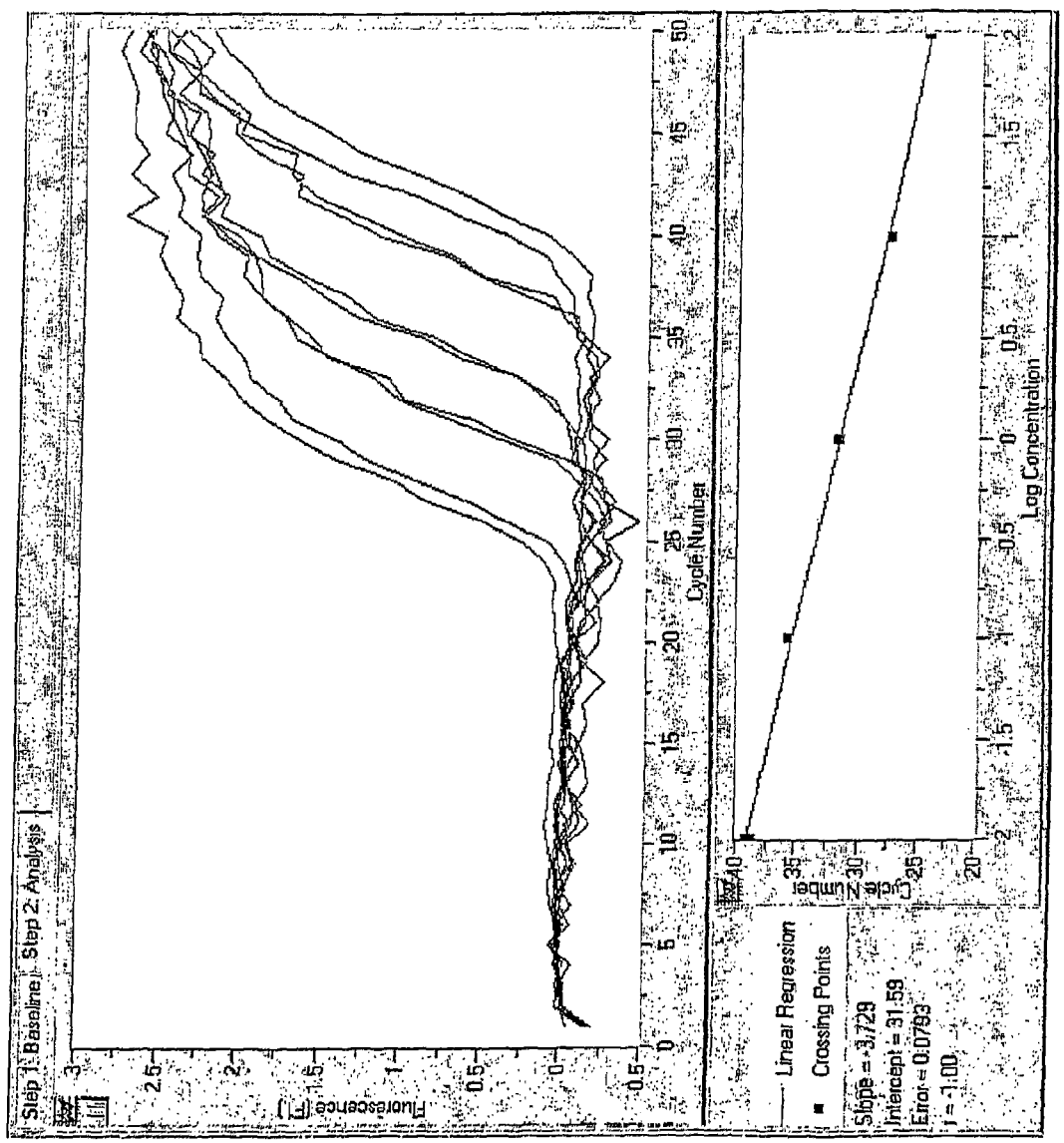

FIG. 19 shows the dual-labelled FVG11 probe was employed to generate a real-time standard curve using dilutions of human genomic DNA. The dilution series comprised 100 ng/µl, 10 ng/µl, 0.1 ng/µl and 0.01 ng/µl of genomic DNA.

Figure 20:
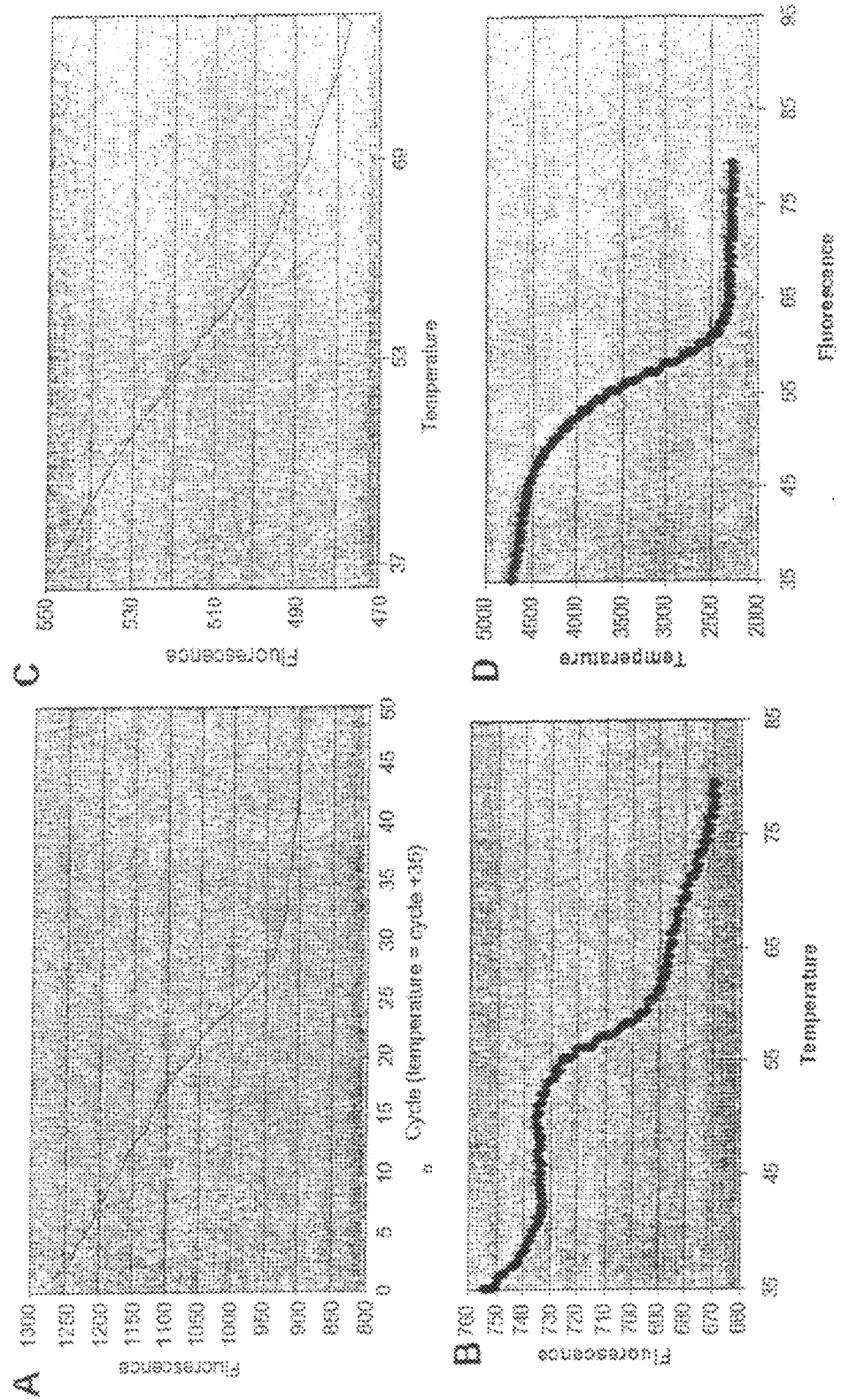

FIG. 20 shows melting curves for dual-labelled FVG11 derivative probes labelled with A. TAMRA, B. ROX, C. Cy5, D. ROX and FAM and inflections therein indicating changes in fluorescence as a result of hybridisation state.

MATERIALS AND METHODS PERTAINING TO THE EXAMPLES

Oligonucleotide Probe Design and Synthesis

Figure 1:
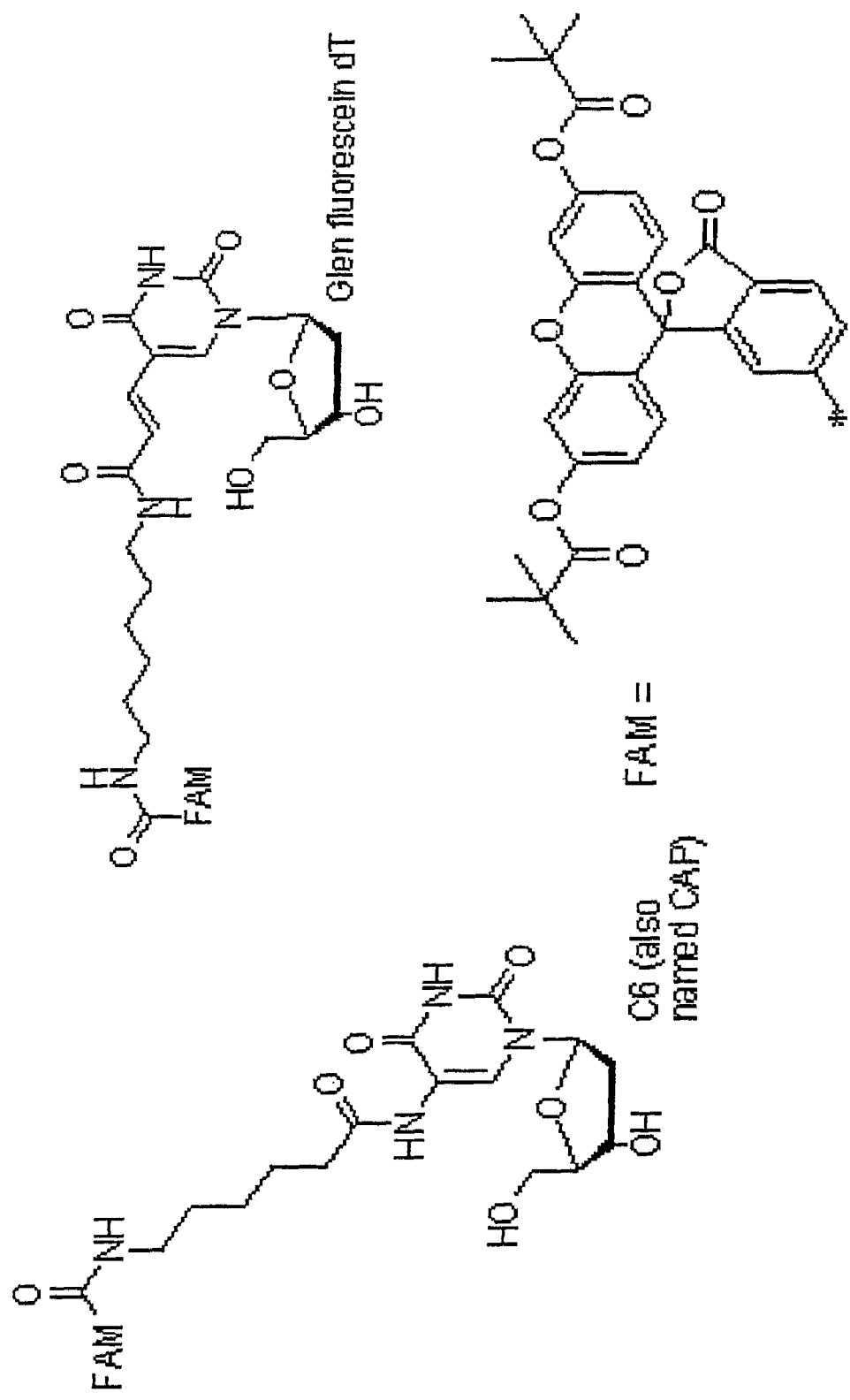

The oligonucleotide probes of the invention are typically designed to be approximately 18-25 nucleotides in length or possess Tms of approximately 55-60° C. when hybridised to fully complementary target sequences. Fluorophores are attached to internal residues in the probe sequence using either C6 FAM dU (University of Southampton, UK) or Fluorescein dT (Glen Research, Sterling, Va.). In the case of C6 FAM dU (FIG. 1), 6-Carboxyfluorescein (FAM) is attached to the 5-position of uracil bases through methods of DNA synthesis which are well known to those in the field. Fluorophores may be incorporated into probes as phosphoramidites during solid-phase oligonucleotide synthesis (Brown et al, 2001, Brown et al, 2003). Other fluorescent modifications can also be made post synthesis using monomers such as 8-aminoalkyl-dA and 5-aminoalkyl-dC from Glen Research. The oligonucleotides of the invention may possess a 3'-phosphate component or other blocking agent to prevent Taq mediated extension when the probes are incorporated into real-time PCR assays. The quantity of probe obtained from the synthesis is determined by dissolving an aliquot of the oligonucleotide probe in a specific volume of water and measuring the UV absorbance at 260 nm. The concentration of the probe is calculated from the UV absorbance of the oligonucleotide and its extinction coefficient at 260 nm. The extinction coefficient of the oligonucleotide is calculated from the sum of the individual extinction coefficients of the unmodified and fluorescently labelled nucleosides of which it is composed.

Polymorphic sites are conveniently positioned towards the centre of the oligonucleotides to maximise the Δ™. The nucleotide at the site of polymorphism is typically selected such that highly destabilising interactions occur when probes are hybridised to mismatched targets. Probes exhibiting C/A, C/T and C/C mismatches are employed preferentially whilst G/T, G/A and G/G mismatches are avoided. As discussed above, the oligonucleotide probe may have 70% or 80% or 85% or 90% or 95% sequence identity to the complement of its target.

Polymerase Chain Reaction

PCR volumes are typically 20 µl, comprising 2 µl of sample, 1×PCR buffer, 0.5 µM primers, 1 unit Taq polymerase (Amersham Pharmacia Biotech), 3 mM total $MgCl_2$, 5 ng/µl BSA (Roche Diagnostics), 1 mM dNTPs (Amersham Pharmacia Biotech) and 150 nM of probe. The buffers employed in assays using the oligonucleotides are 10×PCR buffer (TaKaRa, contains 1.5 mM $MgCl_2$), 10×HEPES#7 (100 mM HEPES pH8.3, 250 mM KCl) for direct urine analysis and 10×HEPES#8 (100 mM HEPES pH8.3, 500 mM KCl) for direct saliva analysis and purified/processed samples. Homogeneous amplification and detection of targets may be performed using a LightCycler instrument (Roche Diagnostics). Real-time PCR detection and target quantification may be achieved with a 3-stage thermal protocol where, following an initial denaturation reaction step (95° C. 1 min), targets are amplified using 50 cycles comprising denaturation (95° C. 5 s), primer annealing (55° C. 10 s) and extension of products (72° C. 10 s). Fluorescence acquisition is performed once per cycle, in 3-stage assays, at the end of each primer-annealing step. Alternatively, targets may be rapidly amplified using a 2-stage thermal protocol where, following an initial denaturation step (95° C. 1 min), targets are amplified using 50 cycles comprising denaturation (95° C. 5 s) and a combined annealing/extension phase (65° C. 10 s). Fluorescence is not acquired during 2-stage amplification.

Target Detection and Identification

Following 3-stage and 2-stage amplification, reactions are immediately denatured (95° C. 0 s) and cooled (35° C. 30 s) prior to melt curve analysis (35-95° C. with a 0.2° C./s transition rate) where fluorescence is acquired continuously. Melt peaks are constructed using the LightCycler software (version 3.5) by plotting the negative derivative of fluorescence with respect to temperature (−dF/dT on the y-axis) against temperature (x-axis). Targets may be reliably detected and identified using the melting temperatures (Tm) of the oligonucleotide probe peaks.

Example 1

Exemplary Single-Labelled Oligonucleotide Probes

The following are examples of probes that have been used for the detection of target sequences and identification of polymorphic targets. The primer sequences used to amplify corresponding targets are provided. This example contains single labelled oligonucleotide probes for comparison with the dual and multiple labelled probes of the invention.

Analysis of the NAT2*5A (C481T) polymorphism may be performed by melt analysis using oligonucleotide probes such as 2303002 (5'GAGAGGAATCFGGTACCTGGACC (SEQ ID NO:1)), where F is a fluorescent labelled nucleotide and underlined bases represent the position of polymorphism. PCR extension from the probe is blocked with a 3' phosphate. The target sequence containing the NAT2*5A SNP may be amplified using primers such as 195993 (5'CCTCTAGAAT-TAATTTCTGGG (SEQ ID NO:2)) and 195991 (5'CT-GCTCTCTCCTGATTTGGTCC (SEQ ID NO:3)). The fully complementary *4 and mismatched (C:A)*5A alleles may be reliably detected and identified on the basis of probe Tm (table 1). The 2303002 probe is designed to hybridise to a section of the NAT2 gene (Genbank Accession X14672) having a sequence of either:

```
NAT2*4   5'GGTCCAGGTACCAGATTCCTCTC    (SEQ ID NO: 4)
NAT2*5A  5'GGTCCAAGTACCAGATTCCTCTC    (SEQ ID NO: 5)
```

Analysis of the NAT2*5C (A803G) polymorphism may be performed by melt analysis using an oligonucleotide probe such as DdeFL1*4 (5'GAAGTGCFGAAAAATATATT-TAAG (SEQ ID NO:6)), where F is a fluorescent labelled nucleotide and underlined bases represent the position of polymorphism. PCR extension from the probe is blocked with a 3' phosphate.

The target sequence containing the NAT2*5C SNP may be amplified using primers such as DdeF2 (5'CCTATA-GAAAATTCAATTATAAAG (SEQ ID NO:7)) and DdeR (5'VACGAGATTTCTCCCCAAGG (SEQ ID NO:8)). The fully complementary *4 and mismatched (A:C)*5C alleles may be reliably detected and identified on the basis of probe Tm (table 1). The DdeFL1*4 probe is designed to hybridise to a section of the NAT2 gene (Genbank Accession X14672) having a sequence of either:

```
NAT2*4   5'CTTAAATATATTTTTCAGCACTTC    (SEQ ID NO: 9)
NAT2*5C  5'CTTAAATATATTTCTCAGCACTTC    (SEQ ID NO: 10)
```

Analysis of the NAT2*7 (G857A) polymorphism may be performed by melt analysis using an oligonucleotide probe such as BamFL1*7 (5'CCTGGTGAFGAATCCCTTAC (SEQ ID NO:11)), where F is a fluorescent labelled nucleotide and underlined bases represent the position of polymorphism.

PCR extension from the probe is blocked with a 3' phosphate. The target sequence containing the NAT2*7 SNP may be amplified using primers such as BamF2 (5'CCTATA-GAAAATTCAATTATAAAG (SEQ ID NO:12)) and BamR (5'CACGAGATTTCTCCCCAAGG (SEQ ID NO:13)). The fully complementary *7 and mismatched (A:C)*4 alleles may be reliably detected and identified on the basis of probe Tm (see table 1). The DdeFL1*7 probe is designed to hybridise to a section of the NAT2 gene (Genbank Accession X14672) having a sequence of either:

```
NAT2*4   5'GTAAGGGATTCATCACCAGG       (SEQ ID NO: 14)
NAT2*7   5'GTAAGGGATCCATCACCAGG       (SEQ ID NO: 15)
```

Analysis of two NAT1*10 SNPs may be performed by melt analysis using an oligonucleotide probe such as HYBNAT3S (5'CTTTAAAATACAFTTTTTATTATTA (SEQ ID NO:16)), where F is a fluorescent labelled nucleotide and underlined nucleotides represent positions of polymorphism. PCR extension from the probe is blocked with a 3' phosphate. Fully complementary, mismatched and double mismatched alleles may be reliably detected and identified on the basis of probe Tm (see table 1). Functionality of this probe has been demonstrated using complementary oligonucleotides possessing all possible base combinations at the positions of polymorphism. The HYBNAT3S probe is designed to hybridise to a section of the NAT1 gene (Genbank Accession AY376850) having a sequence of either:

```
NATRAA   TAATAATAAAAAATGTATTTTAAAGATGGC   (SEQ ID NO: 17)
NATRTA   TAATAATAATAAATGTATTTTAAAGATGGC   (SEQ ID NO: 18)
NATRTC   TAATAATAATAAATGTCTTTTAAAGATGGC   (SEQ ID NO: 19)
NATRAC   TAATAATAAAAAATGTCTTTTAAAGATGGC   (SEQ ID NO: 20)
```

Analysis of the Factor V Leiden (G1691A) polymorphism may be performed by melt analysis using an oligonucleotide probe such as FVG1 (5'CTGTAFTCCTCGCCTGTCC (SEQ ID NO:21)), where F is a fluorescent labelled nucleotide and the underlined nucleotide is the position of polymorphism. PCR extension from the probe is blocked with a 3' phosphate. The target sequence containing the factor V SNP may be amplified using primers such as FVF1.3 (5'GGACTACT-TCTAATCTGTAAGAGCAGATC (SEQ ID NO:22)) and FVR3.5 (5'GCCCCATTATTTAGCCAGGAGACCTAA-CATG (SEQ ID NO:23)). The fully complementary 'wild-type' and mismatched (C:A) 'mutant' alleles may be reliably detected and identified on the basis of probe Tm (see table 1). The FVG1 probe is designed to hybridise to a section of the Factor V gene (Genbank Accession AY364535) having a sequence of either:

```
FVG   5'GGACAGGCGAGGAATACAG    (SEQ ID NO: 24)
FVA   5'GGACAGGCAAGGAATACAG    (SEQ ID NO: 25)
```

Simultaneous analysis of the sickle cell anaemia HbS and HbC polymorphisms may be performed by melt analysis using a single labelled oligonucleotide probe such as SCT1 (5'GTGCACCTGACFCCTGTGG (SEQ ID NO:26)), where F is a fluorescent labelled nucleotide and underlined nucleotides are the positions of polymorphism. PCR extension from the probe is blocked with a 3' phosphate. The target sequence containing the sickle cell polymorphisms may be amplified using primers such as SCF1 (5'AGGGCAGAGC-CATCTATTGCT (SEQ ID NO:27)) and SCR2 (5'CATC-CACGTTCACCTTGCC (SEQ ID NO:28)). The fully complementary (GT:CA) HbS, mismatched (GT:CT) wild-type and double mismatched (GT:TT) HbC alleles may be reliably detected and identified on the basis of probe Tm (table 1). The SCT1 probe is designed to hybridise to a section of the β-globin gene (Genbank Accession AY356351) having a sequence of either:

```
HbS    5'CCACAGGAGTCAGGTGCAC    (SEQ ID NO: 29)
HbWT   5'CCTCAGGAGTCAGGTGCAC    (SEQ ID NO: 30)
HbC    5'CCTTAGGAGTCAGGTGCAC    (SEQ ID NO: 31)
```

Detection of the *Chlamydia trachomatis* cryptic plasmid may be performed by melt analysis using an oligonucleotide probe such as HYBCH2 (5'CAAGCCTGCAAAFGTATAC-CAAG (SEQ ID NO:32)), where F is a fluorescent labelled nucleotide. PCR extension from the probe is blocked with a 3' phosphate. The cryptic plasmid target sequence may be amplified using primers such as CHF3-1 (5'GGGTTCGTTG-TAGAGCCATGTCCTATCTTG (SEQ ID NO:33)) and CHR4-1 (5'CGCAGCTGCTGTAATCACCCAGTC-GATAAA (SEQ ID NO:34)). The *Chlamydia* cryptic plasmid and a mismatched (C:A) positive amplification control (see below) may be reliably detected and identified on the basis of probe Tm (see table 1). The HYBCH2 probe is designed to hybridise to a section of the cryptic plasmid (Genbank Accession X07547) having a sequence of either:

```
HYBCHRC  5'CTTGGTATACATTTGCAGGCTTG    (SEQ ID NO: 35)
Mimic    5'CTTGGTATACATTTACAGGCTTG    (SEQ ID NO: 36)
```

Further assays employing single-labelled oligonucleotide probes to analyse targets such as CYP2D6*3, CYP2D6*4, CYP2C19 m1, CYP2C19 m2, CYP2C9*2 and CYP2C9*3 SNPs are described in WO 01/73118 A2.

TABLE 1

Oligonucleotide probe Tms, at 3 mM MgCl$_2$, with fully complementary and mismatched targets. Melt peaks and Tms were obtained from complementary oligonucleotides and PCR amplified target sequences. Sequence identification numbers for probes and targets are included.

| Probe | SEQ IDs | Sequence | Matched Tm | Mismatched Tm |
|---|---|---|---|---|
| PolyT | 37, 38 | TTTTTTTTTTTFTTTTTTTTTTT | 49.6 | — |
| C19m1A | 39-41 | GATTATTFCCCAGGAACCC | 56.6 | 51.5 |
| HYBNAT3S | 16-19 | CTTTAAAATACAFTTTTTATTATTA | 49.7 | 42.8 36.0 |
| C19m2G | 42-44 | TACCFGGATCCAGGGGGTG | 57.5 | 47 |
| FVG1 | 21, 24-25 | CTGTAFTCCTCGCCTGTCC | 59.0 | 49.5 |
| HEPB | 45-46 | AAGAACTCCCFCGCCTCGCA | 62.3 | — |
| PJ18S | 47-48 | GAGACGAACAACFGCGAAAGC | 58.6 | — |
| HYBCH2 | 32, 35 | CAAGCCTGCAAAFGTATACCAAG | 60.6 | — |
| NAT2*5 | 124, 4-5 | GAGAGGAATCFGGTACTTGGACC | 61.3 | 57.1 |
| 2303002 | 1, 4-5 | GAGAGGAATCFGGTACCTGGACC | 52.4 | 42.3 |
| BamFL1*7 | 11, 14-15 | CCTGGTGAFGAATCCCTTAC | 56.7 | 48.9 |
| HSV1 | 49-50 | GGACACCGGCGCFACTTCACCT | 66.0 | — |
| DdeFL1*4 | 6, 9-10 | GAAGTGCFGAAAAATATATTTAAG | 53.5 | 45.5 |

TABLE 1-continued

Oligonucleotide probe Tms, at 3 mM MgCl$_2$, with fully complementary and mismatched targets. Melt peaks and Tms were obtained from complementary oligonucleotides and PCR amplified target sequences. Sequence identification numbers for probes and targets are included.

| Probe | SEQ IDs | Sequence | Matched Tm | Mismatched Tm |
|---|---|---|---|---|
| 2D64C* | 51-53 | GGGCGFCCTGGGGGTG | 60.4 | 49.3 |
| C9*2T | 54-56 | CATTGAGGACTGFGTTCAAG | 54.8 | 52.1 |
| C9*2C | 55-57 | CATTGAGGACCGFGTTCAAG | 57.8 | 48.2 |
| SCT1 | 26, 29-31 | GTGCACCTGACFCCTGTGG | 57.9 | 52.2 47.6 |
| HYBNG | 58-59 | TCTGCFTCCGCFACGGCTTC | 59.0 | — |
| FVG11 | 60, 24-25 | CTGTAFTCCTCGCCFGTCC | 55.0 | 45.0 |
| FVG111 | 127, 24 | CTGTAFTCCFCGCCFGTCC | 55.0 | — |
| HYBCH | 61, 35 | CAAGCCFGCAAAFGTATACCAAG | 56.0 | — |
| G08377 | 62-63 | ATGGGAAFGGGGAFCCAAATAA | 50.8 | — |
| SP1 | 64-65 | GGGGTCTFCCACTFGGAGAAAGCTATC | 56.8 | — |
| HYBINF | 66-67 | GGGAFCCAAAFAACATGGACAGAGCT | 52.3 | — |
| HYBAdC | 68-70 | GACGTGGFCCGTGFGCACCAGCCT | 65.5 | 52.5 |
| HYBAdD | 69-71 | GACGTGGFCAGAGFGCACCAGCCT | 62.3 | 55.4 |
| FVG1ALT | 101, 24 | CTGTATTCCTCGCCFGTCC | 61.1 | — |
| HYBCH5 | 102-103 | CAAGCCFGCAAAFGTAFACCAAG | 55.2 | — |
| HYBCH6 | 104, 103 | GTAAFCAAGCCFGCAAAFGTATACCAAG | 60.6 | — |
| HYBCH7 | 105, 103 | CAAGCCFGCAAATGTATACCAAG | 61.7 | — |
| HYBCH8 | 106, 103 | CAAGCCTGCAAATGTAFACCAAG | 60.3 | — |
| HYBCH9 | 107, 103 | CAAGCCTGCAAAFGTAFACCAAG | 57.8 | — |
| HYBCH10 | 108, 103 | CAAGCCFGCAAATGTAFACCAAG | 58.3 | — |
| HYBCH11 | 126, 103 | GTAAFCAAGCCFGCAAAFGTAFACCAAG | 57.9 | — |
| HYBMTH | 109-111 | GTCFGCGGGAGCCGAFTTCATC | 63.0 | 54.5 |
| HYBA1928C | 112-114 | GACCAGFGAAGCAAGFGTCTTTG | 61.0 | 51.5 |
| HYBFII | 115-117 | GCATFGAGGCTCGCFGAGAGTC | 63.5 | 54.5 |

Example 2

Exemplary Dual-Labelled Oligonucleotide Probes of the Invention

Analysis of the Factor V Leiden (G1691A) polymorphism may be performed by melt analysis using an oligonucleotide probe such as FVG11 (5'CTGTAFTCCTCGCCFGTCC (SEQ ID NO:60)), where F are fluorescent labelled nucleotides and the underlined nucleotide is the position of polymorphism. PCR extension from the probe is blocked with a 3' phosphate. The target sequence containing the factor V SNP may be amplified using primers such as FVF1.3 (5'GGACTACTTCTAATCTGTAAGAGCAGATC (SEQ ID NO:22)) and FVR3.5 (5'GCCCCATTATTTAGCCAGGAGACCTAACATG (SEQ ID NO:23)). The fully complementary 'wild-type' and mismatched (C:A) 'mutant' alleles may be reliably detected and identified on the basis of probe Tm (see table 1). The FVG1 probe is designed to hybridise to a section of the factor V gene (Genbank Accession AY364535) having a sequence of either:

FVG   5'GGACAGGCGAGGAATACAG   (SEQ ID NO: 24)

FVA   5'GGACAGGCAAGGAATACAG   (SEQ ID NO: 25)

Detection of the *Chlamydia trachomatis* cryptic plasmid may be performed by melt analysis using an oligonucleotide probe such as HYBCH (5'CAAGCCFGCAAAFGTATACCAAG (SEQ ID NO:61)), where F are fluorescent labelled nucleotides. PCR extension from the probe is blocked with a 3' phosphate. The cryptic plasmid target sequence may be amplified using primers such as CHF3-1 (5'GGGTTCGTTGTAGAGCCATGTCCTATCTTG (SEQ ID NO:33)) and CHR4-1 (5'CGCAGCTGCTGTAATCACCCAGTCGATAAA (SEQ ID NO:34)). The *Chlamydia* cryptic plasmid and a mismatched (C:A) positive amplification control may be reliably detected and identified on the basis of probe Tm (see table 1). The HYBCH2 probe is designed to hybridise to a section of the cryptic plasmid (Genbank Accession X07547) having a sequence of either:

```
HYBCHRC  5'CTTGGTATACATTTGCAGGCTTG    (SEQ ID NO: 35)
Mimic    5'CTTGGTATACATTTACAGGCTTG    (SEQ ID NO: 36)
```

Detection of the *Neisseria gonorrhoeae* cryptic plasmid may be performed by melt analysis using an oligonucleotide probe such as HYBNG (5'TCTGCFTCCGCFACGGCTTC (SEQ ID NO:58)), where F are fluorescent labelled nucleotides. PCR extension from the probe is blocked with a 3' phosphate. The cryptic plasmid target sequence may be amplified using primers such as NGF1 (5'ACTTTGGC-GATATTGCTCGG (SEQ ID NO:74)) and NGR1 (5'TAC-CGAGAACGAACGCGACA (SEQ ID NO:75)). The gonorrhoeae cryptic plasmid may be reliably detected and identified on the basis of probe Tm (table 1). The HYBNG probe is designed to hybridise to a section of the cryptic plasmid (Genbank Accession M10316) having a sequence of:

```
HYBNGRC   5'GAAGCCGTAGCGGAAGCAGA      (SEQ ID NO: 59)
```

Detection of the hexon gene in Adenovirus C and Adenovirus D strains may be performed by melt analysis using The oligonucleotides of the invention such as HyBAdC (5'GACGTGGFCCGTGFGCACCAGCCT (SEQ ID NO:68)) and HyBAdD (5'GACGTGGFCAGAGFGCAC-CAGCCT (SEQ ID NO:71)), where F are fluorescent labelled nucleotides. PCR extension from these probes is blocked with 3' phosphates. The hexon target sequence may be amplified using primers such as ADRJC1 (5'GACATGACTTTCGAG-GTCGATCCCATGGA (SEQ ID NO:76)) (Elnifro et al, 2000) and PB00432 (5'GCCGAGAAGGGCGTGCGCAG-GTA (SEQ ID NO:77)) obtained from the VirOligo database. The Adenovirus strains may be reliably detected and identified on the basis of probe Tm (see table 1). The HyBAdC probe is fully complementary to Adenovirus C sequence and exhibits both C:T and T:T mismatches when hybridised to Adenovirus D sequence. The HyBAdD probe is fully complementary to Adenovirus D sequence and exhibits both A:G and A:A mismatches when hybridised to Adenovirus C sequence. Larger variations in probe melting temperature are obtained with the HyBAdC probe (table 1). The Adenovirus probes are designed to hybridise to a section of the hexon gene (Genbank Accession AJ293905) having a sequence of either:

```
HyBAdCRC 5'AGGCTGGTGCACACGGACCACGTC    (SEQ ID NO: 69)
HyBAdDRC 5'AGGCTGGTGCACTCTGACCACGTC    (SEQ ID NO: 70)
```

Detection of the Influenza A matrix gene may be performed by melt analysis using an oligonucleotide probe such as HYBINF (5'GGGAFCCAAAFAACATGGACAGAGCT (SEQ ID NO:66)), where F are fluorescent labelled nucleotides. PCR extension from the probe is blocked with a 3' phosphate. The matrix target sequence may be amplified using primers such as INFA-1 (5'GGACTGCAGCGTA-GACGCTT (SEQ ID NO:78)) and FLU-4 (5'ATTTCTTTG-GCCCCATGGAATGT (SEQ ID NO:79)). Since Influenza is an RNA virus, a reverse transcription (RT) step is required prior to target amplification. cDNA production, PCR amplification and target detection may all be performed in a single reaction vessel using a Roche one-step LightCycler RT-PCR kit. Influenza A may be reliably detected and identified on the basis of probe Tm (table 1). The HYBINF probe is designed to hybridise to a section of the matrix gene (Genbank Accession AY130766) having a sequence of:

```
INFRC  5'AGCTCTGTCCATGTTATTTGGATCCC   (SEQ ID NO: 67)
```

Detection of the *Streptococcus pneumoniae* pneumolysis gene may be performed by melt analysis using an oligonucleotide probe such as SP1 (5'GGGGTCTFCCACTFG-GAGAAAGCTATC (SEQ ID NO:64)), where F are fluorescent labelled nucleotides. A single-labelled version of the *Streptococcus* probe was also investigated (5'GGGGTCTFC-CACTTGGAGAAAGCTATC (SEQ ID NO:80)). PCR extension from the probe is blocked with a 3' phosphate. The pneumolysin target sequence may be amplified using primers such as SPF2 (5'CTTGCGGTTGATCGTGCTCCGATGAC (SEQ ID NO:81)) and SPR2 (5'CATTATTGACCTGACCAT-AATCTTGATGCC (SEQ ID NO:82)). *Streptococcus pneumoniae* may be reliably detected and identified on the basis of probe Tm (table 1). The SP1 probe is designed to hybridise to a section of the pneumolysin gene (Genbank Accession X52474) having a sequence of:

```
SP1RC  5'GATAGCTTTCTCCAAGTGGAAGACCCC  (SEQ ID NO: 65)
```

Detection of the Factor II (G20210A) SNP may be performed by melt analysis using an oligonucleotide probe such as HYBFII (5'GCATFGAGGCTCGCFGAGAGTC (SEQ ID NO:115)), where F are fluorescent labelled nucleotides and the underlined nucleotide is the position of polymorphism. PCR extension from the probe is blocked with a 3° phosphate.

The Factor II target sequence may be amplified using primers such as FIIF2 (5'CTGGGCTCCTGGAACCAATC (SEQ ID NO:118)) and FIIR1 (5'GCTGCCCATGAATAG-CACTGG (SEQ ID NO:119)). The fully complementary and mismatched (C:A) alleles may be reliably detected and identified on the basis of probe Tm (see table 1). The HYBFII probe is designed to hybridise to a section of the factor II gene (Genbank Accession AF493953) having a sequence of either:

```
FIIRC    5'GACTCTCAGCGAGCCTCAATGC     (SEQ ID NO: 116)
FIIMM    5'GACTCTCAGCAAGCCTCAATGC     (SEQ ID NO: 117)
```

Detection of the MTHFR (A1928C) SNP may be performed by melt analysis using an oligonucleotide probe such as HYBA1928C (5'GACCAGFGAAGCAAGFGTCTTTG (SEQ ID NO:112)), where F are fluorescent labelled nucleotides and the underlined nucleotide is the position of polymorphism. PCR extension from the probe is blocked with a 3' phosphate. The A1928C target sequence may be amplified using primers such as 1928F (5'CCCAAGGAGGAGCT-GCTGAA (SEQ ID NO:120)) and 1928R (5° CCATTCCG-GTTTGGTTCTCC (SEQ ID NO:121)). The fully complementary and mismatched (C:T) alleles may be reliably detected and identified on the basis of probe Tm (see table 1). The HYBA1928C probe is designed to hybridise to a section of the 5,10-methylenetetrahydrofolate reductase gene (Genbank Accession NM_005957) having a sequence of either:

FIIRC 5'CAAAGACACTTGCTTCACTGGTC    (SEQ ID NO: 113)

FIIMM 5'CAAAGACACTTTCTTCACTGGTC    (SEQ ID NO: 114)

Detection of the MTHFR(C677T) SNP may be performed by melt analysis using an oligonucleotide probe such as HYBMTH (5 GTCFGCGGGAGCCGAFTTCATC (SEQ ID NO:112)), where F are fluorescent labelled nucleotides and the underlined nucleotide is the position of polymorphism. PCR extension from the probe is blocked with a 3° phosphate. The C677T target sequence may be amplified using primers such as MTHF2 (5'CTGACCTGAAGCACTTGAAGGAG (SEQ ID NO:122)) and MTHR2 (5'GCGGAAGAATGTGT-CAGCCTCAAAG (SEQ ID NO:123)). The fully complementary and mismatched (C:A) alleles may be reliably detected and identified on the basis of probe Tm (see table 1). The HYBMTH probe is designed to hybridise to a section of the 5,10-methylenetetrahydrofolate reductase gene (Genbank Accession NM_005957) having a sequence of either:

FIIRC 5'CAAAGACACTTGCTTCACTGGTC    (SEQ ID NO: 110)

FIIMM 5'CAAAGACACTTTCTTCACTGGTC    (SEQ ID NO: 129)

Example 3

Direct Analysis of Saliva Samples

Figure 2:
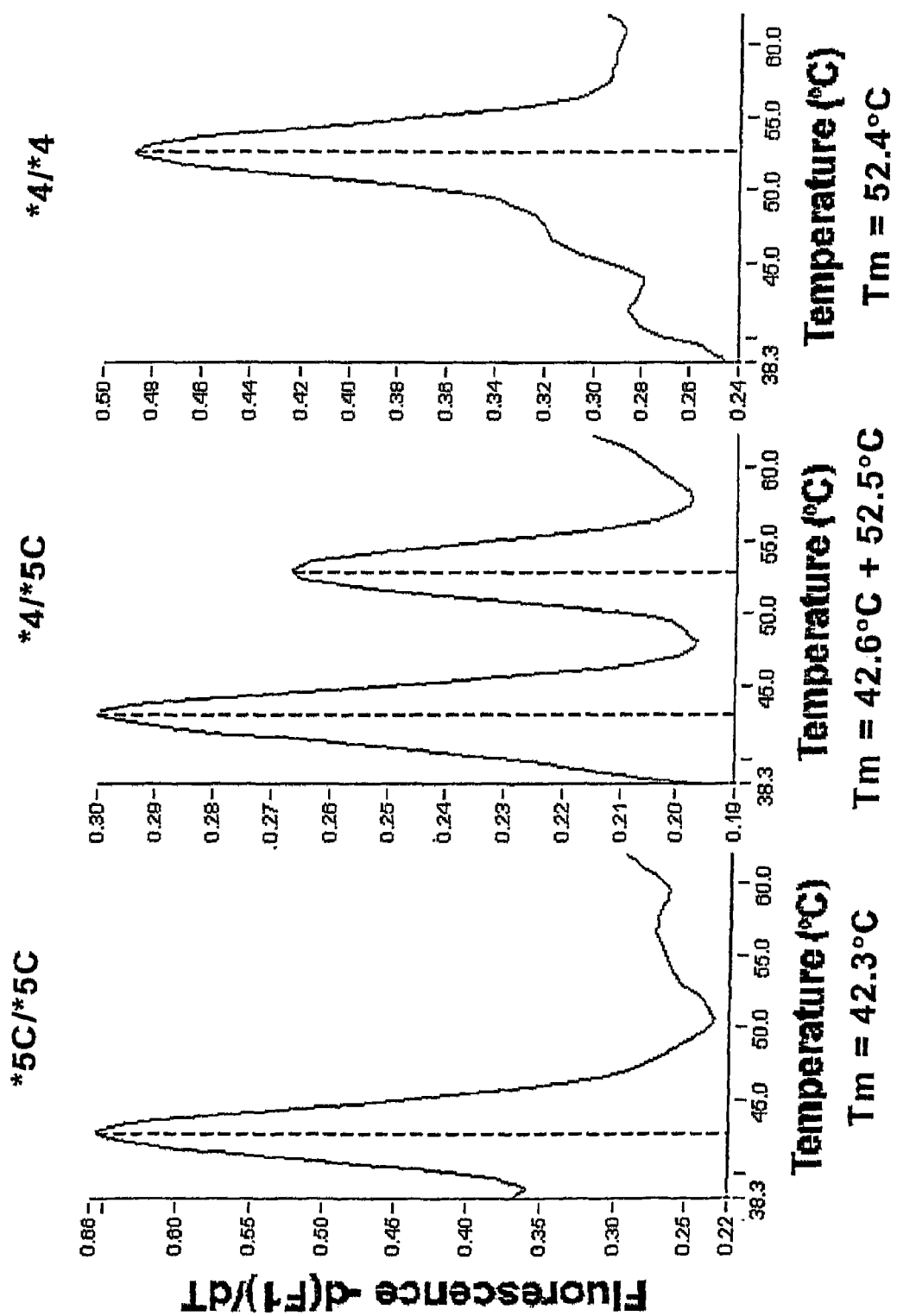

A series of saliva samples were analysed with the MTHFR (A1928C) primers and probe, as described above, without DNA purification. Mouthwashes, which comprise approximately 50% saliva in water, were included directly in the assays. Buccal swabs expressed in water may also analysed directly. The HYBA1928C probe generates single melt peaks with Tms of approximately 51.5° C. and 61° C. with samples homozygous for the A and C alleles respectively (FIG. 2). Saliva samples that are heterozygous for the A and C alleles are clearly identified by the generation of both 51.5° C. and 61° C. peaks. Detection and identification of polynucleotide targets have also been achieved directly from blood without the requirement for DNA purification.

Example 4

Rapid Target Detection Using Dual and Triple-Labelled Probes

Figure 4:
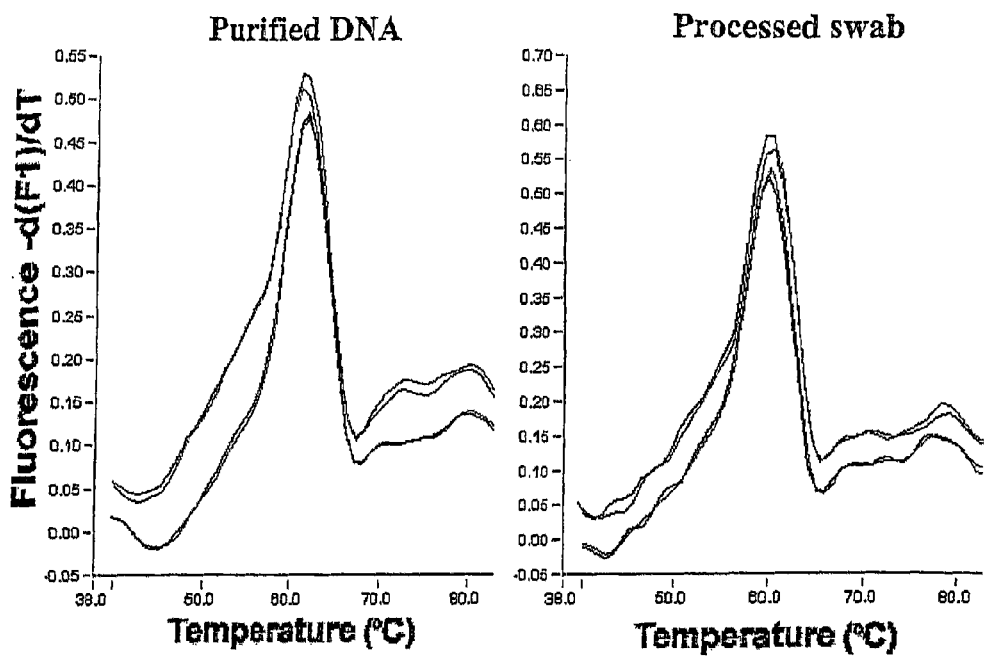
Figure 4:
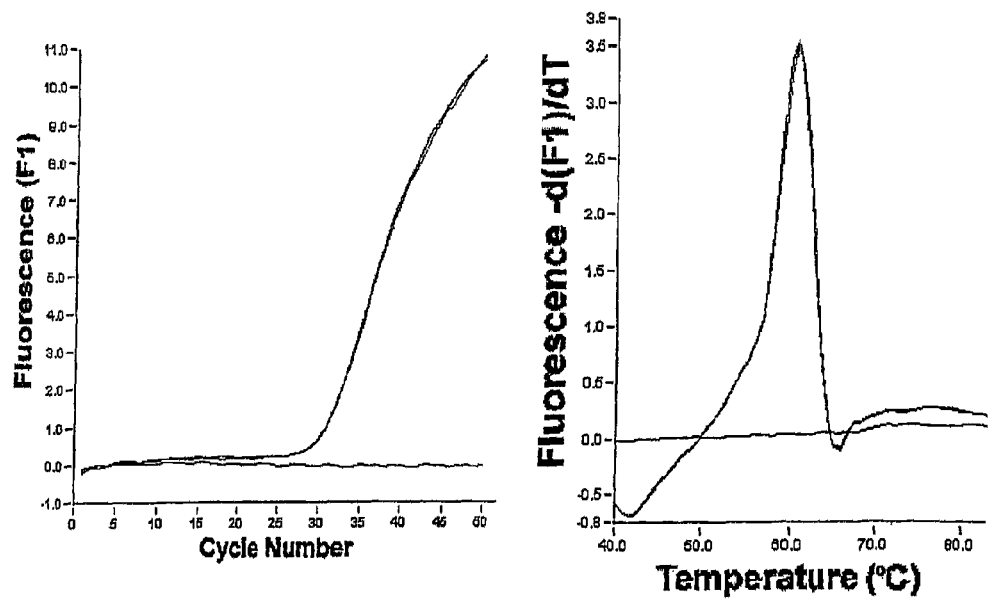

*Chlamydia* cryptic plasmid targets may be amplified using primers CHF3-1 (SEQ ID NO:33) and CHR4-1 (SEQ ID NO:34). Assays employ 3-stage LightCycler protocols consisting of an initial denaturation (95° C. 1 min) followed by 50 cycles of PCR comprising denaturation (95° C. 5 s), primer annealing (55° C. 10 s) and extension of products (72° C. 10 s). Amplified target is detected and characterised through the inclusion of HYBCH (SEQ ID NO:61) or HYBCH6 probes (SEQ ID NO:104) and melt curve analysis comprising denaturation (95° C. 0 s), cooling (35° C. 30 s) and a slow heat towards 95° C. using a 0.2° C./s transition rate. In the presence of *Chlamydia* DNA, the HYBCH and HYBCH6 probes generate clear melt peaks with Tms of approximately 56° C. and 60.5° C. respectively. The assays using the oligonucleotides of the invention have detected the presence of *Chlamydia* in purified DNAs, neat urines, processed (Becton Dickinson, Oxford, U.K.) urines & swabs and liquid samples pipetted directly from swabs (FIG. 4).

Figure 5:
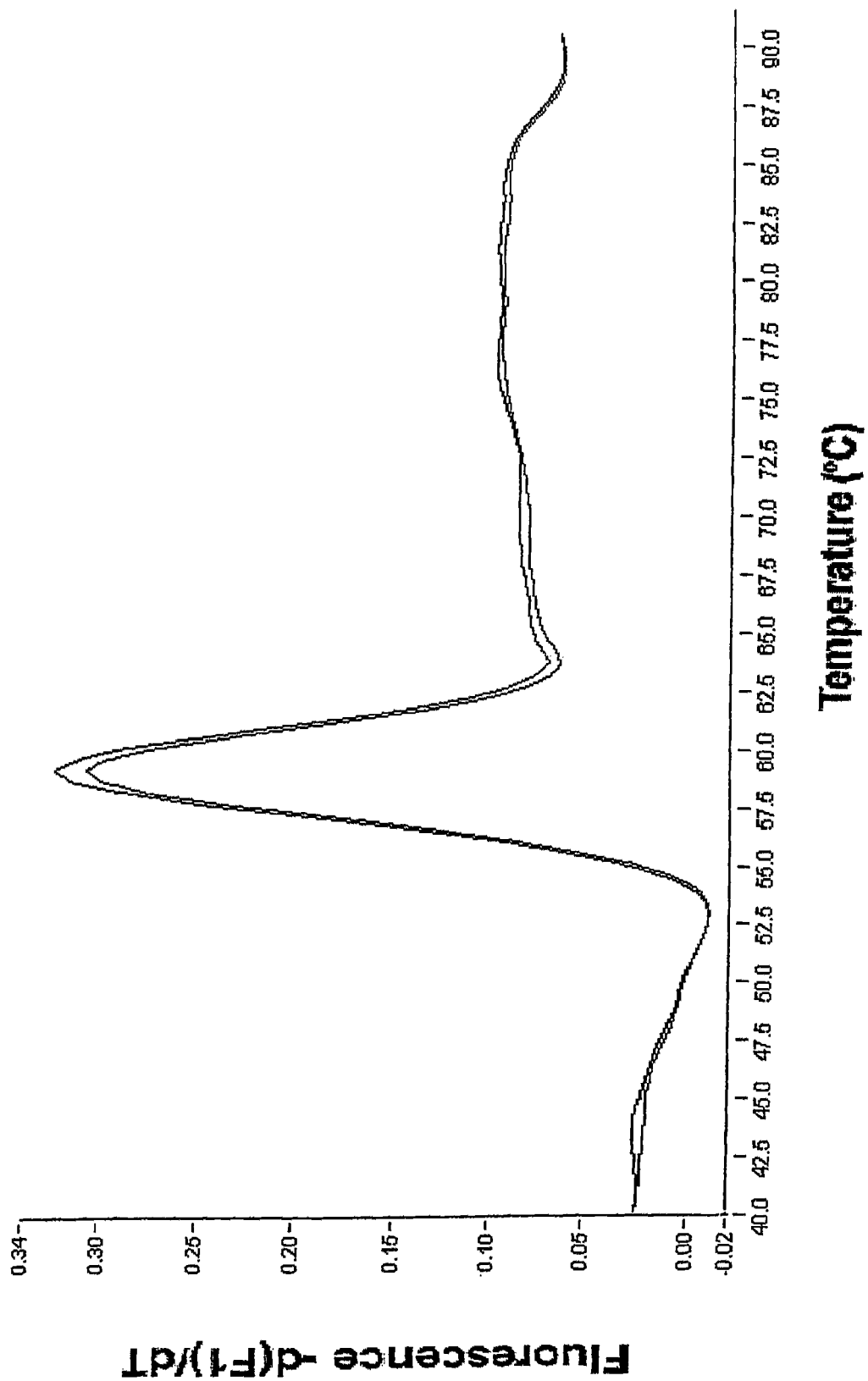

Gonorrhoeae plasmid targets are amplified using primers NGF1 (SEQ ID NO:74) and NGR1 (SEQ ID NO:75). Assays employ 3-stage LightCycler protocols consisting of an initial denaturation (95° C. 1 min) followed by 50 cycles of PCR comprising denaturation (95° C. 5 s) primer annealing (55° C. 10 s) and extension of products (72° C. 10 s). Amplified target is detected and characterised through the inclusion of HYBNG probe (SEQ ID NO:58) and melt curve analysis comprising denaturation (95° C. 0 s), cooling (35° C. 30 s) and a slow heat towards 95° C. using a 0.2° C./s transition rate. In the presence of Gonorrhoeae DNA, the HYBNG probe generates clear melt peaks with Tms of approximately 59° C. (FIG. 5).

Example 5

Comparison of Single-Labelled and Dual-Labelled Probes

Figure 6:
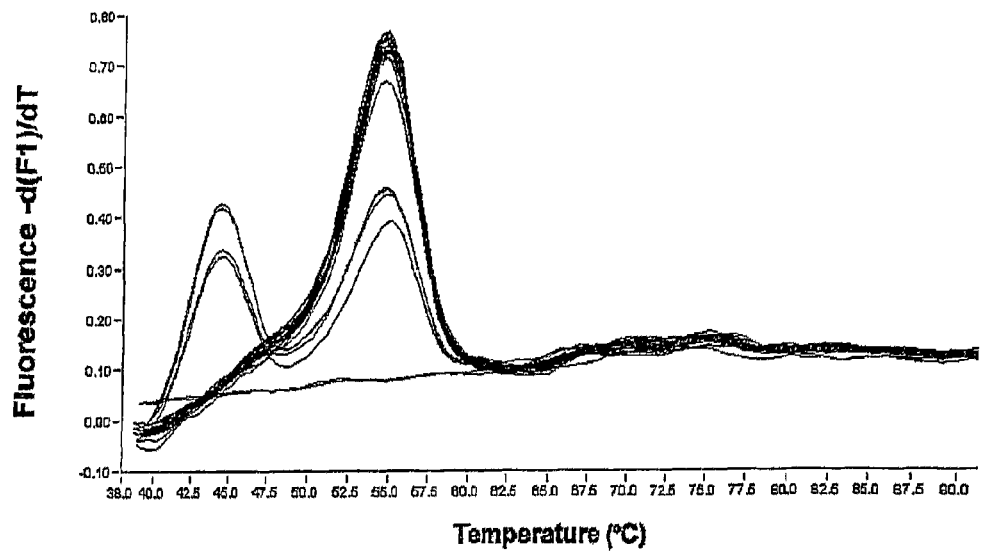
Figure 6:
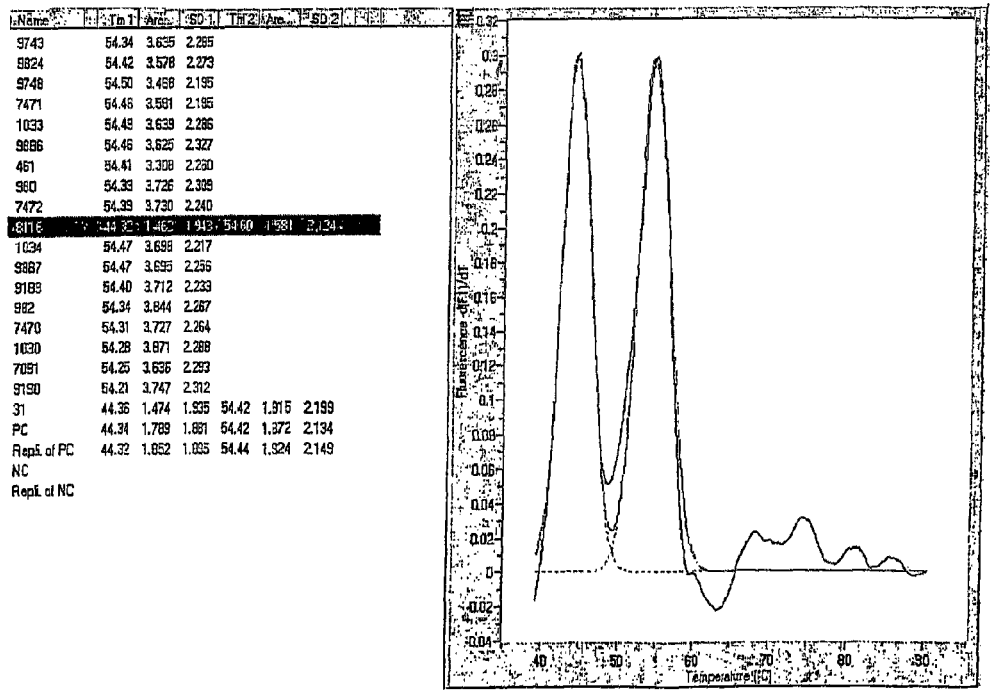

Factor V targets are amplified directly from saliva samples, without DNA purification, using primers FVF1.3 (SEQ ID NO:22) and FVR3.5 (SEQ ID NO:23). Assays employ 2-stage LightCycler protocols consisting of an initial denaturation (95° C. 1 min) followed by 50 cycles of PCR comprising denaturation (95° C. 1 s) and combined annealing/extension (65° C. 5 s) phases. Amplified target is detected and characterised through the inclusion of FVG1 (SEQ ID NO:21) or FVG11 (SEQ ID NO:60) oligonucleotide probes and melt curve analysis comprising denaturation (95° C. 0 s), cooling (35° C. 30 s) and a slow heat towards 95° C. using a 0.2° C./s transition rate. Factor V assays may be completed in as little as 16 minutes. Homozygous wild type samples yield single melt peaks possessing Tms of approximately 59° C. and 55° C. when FVG1 and FVG11 probes are employed respectively. Homozygous mutant samples generate single melt peaks possessing Tms of approximately 49.5° C. and 45° C. when FVG1 and FVG11 probes are employed respectively. Heterozygous Factor V samples yield both 59° C. and 49.5° C. melt peaks when the single-labelled FVG1 probe is used and generate both 55° C. and 45° C. peaks when the dual-labelled FVG11 probe is employed (FIG. 6). The assays function efficiently with purified DNAs, swab samples and buccal washes. Over 450 genomic samples have been reliably typed, with respect to the Factor V polymorphism, using the FVG1 and FVG11 probes.

Figure 3:
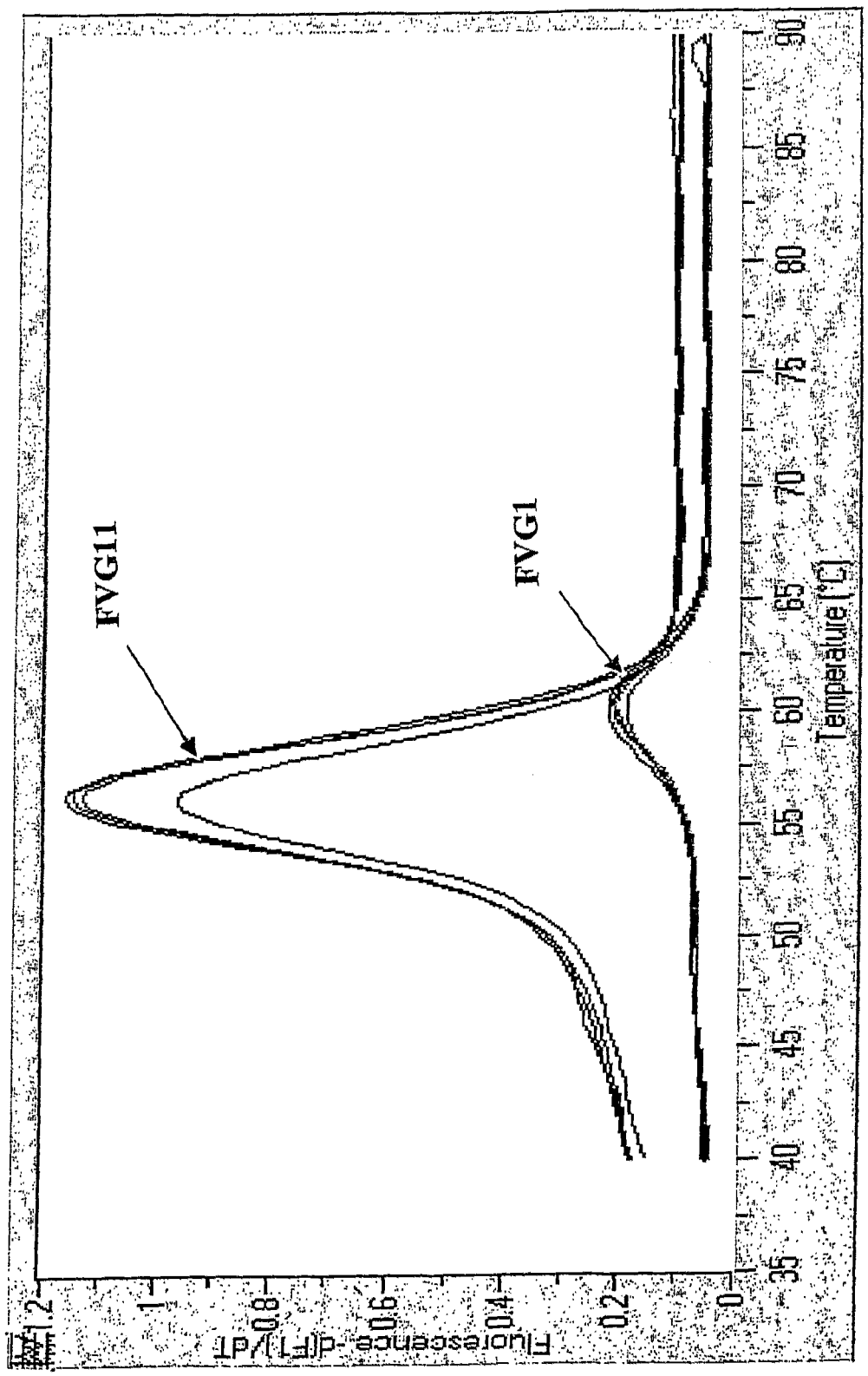
Figure 11:
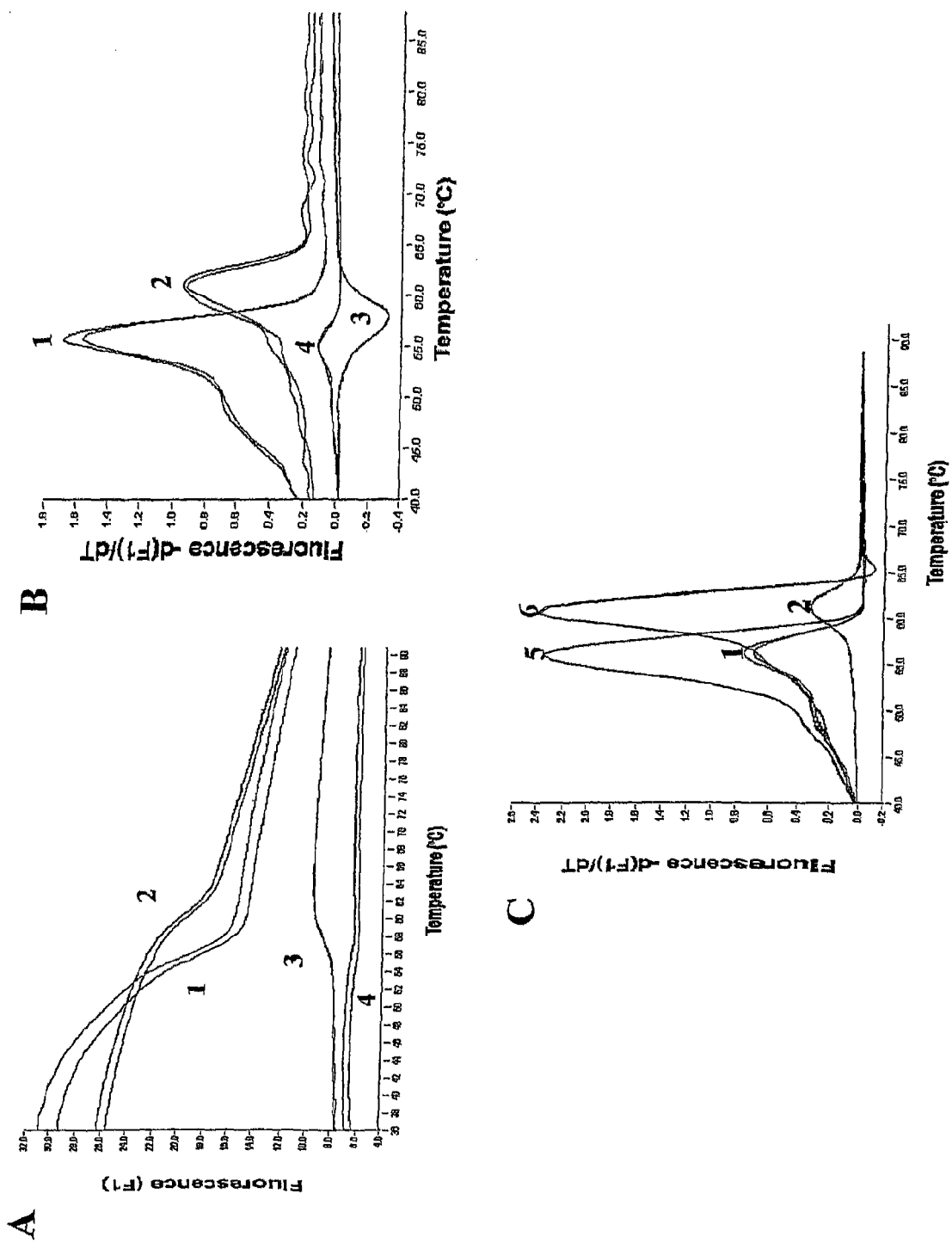

The dual-labelled probe does exhibit higher levels of background signal, compared with the single-labelled probe, when single-stranded. However, the dual-labelled FVG11 probe yields melt peaks that are approximately four times the size of those generated with the single-labelled FVG1 probe which is significantly greater than would be expected if the affect of the additional fluorophore was simply additive. The additional fluorophore in FVG11 reduces the Tm of the probe by approximately 4.5° C. compared with the single-labelled FVG1 probe (FIG. 3). A similar reduction in Tm is observed with the single-labelled HYBCH2 (SEQ ID NO:32) and dual-labelled HYBCH (SEQ ID NO:61) *Chlamydia* probes (FIG. 11).

Example 6

Probe Signal-to-Noise

The amount of fluorescence emission from The oligonucleotides of the invention was measured in single-stranded and double-stranded states to investigate the affect of probe sequence, fluorophore placement and dual/triple-labelling.

Figure 7:
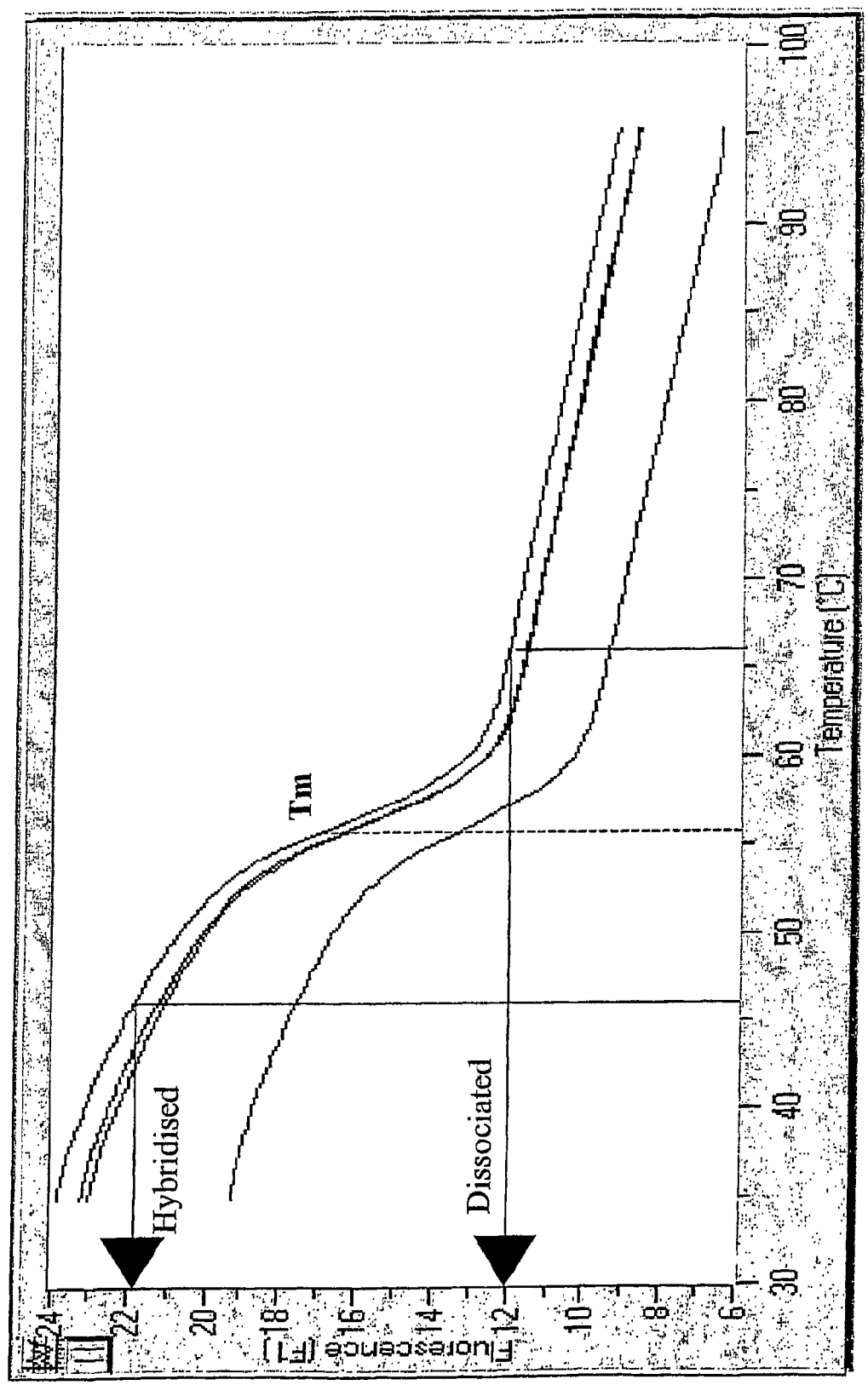

150 nM of probe was typically hybridised to 150 nM of fully complementary oligonucleotide, in TaKaRa buffer, to determine the signal-to-noise ratio of The oligonucleotides of the invention. Fluorescence measurements were made using a LightCycler melting curve protocol comprising denaturation (95° C. 0 s), cooling (35° C. 30 s) and a slow heat to 95° C. using a 0.2° C./s transition rate. Fluorescence values were obtained from melt curves at temperatures of probe Tm plus and minus 10° C. for dissociated and hybridised states respectively (FIG. 7). Fluorescence measurements were made over this defined temperature range in an attempt to remove some of the affects that temperature has on the amount of emission. The hybridised and dissociated fluorescence values provide a measure of signal-to-noise ratio and an indication of the affect of probe hybridisation on emission (table 2), where signal-to noise ratio is calculated as hybridised signal divided by dissociated signal. Probe signal-to-noise ratios have been found to be highly reproducible and exhibit low run-to-nm and instrument-to-instrument variation.

The single-labelled FVG1 probe (SEQ ID NO:21) possesses a Tm of approximately 59° C. when hybridised to fully complementary target sequence (SEQ ID NO:24) and exhibits fluorescence levels of 8 and 6 (arbitrary LightCycler fluorescence units) at 49° C. and 69° C. respectively. The dual-labelled FVG11 probe (SEQ ID NO:60)) possesses a Tm of approximately 55° C. when hybridised to the fully complementary target sequence and exhibits fluorescence levels of 21.8 and 12 at 45° C. and 65° C. respectively. The signal-to-noise ratios of single and dual-labelled factor V probes are calculated as 1.33 and 1.82 respectively.

Figure 8:
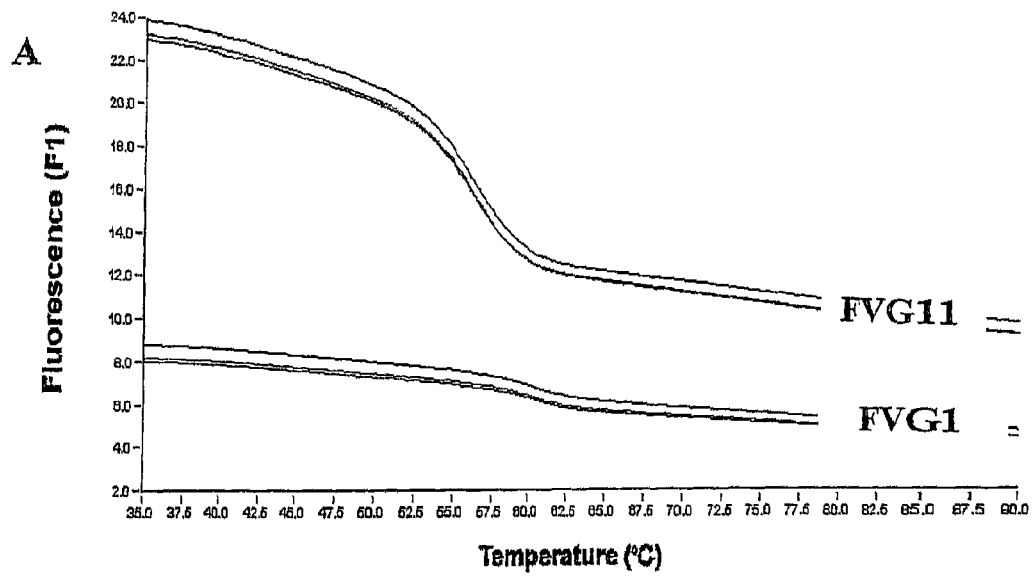
Figure 8:
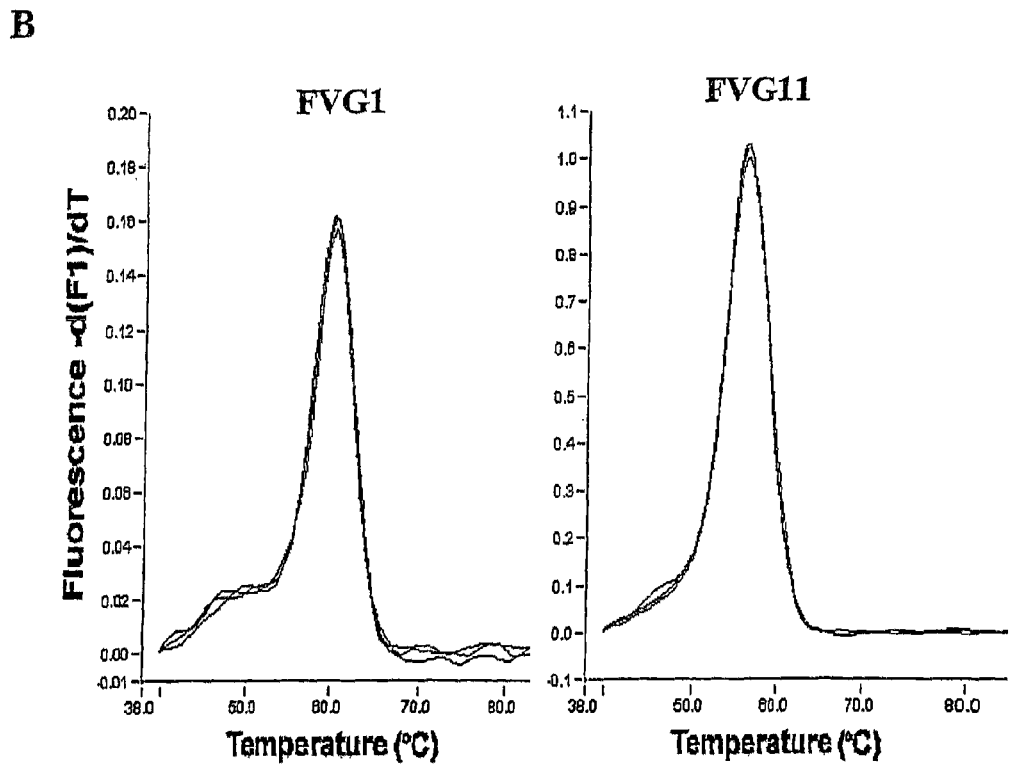
Figure 9:
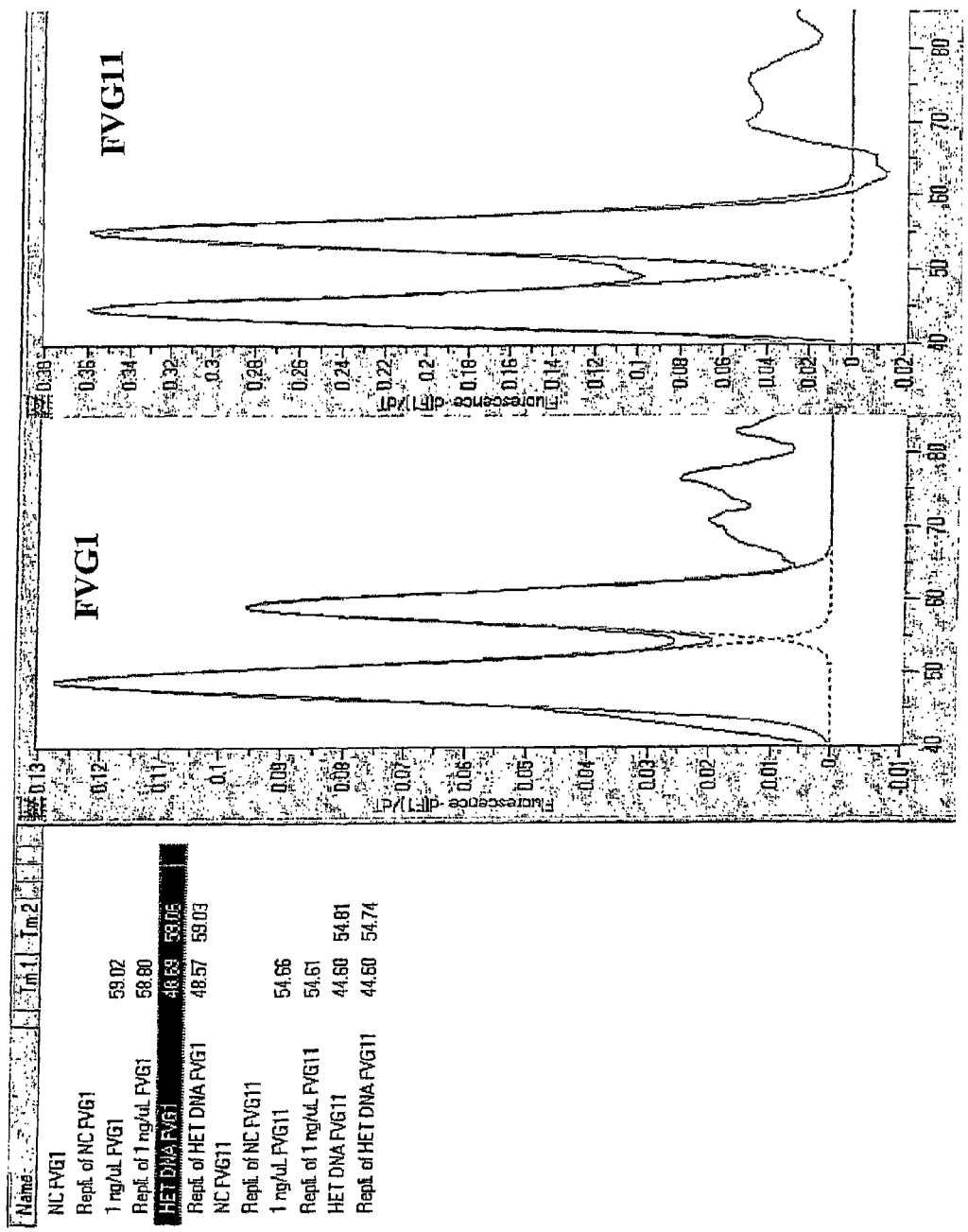

Dual-labelled probes may exhibit higher levels of background fluorescence noise compared with equivalent single-labelled probes. However, despite the elevated background noise, dual-labelled probes consistently yield considerably greater signal-to-noise ratios and melt peak heights. With oligonucleotide targets, single-labelled probes have yielded emission increases between 20% and 92%. Whereas, dual-labelled probes have demonstrated fluorescence increases between 71% and 199%. Hybridisation of 150 nM FVG11 probe to the complementary oligonucleotide FVG (SEQ ID NO:24) results in approximately two times more background fluorescence (at 90° C.) than hybridisation of 150 nM FVG1 probe (FIG. 8). However, the background correction function of the LightCycler software demonstrates that the dual-labelled peak is approximately five times greater in height than the equivalent single-labelled probe peak with oligonucleotide targets (FIGS. 3 & 8). Background corrected data derived from heterozygous Factor V carrier DNA samples demonstrates that the dual-labelled probe yields two melt peaks that are each approximately three times the height of peaks generated with single-labelled probe in target amplification assays (FIG. 9).

Fluorophores Flanked by Guanine Nucleotides

Given that guanine bases are efficient quenchers of fluorescence, fluorophores flanked by G's may be expected to be efficiently quenched when probes are in the dissociated state and fluorescence emission may be expected to increase considerably upon probe hybridisation. All probes containing internal fluorophores adjacent to G's (5', 3' or both positions) have demonstrated signal enhancement upon target hybridisation (table 2). The C9*2C (SEQ ID NO:55), 136A (SEQ ID NO:83) and HYBA1928C (SEQ ID NO:112) oligonucleotide probes are good examples of probes with fluorescent labels positioned between two G nucleotides. The signal-to-noise ratio of C9*2C is comparable to the 2D64C* probe (SEQ ID NO:51), whose fluorophore is adjacent to only one G but is very G rich in general. The A/T rich DdeFL1*4 probe (SEQ ID NO:6) also exhibits a similar signal-to-noise ratio and possesses a single G nucleotide adjacent to the fluorophore. The placement of fluorophores adjacent to G residues are more likely, although not necessary, to generate large peak heights and signal-to-noise ratios. The absence of G residues at suitable locations within the probe is not problematic as probes yield efficient hybridisation signals when fluorophores are placed in all sequence environments. Although this example shows single-labelled oligonucleotides, as well as oligonucleotides of the invention, it nevertheless demonstrates that it is the independence of target sequence, and not an interaction between fluorophores, that causes the sequence independent enhancement of fluorescence upon target hybridisation.

Fluorophores Flanked by Cytosine Nucleotides

If guanine residues in target sequences have the ability to cause fluorescence quenching, emission from fluorophores flanked by C residues may be expected to decrease upon target hybridisation. However, all oligonucleotide probes with fluorophores adjacent to C residues, such as HYBNG (SEQ ID NO:58), 171R (SEQ ID NO:85), C19m1A (SEQ ID NO:39), SCT1 (SEQ ID NO:26) and SP2 (SEQ ID NO:80), have demonstrated fluorescence enhancement upon probe hybridisation. Even highly C rich oligonucleotide probes, such as HEPB (SEQ ID NO:45) and FVG2 (5'GTATFC-CTCGCCTGTCCAG (SEQ ID NO:87)), emit higher levels of fluorescence when hybridised to targets than when single-stranded. Fluorescence enhancement upon probe hybridisation appears to be independent of the presence of guanine nucleotides in the target sequence, as predicted by molecular modelling, which indicates that fluorophores do not interact with duplex DNA.

Fluorophores Flanked by Adenine and Thymine Nucleotides

Oligonucleotide probes with fluorophores placed between A and T residues also exhibit enhancement of fluorescence emission upon target hybridisation. The NAT2*6 (SEQ ID NO:88), HYBNAT3S (SEQ ID NO:16) and FVG1 (SEQ ID NO:21) probes are good examples of probes whose fluorophore-labelled bases are neighboured by A and T nucleotides. An artificially constructed PolyT probe (5'TTTTTTTTTTTFTTTTTTTTTTT (SEQ ID NO:37)) displays increased levels of fluorescence emission when hybridised to target sequences, compared with the single-stranded state, despite the complete absence of G nucleotides in both probe and target strands. These oligonucleotides contain a single fluorophore and so are not oligonucleotides of the invention. Nevertheless, they demonstrate the sequence independence of the fluorescent nature of the probes.

Signal Strength and Sequence Context of Fluorophore Attachment

The data in table 2 demonstrates that probe functionality is not reliant on the presence of guanine residues within the probe or target sequences. There is, however, a possible association between the higher signal-to-noise ratios and the presence of Gs at probe positions immediately neighbouring the fluorophore. For single-labelled probes, many of the large signal-to-noise ratios are derived from probes with fluorophores flanked by guanine bases. However, the largest single-labelled signal-to-noise ratio was obtained from an oligonucleotide possessing a fluorophore flanked by A and C nucleotides (SEQ ID NO:85).

Probes with fluorophores flanked by A, C and T bases have yielded larger signals than several probes with G nucleotides directly adjacent to the fluorophore-labelled base. Furthermore, all single, dual, and multiple-labelled oligonucleotide probes have exhibited enhanced levels of fluorescence emission upon target hybridisation irrespective of the sequence flanking the internal fluorophores. Therefore, whilst larger melt peaks may be obtained by placing fluorophore-labelled nucleotides adjacent to guanine residues, high quality melt peaks may be'obtained without the requirement for G residues at specific sites in the probe sequence. Although these oligonucleotides contain a single fluorophore, they demonstrate the sequence independence and also will assist in optimal spacing in certain sequence contexts.

Independence of Target Sequence

LightCycler melt curve analysis strongly suggests that the sequence of the target has little or no affect on the functionality of the oligonucleotide probes. If the fluorophores of the oligonucleotide probes project into solution upon hybridisation, such that they do not interact with duplex DNA, fluorophores may be positioned within highly C rich regions of the probe without being quenched by the G nucleotides of the target. All single and dual-labelled oligonucleotide probes designed to date exhibit enhanced levels of fluorescence upon hybridisation relative to the single-stranded state irrespective of probe sequence and the nucleotides flanking the fluorophore-labelled bases.

TABLE 2

Signal-to-noise ratios obtained from hybridising 150 nM oligonucleotide probes to fully complementary oligonucleotides. Sequence identification numbers for probes and targets are provided. Signal-to-noise ratios are ranked from lowest to highest. Melt curves were all generated using a single LightCycler instrument (LC2).

| Probe | SEQ IDs | Sequence | Signal-to-noise ratio |
|---|---|---|---|
| NAT2*6 | 88, 89 | CTTCAAFTGTTTGAGGTTCAAG | 1.26 |
| polyT | 37-38 | TTTTTTTTTTFTTTTTTTTTTT | 1.27 |
| C19m1A | 39-40 | GATTATTFCCCAGGAACCC | 1.29 |
| HYBNAT3S | 16-17 | CTTTAAAATACAFTTTTTATTATTA | 1.28 |
| C19m2G | 42-43 | TACCFGGATCCAGGGGGTG | 1.33 |
| FVG1 | 21, 24 | CTGTAFTCCTCGCCTGTCC | 1.33 |
| HYBCH8 | 106, 103 | CAAGCCTGCAAATGTAFACCAAG | 1.33 |
| HEPB | 45-46 | AAGAACTCCCFCGCCTCGCA | 1.36 |
| SP2 | 80, 65 | GGGGTCTFCCACTTGGAGAAAG | 1.36 |
| PJ18S | 47-48 | GAGACGAACAACFGCGAAAGC | 1.42 |
| HYBCH2 | 32, 35 | CAAGCCTGCAAAFGTATACCAAG | 1.44 |
| FVG1ALT | 101, 24 | CTGTATTCCTCGCCFGTCC | 1.48 |
| FVG1ALT2 | 128, 24 | CTGTATTCCFCGCCTGTCC | 1.50 |
| NAT2*5 | 124, 4 | GAGAGGAATCFGGTACTTGGACC | 1.52 |
| BamFL1*7 | 11, 14 | CCTGGTGAFGAATCCCTTAC | 1.53 |
| HYBCH7 | 105, 103 | CAAGCCFGCAAATGTATACCAAG | 1.54 |
| HSV1 | 49-50 | GGACACCGGCGCFACTTCACCT | 1.56 |
| DdeFL1*4 | 6, 9 | GAAGTGCFGAAAAATATATTTAAG | 1.56 |
| 2D64C* | 51-52 | GGGCGFCCTGGGGTG | 1.63 |
| C9*2T | 54-55 | CATTGAGGACTGFGTTCAAG | 1.63 |
| C9*2C | 56-57 | CATTGAGGACCGFGTTCAAG | 1.67 |
| HYBSTR | 91, 86 | GGTGGATAGAFAGATAGAFAGATAGATAGA TAGATAGATAGATAGATAGATAGATAGATA | 1.71 |
| HYBCH10 | 108, 103 | CAAGCCFGCAAATGTAFACCAAG | 1.74 |
| HYBNG | 58-59 | TCTGCFTCCGCFACGGCTTC | 1.78 |
| FVG11 | 60, 24 | CTGTAFTCCTCGCCFGTCC | 1.82 |
| 136A | 83-84 | GGGAAGFGCCATGAGCAG | 1.83 |
| HYBMTH | 109-110 | GTCFGCGGGAGCCGAFTTCATC | 1.84 |
| HYBCH | 61, 35 | CAAGCCFGCAAAFGTATACCAAG | 1.91 |
| HYBCH9 | 107, 103 | CAAGCCTGCAAAFGTAFACCAAG | 1.92 |
| 171R | 85-86 | CAGTGGAFCGGTATAGTAAC | 1.92 |
| G08377 | 62, 63 | ATGGGAAFGGGGAFCCAAATAA | 1.93 |
| SP1 | 64-65 | GGGGTCTFCCACTFGGAGAAAGCTATC | 1.94 |
| HYBINF | 66-67 | GGGAFCCAAAFAACATGGACAGAGCT | 1.95 |
| HYBMRSA | 99-100 | CGTAGFTACTGCGTFGTAAGACGTC | 2.07 |
| HYBA1928C | 112-113 | GACCAGFGAAGCAAGFGTCTTTG | 2.14 |
| HYBFII | 115-116 | GCATFGAGGCTCGCFGAGAGTC | 2.36 |
| HYBCH5 | 102-103 | CAAGCCFGCAAAFGTAFACCAAG | 2.38 |
| HYBCH6 | 103-104 | GTAAFCAAGCCFGCAAAFGTATACCAAG | 2.38 |
| HYBAdC | 68-69 | GACGTGGFCCGTGFGCACCAGCCT | 2.88 |
| HYBCH11 | 126, 103 | GTAAFCAAGCCFGCAAAFGTAFACCAAG | 2.90 |
| HYBAdD | 70-71 | GACGTGGFCAGAGFGCACCAGCCT | 2.99 |
| FVG111 | 127, 24 | CTGTAFTCCFCGCCFGTCC | 3.14 |

Measurement of UV-visible absorption and fluorescence spectra (Marks et al (2005)) demonstrates that there is a blue shift of approximately 4 nm and an increase in intensity on hybridisation of the oligonucleotide probes to complementary target sequences. The fluorescence properties of free FAMCAP dye are more like those of the probe/target duplex. Incorporation of FAMCAP into DNA probe constructs causes a red shift in the $\lambda_{max}$ of excitation and emission. The red shift suggests a possible interaction of the fluorophore with ssDNA, which may include π-π stacking interactions between the dye and the DNA bases. The results of Marks et al, also suggest that fluorophores do not interact with the double-stranded DNA by either intercalation or groove binding since these interactions would cause a strong red shift upon hybridisation. Therefore, there may be an interaction between the fluorophore and the bases of the single-stranded probe DNA that causes fluorescence quenching. This interaction between fluorophore and probe DNA is removed upon target hybridisation such that the dye projects into solution and fluorescence is enhanced. This mechanism of fluorescence enhancement is not expected to operate with terminally labelled probes since base stacking can occur on only one side of fluorophore. The data indicates that oligonucleotide probe fluorescence increases are caused by the removal of quenching rather than the enhancement of fluorescence. This model of the probe functionality also supports our proposition that the probe signals are independent of the target sequence, such that fluorophores may be positioned even within C rich regions and still exhibit enhanced levels of fluorescence upon target hybridisation.

Example 7

Peak Heights

The peak heights of single, dual and triple-labelled probes were also measured to investigate the affect of probe sequence, fluorophore placement and multiple fluorophores. Peak height measurements are slightly less reliable than signal-to-noise ratios for probe comparisons due to run-to-run and instrument-to-instrument variations. However, melt peaks generated in a single LightCycler experiment may be employed to reliably compare probe sequences. 150 nM of probe was typically hybridised to 150 nM of fully complementary oligonucleotide in TaKaRa buffer. Fluorescence measurements were made using a LightCycler melting curve protocol comprising denaturation (95° C. 0 s), cooling (35° C. 30 s) and a slow heat to 95° C. using a 0.2° C./s transition rate. Melt peak data obtained only with LightCycler software version 3.5 have been included in table 3. Version 3.01 of the LightCycler software required the user to set the fluorescence gain manually. Whereas software version 3.5 automatically determines fluorescence levels relative to the sample that exhibits the highest level of emission. All The oligonucleotides of the invention exhibit positive melt peaks when –dF/dT is plotted on the y-axis against temperature on the x-axis, irrespective of the probe and target sequences and the position of G's within them. The placement of single fluorophores, in the Factor V probing sequence, between A and T bases (FVG1) and between C and G bases (FVG1ALT) yields melt peaks of approximately equal height. The dual-labelled Factor V probe (FVG11) yields melt peaks that are approximately four times the height of those generated with the two single-labelled probes FVG1 and FVG1ALT (table 3). The sum of the single-labelled peak heights is less than that exhibited by the dual-labelled probe. Furthermore, employing 75 nM or 150 nM of both single-labelled probes in a single reaction vessel also results in melt peaks that are smaller than those generated by the dual-labelled oligonucleotide probes. An interaction between the fluorophore-labelled bases may be responsible for the enhanced signal-to-noise ratio and melt peak heights, making the dual-labelled probe greater than the sum of the two single-labelled probes. Further enhancement of signal is derived from triple-labelled probes (see below). The location and degree of separation of fluorophores within probes may affect the magnitude of fluorescence change upon target hybridisation and dissociation. Single-labelled probes possess reduced Tms compared with unlabelled oligonucleotides and dual-labelled probes consistently exhibit reduced Tms compared with equivalent single-labelled probes (table 1). Since the fluorophores are believed to project into solution upon target hybridisation, thereby not interacting with the duplex DNA, it is thought that fluorophores stabilise the single-stranded probe species rather than destabilise the duplex. Multiple-labelled probes are thought to stabilise single-stranded probe structures more than equivalent single-labelled oligonucleotide probes. Dual and multiple-labelled probes frequently exhibit lower levels of fluorescence noise than expected (table 5) due to the stabilised and efficiently quenched single-stranded structures. The reduced backgrounds and increased signals of dual and multiple-labelled probes give rise to larger peak heights and signal-to-noise ratios compared with equivalent single-labelled oligonucleotides.

Example 8

Comparison of Internal and Terminally Labelled Probes

Figure 10:
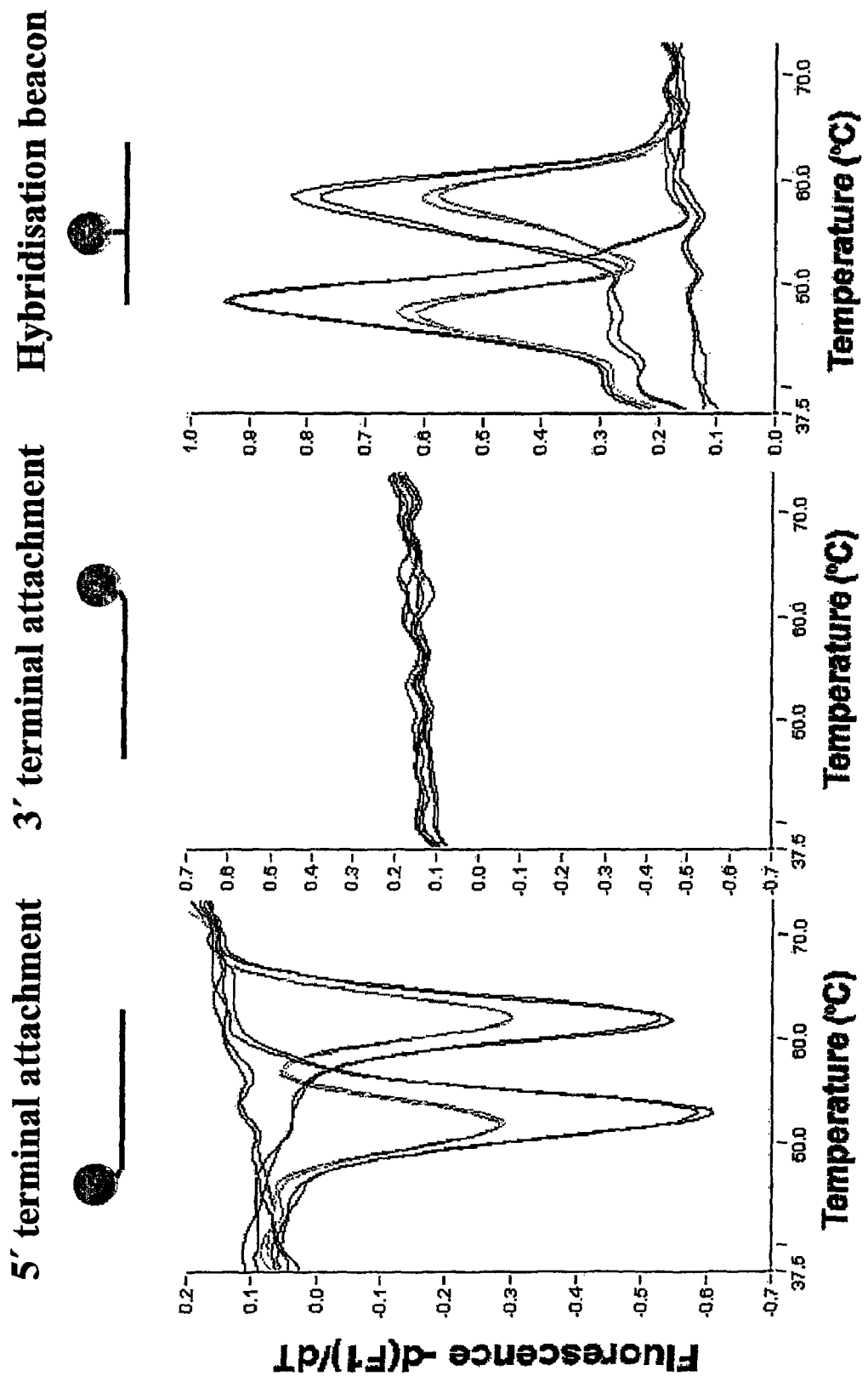

Factor V target sequences were amplified using primers FVF1 (5° GACTACTTCTAATCTGTAAGAGCAG SEQ ID NO:92)) and FVR3 (5'CCATTATTTAGCCAGGAGAC (SEQ ID NO:93)). Assays employed 3-stage LightCycler protocols consisting of an initial denaturation (95° C. 1 min) followed by 50 cycles of PCR comprising denaturation (95° C. 0 s), primer annealing (55° C. 10 s) and extension of products (72° C. 10 s). Amplified target was detected and characterised through the inclusion of FV3 (5'CTGTATTC-CTCGCCTGTCCF (SEQ ID NO:94)) or FV5 (5'FCTGTAT-TCCTCGCCTGTCC (SEQ ID NO:95)) terminally labelled probes and melt curve analysis comprising denaturation (95° C. 0 s), cooling (35° C. 30 s) and a slow heat towards 95° C. using a 0.1° C./s transition rate. The 3'-labelled FV3 probe was completely non-functional, yielding no peaks in melt curve analyses. Measuring probe emission spectra verified efficient oligonucleotide synthesis and fluorophore attachment. The FV5 probe, possessing a 5'-FAM attachment, exhibited a reduction in fluorescence emission upon target hybridisation. The FV5 probe generated inverted melt peaks in –dF/dT plots (FIG. 10) that allowed identification of homozygous and heterozygous samples. The inverted melt peaks derived from the 5'-labelled probe were of similar magnitude to the heights of peaks obtained from the single-labelled FVG1 Factor V probe (FIG. 10).

5'CTGTATTCCTCGCCTGTCC3 (Factor V probe sequence; SEQ ID No:140)
3'ATGGACATAAGGAGCGGACAGGTCC5' (Target sequence; SEQ ID No:141)

The 5'-labelled probe places the fluorophore in close proximity to G residues, at positions 0 and +1, upon hybridisation to the target sequence, explaining the observed reduction in fluorescence emission. The 3'-labelled probe also places the fluorophore in proximity with G residues, at positions 0 and −1, but fluorescence was neither enhanced nor quenched upon hybridisation.

TABLE 3

Melt peak heights obtained from hybridising 150 nM oligonucleotide probes to fully complementary oligonucleotides. Sequence identification numbers for probes and targets are provided. Peak heights are ranked from lowest to highest. All peaks were positive when the negative derivative of fluorescence with respect to temperature (-dF/dT) was plotted against temperature on the y and x axis respectively. All melt peaks were derived using a single LightCycler (LC2) to avoid instrument-to-instrument variability.

| Probe | SEQ ID | Sequence | Peak height (Version 3.5) |
|---|---|---|---|
| HSV1 | 49-50 | GGACACCGGCGCFACTTCACCT | 0.16 |
| polyT | 37-38 | TTTTTTTTTTTFTTTTTTTTTTT | 0.18 |
| C19m2G | 42-43 | TACCFGGATCCAGGGGGTG | 0.22 |
| FVG1ALT | 101, 24 | CTGTATTCCTCGCCFGTCC | 0.25 |
| FVG1 | 21-24 | CTGTAFTCCTCGCCTGTCC | 0.28 |
| NAT2*6 | 88-89 | CTTCAAFTGTTTGAGGTTCAAG | 0.3 |
| 2D64C* | 51-52 | GGGCGFCCTGGGGGTG | 0.3 |
| FVG1ALT2 | 128, 24 | CTGTATTCCFCGCCTGTCC | 0.31 |
| HYBCH8 | 105, 103 | CAAGCCTGCAAATGTAFACCAAG | 0.33 |
| DdeFL1*4 | 6, 9 | GAAGTGCFGAAAAATATATTTAAG | 0.34 |
| HYBNAT3S | 16-17 | CTTTAAAATACAFTTTTTATTATTA | 0.34 |
| PJ18S | 47-48 | GAGACGAACAACFGCGAAAGC | 0.36 |
| HEPB | 45-46 | AAGAACTCCCFCGCCTCGCA | 0.38 |
| C19m1A | 39-40 | GATTATTFCCCAGGAACCC | 0.43 |
| 136A | 83-84 | GGGAAGFGCCATGAGCAG | 0.45 |
| G08377 | 62-63 | ATGGGAAFGGGGAFCCAAATAA | 0.5 |
| HYBCH7 | 105, 103 | CAAGCCFGCAAATGTATACCAAG | 0.52 |
| HYBINF | 66-67 | GGGAFCCAAAFAACATGGACAGAGCT | 0.53 |
| C9*2T | 54-55 | CATTGAGGACTGFGTTCAAG | 0.59 |
| NAT2*5 | 124, 4 | GAGAGGAATCFGGTACTTGGACC | 0.64 |
| C9*2C | 56-57 | CATTGAGGACCGFGTTCAAG | 0.65 |
| BamFL1*7 | 11, 14 | CCTGGTGAFGAATCCCTTAC | 0.67 |
| 171R | 85-86 | CAGTGGAFCGGTATAGTAAC | 0.75 |
| HYBCH2 | 32, 35 | CAAGCCTGCAAAFGTATACCAAG | 0.8 |
| HYBNG | 58-59 | TCTGCFTCCGCFACGGCTTC | 0.8 |
| HYBSTR | 91, 86 | GGTGGATAGAFAGATAGAFAGATAGATAGA TAGATAGATAGATAGATAGATAGATA | 0.9 |
| HYBMTH | 109-110 | GTCFGCGGGAGCCGAFTTCATC | 1.18 |
| FVG11 | 60, 24 | CTGTAFTCCTCGCCFGTCC | 1.2 |
| HYBCH10 | 108, 103 | CAAGCCFGCAAATGTAFACCAAG | 1.24 |
| HYBCH | 61, 35 | CAAGCCFGCAAAFGTATACCAAG | 1.50 |
| HYBCH9 | 107, 103 | CAAGCCTGCAAAFGTAFACCAAG | 1.59 |
| HYBFII | 115-116 | GCATFGAGGCTCGCFGAGAGTC | 1.59 |
| HYBA1928C | 112-113 | GACCAGFGAAGCAAGFGTCTTTG | 1.62 |
| HYBMRSA | 99-100 | CGTAGFTACTGCGTFGTAAGACGTC | 2.0 |
| FVG111 | 127, 24 | CTGTAFTCCFCGCCFGTCC | 2.2 |
| HYBAdD | 68-69 | GACGTGGFCAGAGFGCACCAGCCT | 2.4 |
| HYBCH5 | 102-103 | CAAGCCFGCAAAFGTAFACCAAG | 2.6 |
| HYBCH6 | 103-104 | GTAAFCAAGCCFGCAAAFGTATACCAAG | 2.6 |
| HYBAdC | 70-71 | GACGTGGFCCGTGFGCACCAGCCT | 3.4 |
| HYBCH11 | 126,103 | GTAAFCAAGCCFGCAAAFGTAFACCAAG | 3.5 |

Fluorophores attached to internal residues of The oligonucleotides of the invention are quenched in the single-stranded state and hybridisation relieves a proportion of this quenching. Quenching in the single-stranded probe may arise as the DNA bases can stack on the fluorescent group when they are not forming base pairs. In the single stranded form the fluorophore will be sandwiched between two DNA bases forming a fairly stable hydrophobic structure. This will break down on duplex formation as the bases have to participate in base pairing. The phenomenon may not merely be "guanine quenching", although guanines would possibly have a greater influence than other bases.

The situation with terminal labels is different, as base stacking can only occur on one side of the fluorophore. In the single strand (and in the duplex) the fluorophore will not be sandwiched between DNA bases, but just stacked on a base. Quenching upon hybridisation may occur if the fluorophore is brought into close proximity to guanine bases in the target strand. Conversely, fluorescence enhancement may occur on hybridisation if fluorophores are attached to terminal G residues of the probe. The internal labels of the oligonucleotide probes are affected considerably less by the probe and target sequences and always exhibit fluorescence increases upon hybridisation regardless of the position of guanines in the duplex. The terminal labelled probes are influenced by the oligonucleotides in the target sequence and can exhibit increased or decreased levels of fluorescence upon target hybridisation. The dual-labelled oligonucleotides of the invention exhibit increased levels of fluorescence on hybridisation due to independence of target sequence and not an interaction between fluorophores.

Example 9

Signal Strength and Fluorophore Spacing in Multi-Labelled Probes

Incorporating additional fluorophores into oligonucleotide probe sequences may be expected to increase probe emission in both hybridised (signal) and single-stranded (noise) states, thereby maintaining the signal-to-noise ratio. Alternatively, since FAM dyes can actually quench each other when in proximity, labelling probes with multiple fluorophores may cause the signal-to-noise ratio to deteriorate. However, probe signal-to-noise ratios and melt peak heights have been improved considerably through the inclusion of two or more FAM dyes within the oligonucleotide probe sequences. All probes described above utilise either C6 FAM dU or Glen fluorescein dT to replace thymine nucleotides and fluorophores in these probes are separated by at least three nucleotides. The inclusion of additional fluorophores in The oligonucleotides of the invention (e.g. 3 or 4 FAM labels) may further enhance signal-to-noise ratios and melt peak heights. However, fluorophore-labelled bases should be separated by a minimum number of nucleotides to avoid direct quenching between fluorophores by non-radiative energy transfer. This non-FRET quenching can occur through short-range 'contacts' between dyes and does not require overlap of excitation and emission spectra. FRET quenching may also occur between FAM labels due to the overlap between excitation and emission spectra. The preferred spacing when designing the oligonucleotide probes of the invention is 3-6. However, all probes with fluorophores separated by at least 2 unlabelled nucleotides exhibit considerable increases in fluorescence on target hybridisation. Spacings greater than 11 nucleotides have not been tested but may yield efficient signals depending on their relative angular disposition in the duplex (see table 7).

150 nM of HYBCHRC (SEQ ID NO:35) reverse homologue oligonucleotide was hybridised to 150 nM of single-labelled (HYBCH2), dual-labelled (HYBCH), triple-labelled (HYBCH3) and quadruple (HYBCH4) Chlamydia probes in TaKaRa PCR buffer and a total of 3 mM $MgCl_2$.

```
HYBCH2    5'CAAGCCTGCAAAFGTATACCAAG      (SEQ ID NO: 32)

HYBCH     5'CAAGCCFGCAAAFGTATACCAAG      (SEQ ID NO: 61)

HYBCH3    5'CAAGCCFGCAAAFGFATACCAAG      (SEQ ID NO: 96)

HYBCH4    5'CAAGCCFGCAAAFGFAFACCAAG      (SEQ ID NO: 97)
```

Melt peaks were generated using a LightCycler protocol comprising denaturation 1.0 (95° C. 5 s), cooling (35° C. 30 s) and a slow heat to 95° C. at 0.2° C./s. Compared with the single-labelled probe, the dual-labelled HYBCH oligonucleotide probe displayed an elevated signal-to-noise ratio and melt peak height along with a reduced Tm as described above. The fluorophore-labelled bases of HYBCH are separated by 5 nucleotides. The triple-labelled HYBCH3 probe is quenched slightly upon target hybridisation and exhibits a small negative/inverted peak in—dF/dT traces (FIG. 11). The Tm of HYBCH3 is reduced compared with the single-labelled probe, but is higher than that of the dual-labelled oligonucleotide probe. The quadruple-labelled HYBCH4 probe exhibits a small positive peak in—dF/dT traces and a Tm similar to that of HYBCH. Both HYBCH3 and HYBCH4 probes contain fluorophore-labelled bases that are separated by only a single nucleotide and display considerably reduced levels of fluorescence in both hybridised and dissociated states (FIG. 11). Fluorescence data indicates that the proximal FAM dyes are quenching each other in the single-stranded state. The HYBCH3 probes is quenched to a greater extent upon hybridisation to complementary target sequences, suggesting that when the fluorophores project into solution they may be brought into even closer contact than when in the single-stranded conformation.

Additional triple-labelled Chlamydia probes were designed with a greater level of separation between fluorophore-labelled bases. 150 nM of HYBCH6RC (SEQ ID NO:103) reverse homologue oligonucleotide was hybridised to 150 nM of single-labelled (HYBCH2), dual-labelled (HYBCH) and triple-labelled (HYBCH5 & HYBCH6) probes in TaKaRa PCR buffer and a total of 3 mM $MgCl_2$. Melt peaks were generated using a LightCycler protocol comprising denaturation (95° C. 5 s), cooling (35° C. 30 s) and a slow heat to 95° C. at 0.2° C./s.

```
HYBCH2    5'CAAGCCTGCAAAFGTATACCAAG      (SEQ ID NO: 32)

HYBCH     5'CAAGCCFGCAAAFGTATACCAAG      (SEQ ID NO: 61)

HYBCH5    5'CAAGCCFGCAAAFGTAFACCAAG      (SEQ ID NO: 102)

HYBCH6    5'GTAAFCAAGCCFGCAAAFGTATA      (SEQ ID NO: 104)
          CCAAG
```

The triple-labelled HYBCH5 probe exhibits a Tm very similar to that of the HYBCH dual-labelled probe (table 1). Adding more than two fluorescent labels may not provide further stabilisation of the single-stranded structure. The triple-labelled HYBCH6 probe is 5 nucleotides longer than the previously mentioned *Chlamydia* probes and displays a Tm similar to the single-labelled HYCH2 probe.

The triple-labelled probes both yield melt peaks that are 6.5 and 3.25 times the height of the single-labelled HYBCH2 and dual-labelled HYBCH probes respectively (FIGS. 4 & 11 C).

To investigate the contributions that each fluorophore has on the total signal strength, the triple-labelled HYBCH5 probe was compared with the three possible single-labelled *Chlamydia* probes and three dual-labelled oligonucleotide probes. Each modified position within the triple-labelled oligonucleotide probes was represented in the single and dual-labelled probes. These probes were also compared with a quadruple-labelled oligonucleotide probes (SEQ ID NO:126). As described previously, 150 nM of HYBCH6RC (SEQ ID NO:103) reverse homologue oligonucleotide was hybridised to 150 nM of probe in TaKaRa PCR buffer and a total of 3 mM $MgCl_2$.

```
HYBCH2    5'CAAGCCTGCAAAFGTATACCAAG  (SEQ ID NO: 32)
HYBCH7    5'CAAGCCFGCAAATGTATACCAAG (SEQ ID NO: 105)
HYBCH8    5'CAAGCCTGCAAATGTAFACCAAG (SEQ ID NO: 106)
HYBCH     5'CAAGCCFGCAAAFGTATACCAAG  (SEQ ID NO: 61)
HYBCH9    5'CAAGCCTGCAAAFGTAFACCAAG (SEQ ID NO: 107)
HYBCH10   5'CAAGCCFGCAAATGTAFACCAAG (SEQ ID NO: 108)
HYBCH5    5'CAAGCCFGCAAAFGTAFACCAAG (SEQ ID NO: 102)
HYBCH11   5'GTAAFCAAGCCFGCAAAFGTAFA (SEQ ID NO: 126)
          CCAAG
```

The heights of melt peaks generated in two LightCycler instruments (LC1 and LC2) exhibited greater levels of variation than the calculated signal-to-noise ratios (table 4). However, with both LightCycler instruments, the peak heights of the triple-labelled probe were approximately twice the height of the most efficient dual-labelled probe and more than four times greater than the most efficient single-labelled oligonucleotide probe (table 4). The height of the triple-labelled melt peaks is greater than the sum of the three single-labelled oligonucleotide probes and is also greater than the sum of any dual-labelled probe plus any equivalent single-labelled oligonucleotide probe. The quadruple-labelled oligonucleotide probe also yielded high quality melt data, exhibiting peak heights that were approximately 25% larger than the triple-labelled probes (table 4).

TABLE 4

Peak heights and signal-to noise ratios generated with single, double and triple-labelled Chlamydia probes using two LightCycler instruments (LC1 & LC2). Each melt peak and curve was analysed in duplicate and the mean value is presented.

| Probe | Fluoro-phores | Peak height (LC1) | Peak height (LC2) | Signal-to-noise (LC1) | Signal-to-noise (LC2) |
|---|---|---|---|---|---|
| HYBCH2  | 1 | 0.71 | 0.43 | 1.43 | 1.47 |
| HYBCH7  | 1 | 0.97 | 0.52 | 1.42 | 1.54 |
| HYBCH8  | 1 | 0.62 | 0.33 | 1.36 | 1.33 |
| HYBCH   | 2 | 1.41 | 0.74 | 1.87 | 1.87 |
| HYBCH9  | 2 | 2.1  | 1.59 | 1.58 | 1.92 |
| HYBCH10 | 2 | 2.23 | 1.24 | 1.60 | 1.74 |
| HYBCH5  | 3 | 4.28 | 2.80 | 2.33 | 2.42 |
| HYBCH11 | 4 | —    | 3.50 | —    | 2.90 |

The single, dual and triple-labelled *Chlamydia* probes were also investigated at 35° C. in the presence and absence of target to compare the levels of fluorescence emission in hybridised and single-stranded states. 150 nM of HYBCH6RC (SEQ ID NO:103) reverse homologue oligonucleotide was hybridised to 150 nM of probe in TaKaRa PCR buffer and a total of 3 mM $MgCl_2$. Samples were denatured in LightCycler capillaries (95° C. 5 s) prior to cooling to 35° C. with continuous fluorescence acquisition. Probes were analysed in duplicate in the presence and absence of target and the mean emission values for hybridised and single-stranded states are detailed in table 5. In the absence of target, the triple-labelled oligonucleotide probe emits less fluorescence than any of the single and dual-labelled probes. Whereas, in the presence of target, the level of fluorescence from the triple-labelled probe was very similar to that emitted from the dual-labelled HYBCH10 probe. The triple-labelled probe exhibits the biggest difference between duplex and single-stranded states and thus yields the largest melt peaks. An interaction between fluorophores, such as quenching in the single-stranded probe structure, may be responsible for the elevated peak heights and signal-to-noise ratios exhibited by dual and triple-labelled oligonucleotide probes. In the single-strand (random coil) the fluorophores can contact each other and stack giving rise to collisional quenching whereas this is not possible in the duplex as the fluorophores are kept apart by the rigid B-DNA structure when separated by at least two nucleotides. If they are closer together the flexible linker on the 5-position of the thymine base can allow the fluorophores to approach each other.

TABLE 5

Levels of emission (LightCycler arbitrary fluorescence units) at 35° C. in the presence and absence of a complementary oligonucleotide. The difference between hybridised and single-stranded states in also included.

| Probe | Fluoro-phores | Plus target | Minus target | Difference |
|---|---|---|---|---|
| HYBCH2  | 1 | 9.0  | 7.2  | 1.8  |
| HYBCH7  | 1 | 8.4  | 7.0  | 1.4  |
| HYBCH8  | 1 | 9.8  | 7.8  | 2.0  |
| HYBCH   | 2 | 10.2 | 5.1  | 5.1  |
| HYBCH9  | 2 | 14.3 | 7.4  | 6.9  |
| HYBCH10 | 2 | 16.5 | 11.6 | 4.9  |
| HYBCH5  | 3 | 16.2 | 5.0  | 11.2 |

Example 10

Further Comparison of Single, Dual and Triple-Labelled Oligonucleotides

Three single-labelled Factor V oligonucleotide probe were compared with dual and triple-labelled probes of identical sequence. All fluorophores present in the dual and triple-labelled oligonucleotide probes were represented in the single-labelled probes. 150 nM of FVG (SEQ ID NO:24) reverse homologue oligonucleotide was hybridised to 150 nM of oligonucleotide probe in TaKaRa PCR buffer and a total of 3 mM $MgCl_2$. Melt peaks were generated using a LightCycler protocol comprising denaturation (95° C. 5 s), cooling (35° C. 30 s) and a slow heat to 95° C. at 0.2° C./s. The peak heights and signal-to-noise ratios of single, dual and triple-labelled probes are presented in table 6.

```
FVG1      5'CTGTAFTCCTCGCCTGTCC    (SEQ ID NO: 21)
FVG1ALT   5'CTGTATTCCTCGCCFGTCC    (SEQ ID NO: 101)
FVG1ALT2  5'CTGTATTCCFCGCCTGTCC    (SEQ ID NO: 128)
FVG11     5'CTGTAFTCCTCGCCFGTCC    (SEQ ID NO: 60)
FVG111    5'CTGTAFTCCFCGCCFGTCC    (SEQ ID NO: 127)
```

Figure 12:
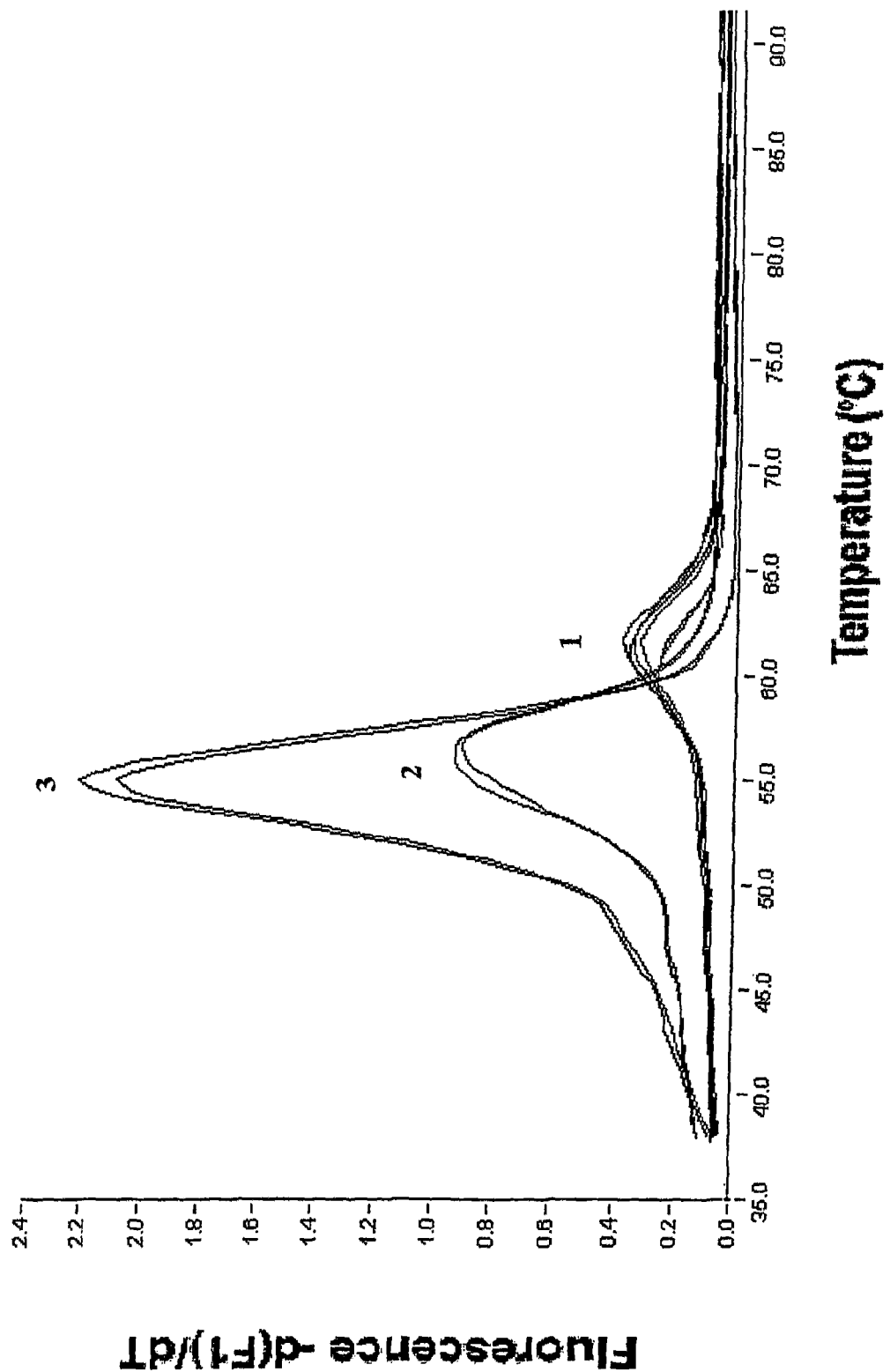
FIG. 12 shows melt peaks derived from single-labelled (1), dual-labelled (2) and triple-labelled (3) factor V oligonucleotide probes.

The dual-labelled FVG11 probe yields melt peaks that are approximately 3-4 times larger than the single-labelled oligonucleotide probes that possess fluorophores at identical positions within the sequence. As such, dual-labelled melt peaks are greater than the sum of the single-labelled peaks. Furthermore, the triple-labelled oligonucleotide probe generates melt peaks that are at least 7 times larger than the single-labelled oligonucleotide probes and 2.6 times larger than the dual-labelled probe (FIG. 12). Melt peaks from the triple-labelled probes are considerably larger than the sum of the peaks derived from single-labelled oligonucleotides. As with the *Chlamydia* oligonucleotides, the addition of multiple fluorophores to probes causes the generation of melt peaks whose heights are greater than would be expected from the single-labelled oligonucleotide probes. The data derived from *Chlamydia* and Factor V probes demonstrates that incorporating two or three fluorophore-labelled bases does not necessarily double or triple the height of oligonucleotide probe melt peaks.

TABLE 6

Peak heights and signal-to noise ratios generated with single, double and triple-labelled Factor V probes in a single LightCycler experiment (LC2). Each melt peak and curve was analysed in duplicate and the mean value is presented.

| Probe | Fluorophores | Tm | Peak height | Signal-to-noise |
|---|---|---|---|---|
| FVG1 | 1 | 60.0 | 0.21 | 1.33 |
| FVG1ALT | 1 | 61.2 | 0.28 | 1.46 |
| FVG1ALT2 | 1 | 61.2 | 0.30 | 1.47 |
| FVG11 | 2 | 56.1 | 0.84 | 1.79 |
| FVG111 | 3 | 55.9 | 2.2 | 3.14 |

Example 11

Minimum Spacing Between Fluorophores

A series of oligonucleotide probes was synthesised to determine the minimum spacing required between fluorophore-labelled bases in dual-labelled oligonucleotide probes. The probes possessed between 0 and 9 nucleotides between the fluorophore-labelled bases. 150 nM of MODRC (5'CCCCCCTTTTTTTTTTTTCCCCCC (SEQ ID NO:139)) reverse homologue oligonucleotide was hybridised to 150 nM of the oligonucleotide probe in TaKaRa PCR buffer and a total of 3 mM MgCl$_2$. Melt peaks were generated using a LightCycler protocol comprising denaturation (95° C. 5 s), cooling (35° C. 30 s) and a slow heat to 95° C. at 0.2° C./s. The signal-to-noise ratios and heights of melt peaks are presented in table 7. The probes possessing 0 and −1 nucleotides between labelled bases demonstrated considerably reduced levels of fluorescence due to contact quenching caused by the close proximity of fluorophores. Both of these probes exhibited negative (inverted) melt peaks, where the level of fluorescence decreased when hybridised to target sequences relative to the single-stranded state. All probes possessing between 2 and 9 nucleotides separating the fluorophore-labelled bases exhibited positive melt peaks and enhancement of fluorescence upon target hybridisation. The probes possessing fluorophores separated by 7 and 8 nucleotides exhibited slightly reduced levels of fluorescence and smaller melt peaks compared with the 2-6 and 9 spaced probes. Probes that possess multiple fluorophores on the same surface of duplex DNA may encounter a degree of contact quenching, thereby displaying reduced peak heights and signal-to-noise ratios. These angular disposition affects may be sequence specific since 8 nucleotide spacings have been employed in FVG11 (SEQ ID NO:60), HYBMRSA (SEQ ID NO:99) and HYBA1928C (SEQ ID NO:112) probes, generating large melt peaks and signal-to-noise ratios. At least two nucleotides separating fluorophore-labelled bases are required for the oligonucleotide probes to yield higher levels of fluorescence emission upon target hybridisation relative to the free probe.

TABLE 7

Melt peaks generated in a single LightCycler experiment (LC2) to determine the minimum spacing required between fluorophore-labelled bases. Each melt peak was analysed in duplicate and the mean value is presented.

| Probe | Space | Sequence | SEQ ID | Peak height | Signal-to-noise |
|---|---|---|---|---|---|
| MOD0 | 0 | GGGGGGTTTTFFTTTTTTGGGGGG | 129 | −0.06 | 0.71 |
| MOD1 | 1 | GGGGGGTTTTTFTFTTTTTTGGGGGG | 130 | −0.07 | 0.84 |
| MOD2 | 2 | GGGGGGTTTTFTTFTTTTTGGGGGG | 131 | 0.26 | 1.29 |
| MOD3 | 3 | GGGGGGTTTTFTTTFTTTTGGGGGG | 132 | 0.24 | 1.30 |
| MOD4 | 4 | GGGGGGTTTFTTTTFTTTTGGGGGG | 133 | 0.24 | 1.30 |
| MOD5 | 5 | GGGGGGTTTFTTTTTFTTTGGGGGG | 134 | 0.17 | 1.25 |
| MOD6 | 6 | GGGGGGTTFTTTTTTFTTTGGGGGG | 135 | 0.20 | 1.23 |
| MOD7 | 7 | GGGGGGTTFTTTTTTTFTTGGGGGG | 136 | 0.09 | 1.15 |
| MOD8 | 8 | GGGGGGTFTTTTTTTTFTTGGGGGG | 137 | 0.06 | 1.11 |
| MOD9 | 9 | GGGGGGTFTTTTTTTTTFTGGGGGG | 138 | 0.15 | 1.31 |

All dual, triple and quadruple-labelled oligonucleotide probes designed to date, which possess between two and eleven nucleotides separating fluorophore-labelled bases, demonstrate considerable enhancement of fluorescence upon hybridisation to complementary target sequences. Only those probes with zero or one nucleotide separating fluorophore-labelled bases have been found to exhibit small levels of fluorescence quenching upon target hybridisation. A maximum separation of fluorophore-labelled nucleotides has not yet been identified.

Example 12

Attachment of Fluorophores to dA and dC

FAM dA and FAM dC oligonucleotide probes were synthesised using amino-dA and amino-dC monomers (Glen Research, Sterling, Va.) and post-synthetic labelling with FAM. Single and dual-labelled probes containing FAM dC and FAM dA were synthesised and compared with single and dual-labelled C6 FAM dU oligonucleotide probes (table 8). 150 nM of the appropriate reverse homologue oligonucleotide (FVG or GLENARC) was hybridised to 150 nM the oligonucleotide probe in TaKaRa PCR buffer and a total of 3 mM MgCl$_2$. Melt peaks were generated using a LightCycler protocol comprising denaturation (95° C. 5 s), cooling (35° C. 30 s) and a slow heat to 95° C. at 0.2° C./s.

```
FVG       5'GGACAGGCGAGGAATACAG      (SEQ ID NO: 24)
GLENARC   5'CTGTATACCTTGCCTGTCC      (SEQ ID NO: 91)
```

Figure 13:
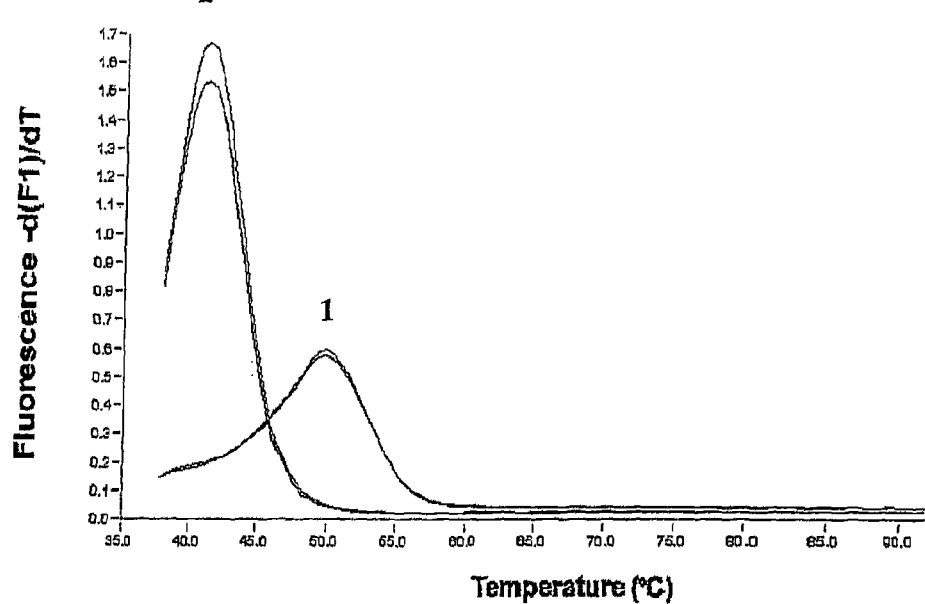
FIG. 13 shows single-labelled (1) and dual-labelled (2) The oligonucleotides of the invention containing A) FAM dA and B) FAM dC.
Figure 13:
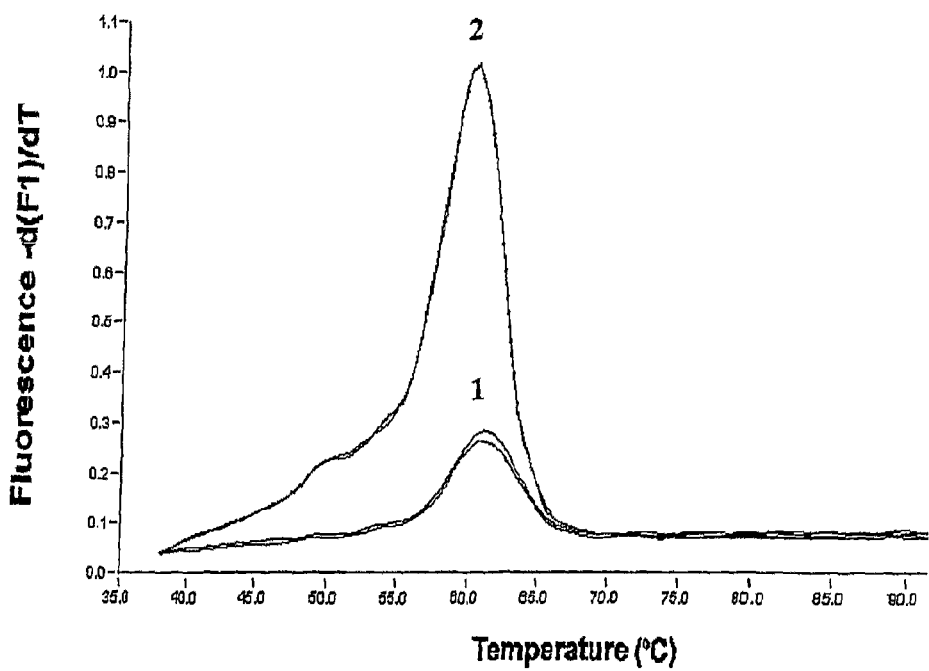

The FAM dC and FAM dA probes all exhibited enhanced levels of fluorescence upon target hybridisation relative to the single-stranded state (FIG. 13). Enhancement of fluorescence emission upon FAM dC hybridisation supports the model that the oligonucleotide probe fluorophores do not interact with the DNA of the target strand since interaction with Gs in the target would be expected to cause fluorescence quenching. As with C6 FAM dU and fluorescein dT, the dual-labelled FAM dC and FAM dA probes both yield melt peaks that are greater than twice the height of the equivalent single-labelled oligonucleotide probe.

Dual-labelled C6 FAM dU and fluorescein dT probes exhibit Tms that are approximately 4-5° C. lower than single-labelled probes of identical sequence. The probes labelled with FAM dC and FAM dA exhibited 1° C. and 8.3° C. Tm differences respectively (table 8).

For A, T, C and U, it does not matter whether fluorophores are attached to nucleotides pre, during or post-synthesis. Attachment to these nucleotides is possible whilst maintaining the 'natural' base. Attachment of the fluorophore directly to G produces a base analogue.

Example 13

Asymmetric PCR to Enhance Melt Peak Height

Following the PCR stage of assays using the oligonucleotides of the invention, probes compete with amplified products to hybridise to the target sequence. This competition reduces the potential for probe/target interactions and limits the height of melt peaks. If target hybridisation is shifted in favour of the probe, the height of melt peaks can be increased. This may be achieved by either increasing the concentration of the probe or decreasing the abundance of the PCR competitor strand.

The optimal concentration of the oligonucleotide probes has been found to be 150 nM. Increasing the probe concentration above 200 nM has not been found to improve signal-to-noise ratios. In fact, increased probe concentration has an adverse affect on *Chlamydia* melt traces, generating a second peak at approximately 80° C. that increases in height along with probe concentration. Peak qualities have also been found to be reduced at elevated probe concentrations due to additional background fluorescence arising from single-stranded probes that are unable to hybridise to target sequences.

The abundance of the competing DNA strand may be reduced, relative to the target sequence, by using an asymmetric amplification method. The concentration of *Chlamydia* forward and reverse primers was optimised to maximise the height of melt peaks. *Chlamydia* cryptic plasmid targets were amplified using primers CHF3-1 (SEQ ID NO:33) and CHR4-1 (SEQ ID NO:34). Assays employed 3-stage Light-Cycler protocols consisting of an initial denaturation (95° C. 1 min) followed by 50 cycles of PCR comprising denaturation (95° C. 5 s), primer annealing (55° C. 10 s) and extension of products (72° C. 10 s). Amplified target was detected and characterised through the inclusion of HYBCH probe (SEQ ID NO:61) and melt curve analysis comprising denaturation (95° C. 0 s), cooling (35° C. 30 s) and a slow heat towards 95° C. using a 0.2° C./s transition rate. In the presence of *Chlamydia* DNA, the HYBCH probe generates clear melt peaks with Tms of approximately 56° C. (FIG. 14). It was found that a ten-fold dilution of the forward primer (0.05 µM) relative to the reverse primer (0.5 µM) increased the height of *Chlamydia* peaks by three to five-fold compared with standard

TABLE 8

Peak heights and signal-to-noise ratios derived from oligonucleotide probes containing C6 FAM dU, FAM dC and FAM dA labels.

| Probe | SEQ ID NO: | Sequence | Labelled base | Tm | Peak height | Signal-to-noise |
|---|---|---|---|---|---|---|
| FVG1 | 21 | CTGTAFTCCTCGCCTGTCC | FAM dU | 59.9 | 0.22 | 1.35 |
| FVG11 | 60 | CTGTAFTCCTCGCCFGTCC | FAM dU | 56.0 | 0.81 | 1.81 |
| GLENC1 | 125 | CTGTATTFCTCGCCTGTCC | FAM dC | 60.9 | 0.28 | 1.37 |
| GLENC2 | 72 | CTGTATTFCTCGCFTGTCC | FAM dC | 59.9 | 1.03 | 1.81 |
| GLENA1 | 73 | GGACAGGCAAGGFATACAG | FAM dA | 49.8 | 0.59 | 2.4 |
| GLENA2 | 90 | GGACFGGCAAGGFATACAG | FAM Da | 41.5 | 1.52 | 4.1 |
| ATD0638 | 142 | GGACAFGCAAGGTATACAG | FAM dG | 53.0 | 0.63 | 2.0 |
| ATD0639 | 143 | GGACAFGCAAGGFTATACAG | FAM dG | 53.0 | 0.15 | 1.5 | equimolar assays (FIG. 14). This increased peak height was observed with purified genomic DNA and processed clinical samples. The combination of asymmetric PCR with a triple-labelled labelled probe (HYBCH6) generated melt peaks that were approximately 20 times the size of those generated in symmetric assays employing the single-labelled oligonucleotide probe.

Example 14

Asymmetric PCR, Probe Concentration and Peak Heights

Asymmetric PCR has yielded increased peak heights, relative to symmetric amplification, with *Chlamydia, Gonorrhoea,* Factor 11, A1928C, and C677T assays. However, asymmetric amplification failed to enhance peak heights in the NAT2*5C test. Since asymmetric PCR generates single-stranded targets, probes do not have to compete for hybridisation with complementary PCR strands and melt peaks have the potential to be of similar magnitude to those derived with oligonucleotides. If symmetric amplification yields melt peaks that are already of similar magnitude to oligonucleotide peaks (e.g. NAT2*5C assay), no benefit may be derived from asymmetric amplification. It appears that only those probes that display reduced peak heights, compared with oligonucleotides, exhibit enhanced peak heights when assays are converted to asymmetric tests. Asymmetric PCR may be beneficial if assays utilise long target amplicons or if primer-dimers are generated.

The Factor V probes (FVG1 and FVG11) are a more complicated situation. Melt peaks generated in symmetric assays are of reasonable height, allowing reliable identification of samples, but are reduced compared with peaks derived from oligonucleotide targets. Fifty cycles of asymmetric amplification, performed with a heterozygous sample, has been found not to affect the height of either matched or mismatched peaks relative to symmetric assays. However, 60 and 70 cycles of asymmetric amplification were found to increase the height of the matched melt peak whilst reducing/not affecting the height of the mismatched peak (FIG. 14). After 70 cycles, the probe becomes saturated with target such that preferential hybridisation to the fully complementary allele results in an imbalance of peak heights. The increased stability of fully complementary probe/target duplexes is responsible for this preferential hybridisation and increased peak height relative to the mismatched duplex.

The FVG11 probe (SEQ ID NO:60) was hybridised to fully complementary (FVG (SEQ ID NO:24)) and mismatched (FVA (SEQ ID NO:25)) oligonucleotides to investigate the affect of target concentration on the heights of melt peaks. Melt analysis was performed in a LightCycler instrument employing a thermal protocol comprising denaturation (95° C. 0 s), cooling (35° C. 30 s) and a slow heat to 95° C. using a 0.2° C./s transition rate. Matched and mismatched targets were employed at equimolar concentrations. 150 nM of probe hybridised to 150 nM of target yielded matched and mismatched melt peaks of identical height (FIG. 15). 300 nM of probe hybridised to 300 nM of target also yielded matched and mismatched peaks of comparable height. However, 150 nM of probe hybridised to 1 µM of target yielded only the matched melt peak (FIG. 15). The fully complementary target sequesters the probe and competitive hybridisation prevents efficient hybridisation to the mismatched target. The factor V SNP affects the stability of probe/target duplexes considerably, such that at high target concentrations the probe binds preferentially to the fully complementary sequence. This observation also explains the imbalance of peak heights between fully complementary and double mismatched targets, such as in the sickle cell and NAT1*10 assays.

To ascertain whether higher concentrations of probe could re-establish the balance of matched and mismatched peak heights at elevated target concentrations, symmetric and asymmetric assays were performed using 150 nM, 300 nM and 500 nM of FVG11 probe and a heterozygous Factor V genomic DNA sample. Fifty, sixty and seventy cycles of 2-stage amplification were performed. After 50 cycles, the matched and mismatched peak heights were balanced and there was not a considerable difference between symmetric and asymmetric reactions (FIG. 16). The 150 nM probe reactions yielded the highest quality data. The heights of matched and mismatched melt peaks generated, with 150 nM of probe, after 60 and 70 asymmetric cycles were unequal as demonstrated in FIG. 14. The height of the mismatched melt peak was considerably improved at the higher probe concentrations. After 60 asymmetric cycles, 150 nM FVG11 yielded matched and mismatched melt peaks with heights of 0.83 and 0.35 respectively (2.3 times difference). Whereas, 500 nM of probe yielded matched and mismatched melt peaks with heights of 0.63 and 0.50 respectively (1.13 times difference). The combined height of heterozygous peaks in 150 nM and 500 nM probe reactions was 1.19 and 1.13 respectively, similar to that observed with homozygous oligonucleotide target (FIG. 3). The increased concentration of probe balanced the height of matched and mismatched melt peaks generated with asymmetrically amplified products. The oligonucleotide and PCR data does confirm the competitive hybridisation of probes to matched and mismatched target molecules. At high target concentrations, this competitive hybridisation and the reduced stability of mismatched duplexes results in the reduction or loss of peaks in a multi-target melt profile. Probe concentrations higher than 150 nM may be required in certain asymmetric assays.

Example 15

Multiplex Analysis by Melting Temperature

Four oligonucleotide probes were simultaneously hybridised to their complementary oligonucleotide targets in a single LightCycler capillary to demonstrate the multiplex potential of melt peak analysis. The probes and targets were employed at various concentrations to equalise the heights of peaks derived from single-labelled and dual-labelled probes. The polyT, HYBINF, HYBCH2 and HYBAdC probes and target oligonucleotides were employed at 1.2 µM, 233 nM, 183 nM and 27 nM respectively. Melt peaks were generated in TaKaRa PCR buffer, and a total of 3 mM $MgCl_2$ using a LightCycler protocol comprising denaturation (95° C. 5 s), cooling (35° C. 30 s) and a heat towards 95° C. at 0.4° C./s. The polyT, HYBINF, HYBCH2 and HYBAdC probes generated clear melt peaks with Tms of approximately 49° C., 54° C., 62° C. and 68° C. respectively (FIG. 17). At least four target sequences may be detected and identified on the basis of Tm using the oligonucleotide probes permitting simultaneous analysis of two biallelic SNPs. Multiplex potential may be enhanced further using spectrally distinct fluorescent dyes.

Example 16

Positive Amplification Control

Oligonucleotides of the invention may be employed to determine the presence or absence of infectious pathogens in clinical samples. The generation of specific melt peaks indicates the presence of particular infectious agents within the sample. However, the total absence of melt peaks does not reliably signify the lack of pathogen. Clinical samples, such as urine, may contain high levels of PCR inhibitors that may prevent pathogen detection in positive samples. An amplification control is required to distinguish reactions that are negative due to pathogen absence from those that failed to generate melt peaks due to PCR inhibition.

The *Chlamydia* amplification control (mimic) was constructed using a 142 base oligonucleotide (SEQ ID NO:98). The long oligonucleotide was employed as PCR template for cloning purposes and contained a C to T base substitution within the probing region to enable differentiation of mimic from Chlamydial target on the basis of Tm. Amplification from the long oligonucleotide was performed using CHF3-1 (SEQ ID NO:33) and CHR4-1 (SEQ ID NO:34) primers. The amplified product was ligated into the pDrive vector using a PCR cloning$^{plus}$ Kit (Qiagen Ltd, Crawley, UK) and transformed into Qiagen EZ competent cells. Colonies containing the mimic sequence were identified directly using the *Chlamydia* assay using the oligonucleotide probes of the invention. Plasmids were purified from transformant cultures using a QIAprep Spin Miniprep kit (Qiagen Ltd, Crawley, UK) using the manufacturer's recommended procedures. Hybridisation of *Chlamydia* oligonucleotides of the invention to the mimic target sequence results in a C:A mismatch that reduces probe Tms by approximately 8° C. (FIG. 18).

Example 17

DNA Quantification Using the Oligonucleotide Probes of the Invention

Factor V targets were amplified from a series of DNA standards using primers FVF1.3 (SEQ ID NO:22) and FVR3.5 (SEQ ID NO:23). The DNA standards contained 100 ng/μl, 10 ng/μl, 1 ng/μl, 100 pg/μl and 10 pg/μl of human genomic DNA. Assays employed 3-stage LightCycler protocols consisting of an initial denaturation (95° C. 1 min) followed by 50 cycles of PCR comprising denaturation (95° C. 0 s) and annealing (50° C. 10 s) and extension (72° C. 10 s) phases. Amplified target was detected and characterised through the inclusion of FVG1 (SEQ ID NO:21) or FVG11 (SEQ ID NO:60) and fluorescence acquisition during the annealing phase of PCR. Measuring the cycle number at which fluorescence emission increases above a threshold level ($C_T$) enables quantification of DNA targets (FIG. 19). The $C_T$ values derived during real-time PCR assays are directly proportional to the starting copy number of the target sequence and can be used to construct standard curves, from which 'unknown' samples may be quantified. Saliva samples have been typically found to contain approximately 1 ng/μl of human genomic DNA.

Example 18

Analysis Using Fluorophores Other than Fluorescein

Four Factor V oligonucleotide probes were synthesised each labelled with fluorophores at two internal positions. These probes were:

FVG11TAM 5'CTGTAXTCCTCGCCXGTCC (SEQ ID NO:140) where X is a dT residue labelled with TAMRA.

FVG11ROX 5'CTGTAXTCCTCGCCXGTCC (SEQ ID NO:141) where X is a dT residue labelled with ROX.

FVG11Cy5 5'CTGTAXTCCTCGCCXGTCC (SEQ ID NO:142) where X is a dT residue labelled with Cy5.

FVG11Mix 5'CTGTAFTCCTCGCCXGTCC (SEQ ID NO:143) where F is a dT residue labelled with FAM and X is a dT residue labelled with ROX.

The probes were hybridised to their complementary oligonucleotide targets (SEQ ID NO:24) in 96 well optical plates in TaKaRa PCR buffer and total of 3 mM $MgCl_2$ and melt curves generated using an ABI 7700 thermocycler. The melt protocol comprised denaturation (95° C. 30 s), cooling (35° C. 30 s) and a melting profile comprising a stepwise progression from 35° C. to 95° C. in 1° C. increments with a 15 s hold at each temperature. The probes and complements were used at concentrations of 150 nM. Raw data was exported from the ABI 7700 thermocycler and processed using the Excel spreadsheet programme from Microsoft. FIGS. 20A, 20B, 20C and 20D show the melt curves of these probes from their complements and in all cases an inflection in the curve is seen and demonstrates a decrease in fluorescent as a direct result of the dissociation of the probe from its target in comparison to the linear decrease of fluorescence as a function of temperature despite the optics system being sub-optimal for the detection of Cy5. This data confirms previous data and conclusions that this phenomenon is a general feature of fluorophores and is not restricted to fluorescein and other fluorescein based derivatives.

CONCLUSION

Oligonucleotide probes possessing single and multiple fluorophore-labelled internal bases all exhibit increased levels of fluorescence emission when hybridised compared with the single-stranded state. Since probe fluorescence always increases upon hybridisation irrespective of oligonucleotide probe and target sequences, it is envisaged that the fluorophores interact with probe DNA when single-stranded, resulting in quenching, but do not interact with probe or target sequences when in the duplex state such that fluorophores are dequenched and fluorescence increases. The increased levels of fluorescence emitted by hybridised probes is thought to arise from the fluorophores projecting into solution away from the quenching influence of DNA.

An unexpected finding from comparing single-labelled oligonucleotide probes with dual and triple-labelled probes of identical sequence was that fluorescence was not simply doubled or tripled with the inclusion of additional fluorophores. Double and triple-labelled probes exhibited melt peaks that were larger than expected from each of the single-labelled oligonucleotide probes suggesting an interaction between fluorophores. Fluorophores in oligonucleotide probes are preferably separated by at least two nucleotides to prevent contact quenching and ensure efficient signal generation upon target detection.

TABLE 9

General fluorescent dyes for oligonucleotide labelling

| Dye | λ-excit | λ-emiss | colour |
|---|---|---|---|
| Fluorescein | 494 nm | 525 nm | Green |
| Tetrachloro Fluorescein TET | 521 nm | 536 nm | Orange |
| JOE | 525 nm | 555 nm | Green |
| Yakima Yellow | 530 nm | 549 nm | Yellow |
| Hexachloro Fluorescein HEX | 535 nm | 556 nm | Pink |
| Cy3 (also Quasar 570) | 546 nm | 563 nm | Red |
| 5-TAMRA | 541 nm | 568 nm | Rose |
| 6-TAMRA | 547 nm | 573 nm | Rose |

TABLE 9-continued

General fluorescent dyes for oligonucleotide labelling

| Dye | λ-excit | λ-emiss | colour |
|---|---|---|---|
| Redmond Red | 579 nm | 595 nm | Red |
| Cy3.5 | 588 nm | 604 nm | Purple |
| ROX | 585 nm | 610 nm | Red |
| Pulsar 650 | 490 nm | 650 nm | purple |
| Cy5 (also Quasar 670) | 646 nm | 662 nm | Violet |
| Cy5.5 | 683 nm | 707 nm | Dark Blue |

TABLE 10

Alexa dyes (Invitrogen)

| Alexa Dye | λ-excit | λ-emiss |
|---|---|---|
| Alexafluor 350 | 350 nm | 442 nm |
| Alexafluor 405 | 405 nm | 421 nm |
| Alexafluor 430 | 430 nm | 540 nm |
| Alexafluor 488 | 488 nm | 518 nm |
| Alexafluor 500 | 502 nm | 524 nm |
| Alexafluor 514 | 518 nm | 542 nm |
| Alexafluor 532 | 534 nm | 553 nm |
| Alexafluor 546 | 546 nm | 565 nm |
| Alexafluor 555 | 552 nm | 567 nm |
| Alexafluor 568 | 578 nm | 603 nm |
| Alexafluor 594 | 591 nm | 618 nm |
| Alexafluor 610 | 612 nm | 628 nm |
| Alexafluor 633 | 633 nm | 650 nm |
| Alexafluor 647 | 647 nm | 662 nm |
| Alexafluor 660 | 663 nm | 690 nm |
| Alexafluor 680 | 679 nm | 702 nm |
| Alexafluor 700 | 696 nm | 719 nm |
| Alexafluor 750 | 752 nm | 779 nm |

TABLE 11

ATTO dyes (ATTO-TEC GmbH)

| ATTO Dye | λ-excit | λ-emiss |
|---|---|---|
| ATTO 425 | 436 nm | 484 nm |
| ATTO 465 | 453 nm | 508 nm |
| ATTO 488 | 501 nm | 523 nm |
| ATTO 495 | 495 nm | 527 nm |
| ATTO 520 | 525 nm | 545 nm |
| ATTO 532 | 532 nm | 553 nm |
| ATTO 550 | 554 nm | 576 nm |
| ATTO 565 | 563 nm | 592 nm |
| ATTO 590 | 594 nm | 624 nm |
| ATTO 610 | 615 nm | 634 nm |
| ATTO 620 | 619 nm | 643 nm |
| ATTO 635 | 635 nm | 659 nm |
| ATTO 647 | 645 nm | 669 nm |
| ATTO 655 | 633 nm | 684 nm |
| ATTO 680 | 680 nm | 700 nm |
| ATTO 700 | 700 nm | 719 nm |

TABLE 12

Dyomics dyes (Dyomics GmbH)

| Dyomics Dye | λ-excit | λ-emiss |
|---|---|---|
| DY415 | 418 nm | 465 nm |
| DY495 | 495 nm | 520 nm |
| DY505 | 505 nm | 530 nm |
| DY547 | 557 nm | 574 nm |
| DY548/549 | 558 nm | 572 nm |
| DY550 | 553 nm | 578 nm |
| DY555 | 555 nm | 580 nm |
| DY556 | 548 nm | 573 nm |

TABLE 12-continued

Dyomics dyes (Dyomics GmbH)

| Dyomics Dye | λ-excit | λ-emiss |
|---|---|---|
| DY560 | 559 nm | 578 nm |
| DY590 | 580 nm | 599 nm |
| DY610 | 609 nm | 629 nm |
| DY615 | 621 nm | 641 nm |
| DY630 | 636 nm | 657 nm |
| DY631 | 637 nm | 658 nm |
| DY632/633/634 | 637 nm | 657 nm |
| DY635 | 647 nm | 671 nm |
| DY636 | 645 nm | 671 nm |
| DY647 | 652 nm | 673 nm |
| DY648 | 653 nm | 674 nm |
| DY650 | 653 nm | 674 nm |
| DY651 | 653 nm | 678 nm |
| DY652 | 654 nm | 675 nm |
| DY675/676 | 674 nm | 699 nm |
| DY677 | 673 nm | 694 nm |
| DY680/682 | 690 nm | 709 nm |
| DY700 | 702 nm | 723 nm |
| DY701 | 706 nm | 731 nm |
| DY730 | 734 nm | 750 nm |
| DY731/734 | 736 nm | 759 nm |
| DY732 | 736 nm | 759 nm |
| DY750 | 747 nm | 776 nm |
| DY751 | 751 nm | 779 nm |
| DY752 | 748 nm | 772 nm |
| DY776 | 771 nm | 801 nm |
| DY781 | 783 nm | 800 nm |
| DY782 | 782 nm | 800 nm |

TABLE 13

Dyomics Megastokes dyes (Dyomics GmbH). All can be excited at 488 nm

| Dyomics Dye | λ-excit | λ-emiss |
|---|---|---|
| DY475XL | 493 nm | 514 nm |
| DY480XL | 500 nm | 630 nm |
| DY485XL | 485 nm | 560 nm |
| DY500XL | 505 nm | 555 nm |
| DY510XL | 509 nm | 590 nm |
| DY600XL | 603 nm | 634 nm |
| DY520XL | 520 nm | 664 nm |

TABLE 14

Hilyte dyes (Cambridge Bioscience)

| Dye | λ-excit | λ-emiss |
|---|---|---|
| Hilyte Fluor 488 | 502 nm | 527 nm |
| Hilyte Fluor 555 | 552 nm | 569 nm |
| Hilyte Fluor 647 | 649 nm | 674 nm |
| Hilyte Fluor 680 | 678 nm | 699 nm |

TABLE 15

Low excitation wavelength (UV) fluorophores

| Derivative | Abs * | Em * |
|---|---|---|
| Alexa Fluor 350 | 346 | 442 |
| Alexa Fluor 405 | 402 | 412 |
| Anilinonaphthalene | 326 | 462 |
| Bimane | 375 | 456 |
| Dansyl | 328 | 563 |
| Dapoxyl | 374 | 572 |
| Dibromobimane | 394 | 490 |
| Diethylaminocoumarin | 384 | 470 |
| Dimethylaminocoumarin | 376 | 465 |

TABLE 15-continued

Low excitation wavelength (UV) fluorophores

| Derivative | Abs * | Em * |
|---|---|---|
| Dimethylarninonaphthalene | 391 | 500 |
| Monobromobimane | 394 | 490 |
| Monochlorobimane | 394 | 490 |
| Naphthalene | 336 | 490 |
| Pyrene | 339 | 384 |
| Stilbene | 329 | 408 |

REFERENCES CITED

Patent Documents

| | | |
|---|---|---|
| U.S. Pat. No. 5,691,146 | November 1997 | Mayrand |
| U.S. Pat. No. 6,174,670 B1 | January 2001 | Rasmussen et al |
| WO 01/36668 A1 | May 2001 | Sauer et al |
| U.S. Pat. No. 6,635,427 B2 | October 2003 | Wittwer et al |
| WO 01/73118 A2 | October 2001 | French et al |

OTHER PUBLICATIONS

1. Brown et al (2001) Synthesis of a modified thymidine monomer for site-specific incorporation of reporter groups into oligonucleotides. *Tetrahedron Lett.* 42, 2587-2591.
2. Brown et al (2003) Synthesis of fluorophore and quencher monomers for use in Scorpion primers and nucleic acid structure probes. *Organic and Biomolecular Chem.* 1, 2267-2275.
3. Crockett & Wittwer (2001) Fluorescein-Labeled Oligonucleotides for Real-Time PCR: Using the Inherent Quenching of Deoxyguanosine Nucleotides. *Anal. Biochem.*, 290, 89-97.
4. Dobson et al (2003) Synthesis of HyBeacons and dual-labelled probes containing 2'-fluorescent groups for use in genetic analysis. *Chem. Comm.* 1234-1235
5. Elnifro et al (2000) PCR and restriction endonuclease analysis for rapid identification of Human Adenovirus subgenera. *J. Clin. Microbiol.* 38: 2055-2061
6. French et al (2001) HyBeacon probes: a new tool for DNA sequence detection and allele discrimination. *Molecular and Cellular Probes.* 15, 363-74
7. French et al (2002) Ultra-rapid DNA analysis using HyBeacon probes and direct PCR amplification direct from saliva. *Molecular and Cellular Probes.* 16, 319-26
8. Hawkins et al (1997) Fluorescence properties of pteridine nucleoside analogs as monomers and incorporated into oligonucleotides. *Anal. Biochem.* 244, 86-95
9. Heinlein et al (2003) Photoinduced electron transfer between fluorescent dyes and guanosine residues DNA-hairpins. *J. Phys. Chem.* 107, 7957-7964
10. Knemeyer et al (2000). Probes for detection of specific DNA sequences at the single-molecule level. *Anal. Chem.* 72, 3717-24
11. Lee et al (1994) A fluorogenic assay for DNA cleavage reactions characterized with BamHI restriction endonucleoase. *Anal. Biochem.* 220, 377-83
12. Lee et al (2002) ResonSense: simple linear fluorescent probes for quantitative homogeneous rapid polymerase chain reaction. *Analytica Chimica Acta* 457, 61-70
13. Marks et al (2005) Molecular basis of action of HyBeacon fluorogenic probes: A spectroscopic and molecular dynamics study. *Journal of Biomolecular Structure & Dynamics* 23, 49-62
14. Nazerenko et al (2002) Multiplex quantitative PCR using self-quenched primers labeled with a single fluorophore. *Nucleic Acids Res.* 30, e37
15. Nazerenko et al (2002b) Effect of primary and secondary structure of oligodeoxyribonucleotides on the fluorescent properties of conjugated dyes. *Nucleic Acids Res.* 30, 2089-2195
16. Norlund et al (1989) Structure and dynamics of a fluorescent DNA oligomer containing the EcoRI recognition sequence: fluorescence, molecular dynamics and NMR studies. *Biochemistry* 28, 9095-9103
17. Seidel et al (1996) Nucleobase-specific quenching of fluorescent dyes. 1. Nucleobase one-electron redox potentials and their correlation with static and dynamic quenching efficiencies. *J. Phys. Chem.,* 100, 5541-5553.
18. Solinas et al (2001) Duplex Scorpion primers in SNP assays and FRET applications. *Nucleic Acids Res.* 29, e96
19. Svanvik et al (2000) Detection of PCR products in real time using light-up probes. *Analytical Biochemistry* 287, 179-182
20. Thelwell et al (2000) Mode of action and application of Scorpion Primers to mutation detection. *Nucleic Acids Res.* 28, 3752-3761
21. Tyagi & Kramer (1996) Molecular Beacons: probes that fluoresce upon hybridisation. *Nature Biotechnology* 14, 303-308
22. Whitcombe et al (1999) Detection of PCR products using self-probing amplicons and fluorescence. *Nature Biotechnology* 17, 804-807.
23. Xu et al (1994) Melting and premelting transitions of an oligomer measured by DNA base fluorescence and absorption. *Biochemistry* 33, 9592-9599
24. Zucker (2003) Mfold web server for nucleic acid folding and hybridisation prediction. *Nucleic Acids Res.* 31, 3406-3415

The invention claimed is:

1. A single-stranded DNA oligonucleotide, having substantially no secondary structure formed by intramolecular base pairing between one or more parts of the oligonucleotide made of four or more consecutive nucleotide residues which are the inverse complement of any other part of the oligonucleotide, and which is formed of nucleotide residues wherein the bases of two or more internal nucleotide residues are labelled with a fluorophore without an associated quencher, wherein at least two of the nucleotide residues labelled with a fluorophore are separated by at least two unlabelled nucleotide residues, and wherein the 3' nucleotide residue does not contain a 3' hydroxyl.

2. An oligonucleotide according to claim 1 wherein up to about one-third of the internal residues are labelled with a fluorophore.

3. An oligonucleotide according to claim 1 wherein all of the nucleotide residues labelled with a fluorophore are separated by at least two unlabelled nucleotide residues.

4. An oligonucleotide according to claim 1 which contains at least one G residue, wherein at least one of the fluorophore-labelled nucleotide residues is positioned adjacent to at least one of the G residues.

5. An oligonucleotide according to claim 1 wherein the 3' nucleotide residue contains a 3' phosphate or is a 3' deoxy residue.

6. An oligonucleotide according to claim 1 which contains from 10 to 50 nucleotide residues.

7. An oligonucleotide according to claim 6 which contains from 15 to 30 nucleotide residues.

8. An oligonucleotide according to claim 6 which contains from 2 to 10 fluorophore-labelled internal nucleotide residues.

9. An oligonucleotide according to claim 7 which contains from 2 to 5 fluorophore-labelled internal residues.

10. An oligonucleotide according to claim 1 wherein each fluorophore is the same fluorophore.

11. An oligonucleotide according to claim 1 which contains two or more different fluorophores.

12. An oligonucleotide according to claim 1 wherein the fluorophore is selected from the group consisting of fluorescein-based dyes such as 6-carboxyfluorescein (FAM), tetrachlorofluorescein (TET), hexachlorofluorescein (HEX), rhodamine-based dyes such as 6-carboxy-X-rhodamine (ROX), 6-carboxytetramethylrhodamine (TAMRA); a Cy family dye such as Cy3 or Cy5; other fluorophores such as NED or JOE, and Alexa dyes, Atto dyes, Dyomic dyes, Dyomic megastoke dyes and Thilyte dyes.

13. An oligonucleotide according to claim 11 which contains two different fluorophores, one being FAM and the other ROX.

14. An oligonucleotide according to claim 1 wherein the fluorophore does not intercalate into double stranded DNA.

15. An oligonucleotide according to claim 1 which has a sequence fully complementary to a target polynucleotide sequence.

16. An oligonucleotide according to claim 15 wherein the target polynucleotide sequence is selected from the group consisting of the human genome including any gene therein or allele thereof, the mouse genome including any gene therein or allele thereof, and the genome of any infectious agent including any gene therein or allele thereof, or wherein the oligonucleotide has a sequence complementary to sheep PrP gene (NM 001009481).

17. An oligonucleotide according to claim 16 which has a sequence fully complementary to any one of the following human genes or an allele thereof:

| | |
|---|---|
| N-acetyltransferase 2 | X14672 |
| Factor V Leiden | AY364535 |
| Factor II | AF493953 |
| MTHFR | NM_005957 and |
| Sickle cell anaemia | AY356351. |

18. An oligonucleotide according to claim 16 which has a sequence fully complementary to the genome or any gene therein or allele thereof of the following infectious agents:

| | |
|---|---|
| *Chlamydia trachomatis* | X07547 |
| Adenovirus | AJ293905 |
| Influenza A | AY130766 |
| *Streptococcus pneumoniae* | X52474 |
| MRSA | AJ810121. |

19. An oligonucleotide according to claim 16 which has a sequence fully complementary to one allele of a gene.

20. An oligonucleotide according to claim 1 which has at least 70% sequence identity with the complement of the target polynucleotide sequence.

21. An oligonucleotide according to claim 1 which has at least 80% sequence identity with the complement of the target polynucleotide sequence.

22. An oligonucleotide according to claim 19 wherein the sequence complementary to the nucleotide sequence difference of the given allele compared to another allele of the gene is located towards the middle of the oligonucleotide.

23. An oligonucleotide according to claim 1 immobilised on or within a support.

24. An array of oligonucleotides immobilised at spaced locations on or within a support wherein at least one of the oligonucleotides is an oligonucleotide according to claim 1.

25. An array of oligonucleotides according to claim 24 wherein each oligonucleotide is a single-stranded oligonucleotide, having substantially no secondary structure formed by intramolecular base pairing between one or more parts of the oligonucleotide made of four or more consecutive nucleotide residues which are the inverse complement of any other part of the oligonucleotide, and formed of nucleotide residues wherein two or more internal nucleotide residues are labelled with a fluorophore without an associated quencher.

26. A method of investigating a target polynucleotide sequence in a sample containing polynucleotide sequences, the method comprising contacting the sample with an oligonucleotide according to claim 1 which is able to hybridise to the target polynucleotide sequence, and determining whether hybridisation occurs.

27. A method according to claim 26 wherein detection of an increase in fluorescence is used to determine whether hybridisation has occurred between the oligonucleotide and the target polynucleotide sequence.

28. A method according to claim 26 wherein the method is performed at a predetermined temperature near, or over a range of temperatures encompassing, the melting point of the hybrid or hybrids formed between the target polynucleotide sequence and the said oligonucleotide.

29. A method according to claim 26 wherein the oligonucleotide is fully complementary to the target polynucleotide sequence.

30. A method according to claim 26 wherein the oligonucleotide is not fully complementary to the target polynucleotide sequence.

31. A method according to claim 30 wherein the oligonucleotide has at least 70% sequence identity with the target polynucleotide sequence.

32. A method according to claim 31 wherein the oligonucleotide has at least 80% sequence identity with the target polynucleotide sequence.

33. A method according to claim 26 wherein the target polynucleotide sequence investigated is one or more alleles of a gene.

34. A method according to claim 33 wherein the oligonucleotide is able to hybridise to more than one allele of the gene.

35. A method according to claim 26 wherein the method is used to detect, identify or quantitate the presence or amount of the target polynucleotide sequence in the sample.

36. A method according to claim 26 wherein the sample contains polynucleotide sequences produced by amplification.

37. A method according to claim 36 wherein the polynucleotide sequences are produced by any one or more of polymerase chain reaction (PCR), reverse transcription PCR (RT-PCR), ligase chain reaction (LCR), strand displacement amplification (SDA), transcription mediated amplification (TMA), rolling circle amplification (RCA) or nucleic acid sequence based amplification (NASBA).

38. A method according to claim 36 wherein the amplification of the polynucleotide sequences in the sample is performed in the presence of the oligonucleotide which is able to hybridise to the target polynucleotide sequence.

39. A method according to claim 38 wherein observation of fluorescence is made during the amplification of the polynucleotide sequences in the sample.

40. A method according to claim 36 wherein the polynucleotide sequences in the sample are produced by amplification from a biological source without prior nucleic acid extraction.

41. A method according to claim 37 wherein the PCR is an asymmetric amplification.

42. A method according to claim 28 wherein the oligonucleotide which is able to hybridise to the target polynucleotide sequence, the sample which may contain the polynucleotide target sequence or both are immobilised on or within a support.

43. A method according to claim 28 wherein the target polynucleotide sequence is selected from the group consisting of the human genome including any gene therein or allele thereof, the mouse genome or any gene therein or allele thereof, and the genome of any infectious agent including any gene therein or allele thereof.

44. A process for making an oligonucleotide according to claim 15, the process comprising selecting a target polynucleotide sequence and synthesizing an oligonucleotide which has a sequence complementary to the target polynucleotide and which is a single-stranded oligonucleotide, having substantially no secondary structure formed by intramolecular base pairing between one or more parts of the oligonucleotide made of four or more consecutive nucleotide residues which are the inverse complement of any other part of the oligonucleotide, and formed of nucleotide residues wherein two or more internal nucleotide residues are labelled with a fluorophore without an associated quencher.

45. A process according to claim 44 wherein the target polynucleotide sequence is selected from the group consisting of the human genome including any gene therein or allele thereof, the mouse genome including any gene therein or allele thereof, and the genome of any infectious agent including any gene therein or allele thereof.

46. A single-stranded DNA oligonucleotide, having substantially no secondary structure formed by intramolecular base pairing between one or more parts of the oligonucleotide made of four or more consecutive nucleotide residues which are the inverse complement of any other part of the oligonucleotide, and which is formed of nucleotide residues wherein the bases of two or more internal nucleotide residues are labelled with a fluorophore without an associated quencher, wherein at least two of the nucleotide residues labelled with a fluorophore are separated by at least two unlabelled nucleotide residues, wherein the 3' nucleotide residue does not contain a 3' hydroxyl and wherein each fluorophore is the same fluorophore.

47. A method of investigating a target polynucleotide sequence in a sample containing polynucleotide sequences produced by amplification, the method comprising contacting the sample with an oligonucleotide which is able to hybridise to the target polynucleotide sequence, and determining whether hybridisation occurs, wherein the oligonucleotide is a single-stranded oligonucleotide, having substantially no secondary structure formed by intramolecular base pairing between one or more parts of the oligonucleotide made of four or more consecutive nucleotide residues which are the inverse complement of any other part of the oligonucleotide, and which is formed of nucleotide residues wherein two or more internal nucleotide residues are labelled with a fluorophore without an associated quencher, wherein at least two of the nucleotide residues labelled with a fluorophore are separated by at least two unlabelled nucleotide residues.

48. A method according to claim 47 wherein the amplification of the polynucleotide sequences in the sample is performed in the presence of the oligonucleotide which is able to hybridise to the target polynucleotide sequence.

* * * * *

UNITED STATES PATENT AND TRADEMARK OFFICE
CERTIFICATE OF CORRECTION

PATENT NO.        : 8,383,791 B1
APPLICATION NO. : 11/988946
DATED             : February 26, 2013
INVENTOR(S)       : McDowell et al.

Page 1 of 1

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 790 days.

Signed and Sealed this

First Day of September, 2015

Michelle K. Lee
*Director of the United States Patent and Trademark Office*